United States Patent [19]
Cashmore et al.

[11] Patent Number: 5,824,859
[45] Date of Patent: Oct. 20, 1998

[54] BLUE LIGHT PHOTORECEPTORS AND METHODS OF USING THE SAME

[75] Inventors: Anthony Robert Cashmore, Penn Valley; Margaret Ahmad, Philadelphia; Chentao Lin, Upper Darby, all of Pa.

[73] Assignee: The Trustees of the University of Pennsylvania, Philadelphia, Pa.

[21] Appl. No.: 272,255

[22] Filed: Jul. 8, 1994

[51] Int. Cl.[6] .............................. A01H 5/00; A01H 1/00; C12N 15/00

[52] U.S. Cl. .................. 800/205; 435/172.3; 435/172.1; 435/320.1; 536/23.2; 536/23.6; 935/64

[58] Field of Search ............................. 435/172.3, 172.1, 435/320.1; 800/205; 536/23.2, 23.6; 935/64

[56] References Cited

U.S. PATENT DOCUMENTS

| | | | |
|---|---|---|---|
| 4,975,374 | 12/1990 | Goodman et al. | 435/172.3 |
| 5,098,838 | 3/1992 | Goodman et al. | 435/183 |
| 5,167,228 | 12/1992 | Czeisler et al. | 128/395 |
| 5,212,132 | 5/1993 | Dean et al. | 536/23.2 |
| 5,256,558 | 10/1993 | Coruzzi et al. | 435/240.1 |
| 5,296,462 | 3/1994 | Thomashow | 514/2 |
| 5,304,212 | 4/1994 | Czeisler et al. | 607/88 |
| 5,349,125 | 9/1994 | Horton et al. | 800/205 |

FOREIGN PATENT DOCUMENTS

WO 92/19724  12/1992  WIPO.

OTHER PUBLICATIONS van Der Krol et al. Inhibition of flower pigmentation by antisense CHS genes: promoter and minimal sequence requirements for the antisense effect. Plant Molecular Biology vol. 14: p. 457, 1990.

O'Brien et al., "Association of hY4 Pseudogenes with Alu Repeates and Abundance of hY RNA–like Sequences in the Human Genome" Gene, 116:285–289 (1992).

Mangold et al., "Gene and cDNA for Plant Cytochrome P450 Proteins (CYP72 Family) from *Catharanthus Roseus*, and Transgenic Expression of the Gene and a cDNA in Tobacco and *Arabidopsis Thaliana*" Plant Science, 96:129–136 (1994).

Ahmad and Cashmore, "HY4 Gene of *A. Thaliana* Encodes a Protein With Characteristics of Blue–Light Photoreceptor" Nature 366:162–166 (1993).

Assaad et al., "Epigenetic repeat–induced gene silencing (RIGS) in Arabidopsis" Plant Mol. Biol. 22:1067 (1993).

Assmann et al., "Blue Light Activates Electrongenic Ion Pumping in Guard Cell Protopalsts of *Vicia Faba*" Nature 318:285–287 (1985).

Boylan et al., "Oat Phytochrome Is Biologically Active in Transgenic Tomatoes" Plant Cell 1:765 (1989).

Brusslan et al., "An Arabidopsis Mutant with a Reduced Level of cab140 RNA Is a Result of Cosuppression" Plant Cell 5:667 (1993).

Corrochano et al., "Sex, light and carotenes: the development of Phycomyces" TIG 8 :278 (1992).

(List continued on next page.)

*Primary Examiner*—Gary Benzion
*Attorney, Agent, or Firm*—Panitch Schwarze Jacobs & Nadel, P.C.

[57] ABSTRACT

The invention features a substantially pure preparation of a nucleic acid encoding a HY4 or a HY4-related gene. The invention further features transgenic plants encoding a HY4 gene having a shorter stem than substantially homozygous wild type nontransgenic plants; and, transgenic plants comprising complementary HY4 sequences having a longer stem than substantially homozygous wild type nontransgenic plants.

34 Claims, 33 Drawing Sheets

OTHER PUBLICATIONS

Degli–Innocenti et al., "Genetic analysis of blue light–induced responses in *Neurospora crassa*" Senger, In: Blue light effects in biological systems. pp. 213–227 (1984).

Feldmann, "T–DNA insertion mutagenesis in Arabidopsis: mutational spectrum" *Plant J.* 1:71 (1991).

Fontes et al., "Growth phase dependence of the activation of a bacterial gene for carotenoid synthesis by blue light" EMBO Journal vol. 2 No. 4 p. 1265 (1993).

Foster et al., "Photorecptors Regulating Circadian Behavior: A Mouse Model" *J. Biological Rhythms* 8:S17–23 (1993).

Gallagher et al., "Light–mediated changes in two proteins found associated with plasma membrane fractions from pea stem sections" *Proc. Natl. Acad. Sci. USA* 85:8003 (1988).

Galland et al., "Photophysiology Of *Phycomyces blankesleesnus*" *Photochemistry and Photobiology* 795 (1984).

Gray et al., "Molecular biology of fruit ripening and its manipulation with antisense genes" *Plant Molec. Biol.* 19:69 (1992).

Hager and Brich, "Blue–light–induced phosphorylation of a plasma–membrane protein from phototropically sensitive tips of maize coleoptiles" *Planta.* 189:657 (1993).

Hager et al., "Redox Dependance of The Blue–Light–Induced Phosphorylation of A 100–kDa Protein on Isolated Plasma Membranes From Tips of Coleoptiles" *Planta* 190:120 (1993).

Hahlbrock et al., "Physiology and Molecular Biology of Phenylpropanoid Metabolism" *Ann. Rev. Plant Physiol. and Plant Mol. Biol.* 40:347 (1989).

Hoenecke et al., "Importance of 'Blue' Photon Levels for Lettuce Seedlings Grown under Right–light–emitting Diodes" *HortScience* 27(5) :427 (1992).

Horsch et al., "Leaf Disc transformation", Plant Molecular Biology Manual A5:1 (1988).

Kaufman, "Transduction of Blue–Light Signals" *Plant Physiol.* 102:333 (1993).

Keller et al., "Expression of a functional monocotyledonous phytochrome in transgenic tobacco" *EMBO J.* 8:1005 (1989).

Khurana and Poff, "Mutants of *Arabidopsis thaliana* with altered phototropism" *Planta.* 178:400 (1989).

Khurana et al., "Mutants of *Arabidopsis thaliana* with Decreased Amplitude in Their Phototropic Response" *Plant Physiol.* 91:685–689 (1989).

Kobayashi et al., "Molecular characterization of a gene encoding a photolyase from *Streptomyces griseus*" *Nucl. Acids Res.* 17:4731 (1989).

Konjevic et al., "Dependence of the phototropic response of *Arabidopsis thaliana* on fluence rate and wavelength" *Proc. Natl. Acad. Sci. USA* 86:9876 (1989).

Koornneef et al., "Genetic Control of Light–Inhibited Hypocotyl Elongation in *Arabidopsis Thaliana*" *Z. Pflanzenphysiol. Bd.* 100(S):147–160 (1980).

LaBate and Skene, "Selective Conservation of GAP–43 Structure in Vertebrate Evolution" *Neuron.* 3:299 (1989).

Laskowski and Briggs, "Regulation of Pea Epicotyl Elongation by Blue Light" *Plant Physiol.* 89, 293 (1989).

Leong et al., "A Blue Light–Sensitive Cytochrome–Flavin Complex From Corn Coleoptiles. Further characterization" *Photochem. Photobiol.* 34:697 (1981).

Li and Sancar, "Active Site of *Eschericha coli* DNA Photolyase Mutations at Trp277 Alter the Selectivity of the Enzyme without Affecting the Quantum Yield of Photorepair" *Biochemistry* 29:5698 (1990).

Liscum et al., "Genetic Separation of Phototropism and Blue Light Inhibition of Stem Elongation" *Plant Physiol.* 100:267 (1992).

Liscum and Hangarter, "Arabidopsis Mutants Lacking Blue Light–Dependent Inhibition of Hypocotyl Elongation" *Plant Cell* 3:685 (1991).

Liscum and Hangarter, "Light–Stimulated Apical Hook Opening in Wild–Type *Arabidopsis Thaliana* Seedlings" *Plant Physiol.* 101:567 (1993).

Malhotra et al., "Identification of Chromophore Binding Domains of Yeast DNA Photolyase" *J. Biol. Chem.* 267:2909 (1992).

Munoz and Butler, "Photoreceptor Pigment for Blue Light in *Neurospora crassa*" *Plant Physiol.* 55:421 (1975).

Münzner and Voigt, "Blue Light Regulation of Cell Division in *Chlamydomonas reinhardtii*" *Plant Physiol.* 99:1370 (1992).

Murashige and Skoog, "A Revised Medium for Rapid Growth and Bio Assays with Tobacco Tissue Cultures" *Physiol. Plant* 15:473 (1962).

Nagatani et al., "Rice type I phytochrome Hypocotyl elongation in transgenic tobacco seedlings" *Proc. Natl. Acad. Sci. USA* 88:5207 (1991).

Napoli et al., "Introduction of a Chimeric Synthase Gene into Petunia Results in Reversible Co–Suppression of Homologus Genes in trans" *Plant Cell* 2:279 (1990).

Oeller et al., "Reversible Inhibition of Tomato Fruit Senescence by Antisense RNA" *Science* 254:437 (1991).

Pang and Hays, "UV–B–Inducible and Temperature–Sensitive Photoreactivation of Cyclobutane Pyrimidine Dimers in *Arabidopsis thaliana*" *Plant Physiol.* 95:536 (1991).

Payne et al., "Reconstitution of *Escherichia coli* Photolyase with Flavins and Flavin Analogues" *Biochemistry* 29:5706 (1990).

Poff and Buler, "Absorbance changes induced by blue light in *Phycomyces blakesleeanus* and *Dictyostelium discoideum*" *Nature* 248:799 (1974).

Poole, "Cellular signaling machinery: Conservation from plant stomata to Lymphocytes" *Proc. Natl. Acad. Sci. USA* 90:3125 (1993).

Quail, "PHYTOCHROME: A Light–activated Molecular Switch that Regulates Plant Gene Expression" *Ann. Rev. Genet.* 25:389 (1991).

Rensberger, "Genetics: In Sync With Circadian Rhythm" *The Washington Post* A2 Monday, May 2, 1994.

Reymond et al., "Light–induced phosphorylation of a membrane protein plays an early role in signal transduction of phototropism in *Arabidopsis thaliana*" *Proc. Natl. Acad. Sci. USA* 89:4718 (1992).

Reymond et al., "Blue Light Activates a Specific Protein Kinase in Higher Plants" *Plant Physiol.* 100:655 (1992).

Ruiz–Opazo and Nadai–Ginard, "Alternative Splicing of Duplicated Isotype–Specific Exons for the Production of Smooth and Striated Muscle Isoforms" *J. Biol. Chem.* 262:4755 (1987).

Sancar, "DNA photolyases: Physical properties, action mechanism, and roles in dark repair" *Mut. Res.* 236:147 (1990).

Sanger et al., "DNA sequencing with chain–terminating inhibitors" *Proc. Natl. Acad. Sci. USA* 74:5463 (1977).

Schardl et al., "Design and construction of a versatile system for the expression of foreign genes in plants" *Gene* 61:1 (1987).

Schindler et al., "Heterodimerization between light–regulated and ubiquitously expressed Abrabidopsis GBF bZIP proteins" *EMBO J.* 11:1261 (1992).

Shimazaki et al., "Involvement of Calmodulin and Calmodulin–Dependent Myosin Light Chain Kinase in Blue Light–Dependent $H_+$Pumping by Guard Cell Protoplasts from *Vicia faba* L." *Plant Physiol.* 99:1416 (1992).

Short and Briggs, "Characterization of a Rapid, Blue Light–Mediated Change in Detectable Phosphorylation of a Plasma Membrane Protein from Etiolated Pea (*Pisum sativum* L.) Seedlings" *Plant Physiol.* 92:179 (1990).

Smith et al., "Antisense RNA inhibition of Polygalacturonase gene expression in transgenic tomatoes" *Nature* 334:724 (1988).

Tlalka and Gabrys, "Influence of calcium on blue–light–induced chloroplast movement in *Lemna trisulca* L." *Planta* 491 (1993).

Truman, "Extraretinal Photoreception in Insects" *Photochem. Photobiol.* 23:215–225 (1976).

Warpeha et al., "Blue–Light Regulation of Specific Transcript Levels in *Pisum sativum*" *Plant Physiol.* 91:1030 (1989).

Warpeha and Kaufman, "Two distinct blue–light responses regulate the levels of transcripts of specific nuclear–coded genes in pea" *Planta.* 182:553 (1990).

Warpeha et al., "A blue–light–activated GTP–binding protein in the plasma membranes of etiolated peas" *Proc. Natl. Acad. Sci. USA* 88:8925 (1991).

Warpeha et al., "A Flavoprotein May Mediate The Blue Light–Activated Binding Of Guanosine 5'–Triphosphate To Isolate Plasma Membranes of *Pisum sativum* L." *Photochem. Photobiol.* 55:595 (1992).

Yajima et al., "Cloning and functional characterization of a eucaryotic DNA photolyase gene from *Neurospora crassa*" *Nucl. Acids Res.* 19:5359 (1991).

Yamamoto, "Dissection of functional domains in *Escherichia coli* DNA photolyase by linker–mutagenesis" *Molec. Gen. Genet.* 232:1 (1992).

Yasuhira and Yasui, "Visible Light–Inducible Photolyase Gene from the Goldfish *Carassius auratus*" *J. Biol. Chem.* 267:25644 (1992).

```
                    INTRON
                      ↓
WT      ACC GGG  TAAAAAGTGCATTTG      2058
        Thr Gly  ***                   681

2.23N   ACC GGG TAT GTA ACT CGC       2055
        Thr Gly Tyr Val Thr Arg        685

2.23N   AAA TCG ACT CTC TCA ACA       2073
        Lys Ser Thr Leu Ser Thr        691

2.23N   ATA AGT TCA CAT AAA GAT       2091
        Ile Ser Ser His Lys Asp        697

2.23N   CCT AAA CAT TTT CAA ATT       2109
        Pro Lys His Phe Gln Ile        703

2.23N   GAA AGT CTC CAA ATT TTC       2127
        Glu Ser Leu Gln Ile Phe        709

2.23N   AGT AAG TTT CAA......         2139
        Ser Lys Phe Gln......          713
```

*FIG. 2C*

```
-147                                                            TCAAAAATCTTTTTTTGTTGTC
 -61  AAAGTAATTTTTATGTGATTATTGCCAAGAAAAGTTTTTTTTAGTTTTTTGTGAGAG

61  GATCTTAGGGTTGAAGATAATCCAGCTTTA GCAGCAGCAGTAAGAGCTGGTCCAGTGATT
      AspLeuArgValGluAspAsnProAlaLeu AlaAlaAlaAlaArgAlaAlaGlyProValIle

181  TGGTGGCTCAAGAACAGTTGGCTCAGCTT GATTCTTCTCTTAGAAGTCTTGGTACTTGT
      TrpTrpLeuLysAsnSerLeuAlaGlnLeu AspSerSerLeuArgSerLeuGlyThrCys
                                                       ↓INTRON
 301  GGTGCTTCTCAGATCTCTTCTTCAACCATTTG TATGATCCATTGTCTTTGGTGCCTGATCAC
      GlyAlaSerGlnIleSerPhePheAsnHisLeu TyrAspProLeuSerLeuValArgAspHis

421  CTTTATGAGCCATGGGAAGTGACTGATGAA TTAGGCCCTCCTTCTCTATGTTTCTGCG
      LeuTyrGluProTrpGluValThrAspGlu LeuGlyArgProPheSerMetPheAlaAla
                    ↓INTRON
 541  AAGATCATTTCAGGGGATGTGTCTAAATGT GTTGCGGATCCATTGGTGTTGAGGATGAC
      LysIleIleSerGlyAspValSerLysCys ValAlaAspProLeuValPheGluAspAsp

661  GATAAAGCTCTCACAACGTTTATAAACGGT CCATTGCTTGAATACTCTAAGAACCGCAGA
      AspLysAlaLeuThrThrPheIleAsnGly ProLeuLeuGluTyrSerLysAsnArgArg

781  GTGAGAAAAGTTTTTCATCTTGTTCGGATC AAACAGGTCGCGTGGGCAAACGAAGGAAAC
      ValArgLysValPheHisLeuValArgIle LysGlnValAlaTrpAlaAsnGluGlyAsn

901  AGGTACATAAGTTTTAACCATCCATATTCC CATGAAAGACCACTTCTTGGCCATCTAAAG
      ArgTyrIleSerPheAsnHisProTyrSer HisGluArgProLeuLeuGlyHisLeuLys

1021  TATCCGTTGGTCGATGCCGGGATGAGAGAG TTATGGGCTACTGGTTGCATGATCGC
      TyrProLeuValAspAlaGlyMetArgGlu LeuTrpAlaThrGlyLeuTrpLeuHisAspArg
```

| FIG. 3A | FIG. 3B |
|---------|---------|
| FIG. 3C | FIG. 3D |

FIG. 3B

```
TTTCTTCTCGAGAGATAAGTGACCAAAGGGTTTCGATTTCTGGAAATAGTTTGAATAAA
ATGTCTGGTTCTGTATCTGGTTGTGTGGTTCT GGTGGTTGTAGTATTGTATGGTTAGAAGA
MetSerGlySerValSerGlyCysGlySer  GlyGlyCysSerIleValTrpPheArgArg   20

GCTCTCTGTTTGGGCACCAGAAGAAGAA   GGACACTATCATCCAGGTAGGGTTTCTAGG
AlaLeuPheValTrpAlaProGluGluGlu  GlyHisTyrHisProGlyArgValSerArg   60

CTTATCACCAAGACATCTACTGATAGTGTT  GCTTCTCTTGATGTTGTTAAATCCACT
LeuIleThrLysArgSerThrAspSerVal  AlaSerLeuLeuAspValValLysSerThr   100

CGAGCTAAAGATGTTTTGACGGCCCAAGGC  ATAGCGGTTCGATCATTCAACCAGACTTG
ArgAlaLysAspValLeuThrAlaGlnGly  IleAlaValArgSerPheAsnAlaAspLeu   140

TTTTGGGAGAGATGTCTTAGTATGCCTTAT GACCCTGAGTCTCCTCTTCCACCTAAG
PheTrpGluArgCysLeuSerMetProTyr  AspProGluSerProLeuProProLys     180

TCTGAGAAAGGAAGCAATGCACTTCTGGCT  CGTGCTTGGTCTCCTGGATGGAGTAATGGT
SerGluLysGlySerAsnAlaLeuLeuAla  ArgAlaTrpSerProGlyTrpSerAsnGly   220

AAAGCCCGATAGTGCTACAACCTCGTTCTT  TCTCCACACTTGCATTTTGGGAAGTGAGT
LysAlaAspSerAlaThrThrSerPheLeu  SerProHisLeuHisPheGlyGluValSer   260

GAGGCCCGGGAAGAAAAGCCTGAATCTTTC  CTGAAATCTATTGGTCTCAGGGAGTATTCT
GluAlaGlyGluGluSerValAsnLeuPhe  LeuLysSerIleGlyLeuArgGluTyrSer   300
                                                     hy4-1  A

TTCTTCCCTTGGGCTGTGATGAGAACTAT   TTCAAGGCATGGAGGCAAGGCCGGACTGGA
PhePheProTrpAlaValAspGluAsnTyr  PheLysAlaTrpArgGlnGlyArgThrGlu   340
                                                     hy4-4  A
                                                     Asp

ATAAGAGTAGTTGTTTCAAGCTTCTTTGTT  AAAGTGCTTCAATTACCATGGAGATGGGGG
IleArgValValValSerSerPhePheVal  LysValLeuGlnLeuProTrpArgTrpGly   380
```

FIG. 3C

```
1141 ATGAAGTATTTCTGGGACACACTTCTTGAT GCCGATTTAGAAAAGCCGATGCTTCTTGGTTGG
     MetLysTyrPheTrpAspThrLeuLeuAsp AlaAspLeuGluSerAspAlaLeuGlyTrp

1261 TTTGAAGGGTACAAGTTTGATCCAAATGGT GAATACGTAAGGCGATGGCTTCCTGAACTC
     PheGluGlyTyrLysPheAspProAsnGly GluTyrValArgArgTrpLeuProGluLeu

1381 GCTGCTGGTATCGAGCTTGGATCAAACTAT CCTCTACCAATTGTTGGATTAGACGAAGCA
     AlaAlaGlyIleGluLeuGlySerAsnTyr ProLeuProIleValGlyLeuAspGluAla

1501 GCAATAGAGAACGGATCCGAAGAAGGACTT GGAGATTCTCGAGGTAGAGGAAGCTCCT
     AlaIleGluAsnGlySerGluGluGlyLeu GlyAspSerAlaGluValGluAlaPro
                   hy4-3                         T-DNA hy4-2

1621 AGGAGATATGAGGATCAGATGGTTCCAAGC ATTACTTCTTTGATCAGACCTGAAGAA
     ArgArgTyrGluAspGlnMetValProSer IleThrSerLeuIleArgProGluGlu

1741 AGGAACATGGTTAACACCAACCAAGCTCAG CAGCGGAGAGCAGAACCGGCTTCAAACCAA
     ArgAsnMetValAsnThrAsnGlnAlaGln GlnArgArgArgAlaGluProAlaSerAsnGln

1861 ACAGCGGAATCTTCCAGCAGCGAAGGAGA GAAAGAAGCGGAGGCATAGTCCCCGAGTGG
     ThrAlaGluSerSerSerGlyArgArg GluArgSerGlyGlyIleValProGluTrp

1981 ACGTCTAGCTACTTGCAGAATCACCATGAA ATACTGAACTGGAGACGGCTTTCACAAACC
     ThrSerSerTyrLeuGlnAsnHisHisGlu IleLeuAsnTrpArgArgLeuSerGlnThr

2101 GGTGAAATCTGGTTGGACTGTAAACCGAGTACATTTGGTACGGTTTAATGTAATTCCGGTTA
2225 TCCATCATGTTATAATACACTGTATAGTAAGTAGTCTGTTGCTTGTGTATTAGACCAGGTC
```

FIG. 3D

```
CAATACATTACCGGTACTCTCCCGGATAGC  CGGGAGTTTGATCGCCATAGATAACCCTCAG
GlnTyrIleThrGlyThrLeuProAspSer  ArgGluPheAspArgIleAspAsnProGln  420

TCTAGACTCCCGACAGACTGGATACATCAT  CCGTGGAACGCCACCTGAGTCCGTTCTTCAA
SerArgLeuProThrAspTrpIleHisHis  ProTrpAsnAlaProGluSerValLeuGln  460

AAAGCACGGCTTCATGAAGCGCTTTCACAG  ATGTGGCAACTAGAAGCTGCTTCAAGAGCT
LysAlaArgLeuHisGluAlaLeuSerGln  MetTrpGlnLeuGluAlaAlaSerArgAla  500

ATAGAGTTCCCAAGGGACATTACAATGGAA  GAGACTGAACCAACCAGACTCAACCCAAAC
IleGluPheProArgAspIleThrMetGlu  GluThrGluProThrArgLeuAsnProAsn  540

GACGAAGAGTCGTCTCTTAATTTGAGAAAT  TCAGTAGGAGATAGCAGAGCAGAGGTTCCA
AspGluGluSerSerLeuAsnLeuArgAsn  SerValGlyAspSerArgAlaGluValPro  580

GTCACTGCTATGATTCCAGAATTTAATATC  AGAATTGTTGCAGAGAGACTGTATTGGAGGAGGAAGTACA
ValThrAlaMetIleProGluPheAsnIle  ArgIleValAlaGluSerThrGluAspSer  620

TCTCCAGGGTACTCAGAGCAGTTCCCTAGT  GAAGAAAATCGTATTGGAGGAGGAAGTACA
SerProGlyTyrSerGluGlnPheProSer  GluGluAsnArgIleGlyGlyGlySerThr  660
→ INTRON
GGG TAAAAAGTGCATTTGGAGGTGCAAAAGGAGGAACATCATAAGGGCTGTAACTCCG     681
Gly ***

TGGGGCTGGAGAGAAACTATGTAGGAGTTTGTCTGATGTACATTTTTATTTATCTCTGGT
TCATACTTGTTGGCTTTCAAAGTTTT
```

FIG. 4A

```
phr N.c.   MAPSKRKASAPPQTSHVNGNPSADKKRKTTTD
phr S.c.                                                                                                                    M hy4 A.t.   MSGSVSGGCGSGGCSIVWFRRDLRVEDNPALAAAVR----      -AGPVIALEVWAPEEEGHYHP
phr E.c.                 MTTHLVWFRQDLRLHDNLALAAAC----RNSSARVLALYIATPRQWATHNM
phr S.t.                 MPTHLVWFRRDLRLQDNLALAAAC----RDASARVLALYISTPAQWQAHDM
phr N.c.                 VRQAVVHWFKMDLRLIHDNRSLWLASQ----KAKEAGVPLICLYVLSPEDLEATLR
phr S.c.                 NVSTVMHWFRNDLRLYDNVGLYKSVALFQQLRQKNAKAKLYAVYVINEDDWRAHMD
phr H.h.                         MQLFWHRRDLRTTDNRGLAAAAPGVTAVDGGHDQGPVAAVFCFDDEVL--AHA
phr A.n.                        MAAPILFWHRRDLRLSDNIGLAAARA------QSAQLIGLFCLDPQILQSADM
phr S.g.                 MSVAVVLFTSDLRLHDNPVLRAA-------LRDADEVVPLFVRDDAVHRAGFD hy4 A.t.   RDHRAKDVL----TAQGIAVRSFNADLLYEPWEVTDELGRPFSMFAAF----WER----
phr E.c.   RDVEVERAL----RNVVCEGFDDSVILPPGAVMTGNHEMYKVFTPFKNASIKRLREGMPECV-
phr S.t.   RDRAVEKTL----PSVICEGFDDSVILAPGAVMTGNHEMYKVFTPFKNASIKRLKEDIPPCV-
phr N.c.   REAKLVKLLAEGEKEMAADVVHDTCVVMPGALQSGSGGQYAVYSPWFRAWITKHIEEN-PECLE
phr S.c.   RDIRLLE----NEDHRLQLKYYHDSCIVAPGLITTDRCTNYSVFTPWYKKWV----
phr H.h.   RDAGVRDAL----DAAGVAHAQFHDAVHHRPGEIRTNAGDPYSVYTYFWRKWQDREKNPPA---
phr A.n.   RDGQVAAAL----KTAGIRAVQLWDQLLHSPDQILSGSGNPYSVYGPFWKNWQAQPKPTPV---
phr S.g.   REQRIREALADSGRELHVHDAVV--TALAPGRVVPTGGKDHFAVFTPYFRRWEAEGVRGTQAPR
                                                                       W277
hy4 A.t.   EYSKNRRKADSATISFLSPHLHFGEVSVRKVFHLVRIKQVAWANEGNEAGEESVNLFEKSIGLRE
phr E.c.   EYEQQRDFPAVEGTSRLSASLATGGLSPRQCLHRLA-EQPQALDGG--AGSV-WINELIWRE
phr S.t.   EYALRRDFPAVDGTSRLSASLATGGLSPRQCLHRLA-EQPQALDGC--PGSV-WLNELIWRE
phr N.c.   KYAERRNIPAMQGTSNLSVHFASGTLSARTAIRTARDRNNTKKLNGG--NEGIQRWISEVAMRD
phr S.c.   KYNNEKDMLYLGGISNLSVYITTGRISTRLIVNQAF-QSCNGQIMSKALKDNSSTQNFIKEVAMRD
phr H.h.   RYEDRRDYPHEEPTSRLSPHLKFGTIGIRTVYEAARAAKSDADTDDE--RENVAAFIGQLAWRE
phr A.n.   DYDPQRNFPAEAGTSGLSPALKFCAIGIRQAWQAASAAHALSRSDEA--RNSIRVWQQELAWRE
phr S.g.   DYEDGHDDLAGDATSRLSPHLHFGTVSAAELVHRAR-------EKG---GLGGEAFVRQLAWRD
```

| FIG. 4A | FIG. 4B |
|---------|---------|
| FIG. 4C | FIG. 4D |
| FIG. 4E | FIG. 4F |

```
PELSRLPTDWIHHPWNAPESVLQAAGI----ELGSNYPLPIVGLDEAKARLHEALSQMWQLEAASRAAIENGSEE  508
PELRDVP-------GKVVHEPWKWA----QKAGVTLDYPQPIVEHKEARVQTLAAYEAARKGK           ****  472
PALRDIP-------GKAIHEPWRWA----EKAGVVLDYPRPIVEHKQARIATLSAYEAARKGA           ****  473
EELRDLPELKGGGEIHDPYGRGSEKVKKLEEKGYPRPIVEHSGARDRALDAYKRGLARDL              ****  ...
PEL----------------------ISSENKRPENYPKPLVDLKHSRERALKVYKDAM                ****  565
PELRDVPADAIHSWHEL---------SLSERRRHAPEYPQPIVDHSQRREDAIAMFERARGDL           ****  484
PELRHVHPKDLIS-GEI---------TPIERR---GYPAPIVNHNLRQKQFKAMFERARGDL            ****  481
PELAEVEGSAIHEPWKLQGL------DRAGLDYPDPVVDLAEAR----ARFERARGLD                ****  455

DSRAEVPRNMVNTNQAQQRRAEPASNQVTAMIPEFNIRIVAESTEDSTAESSSSGRRERSGGIVPEWSPGYSEQF  648

681
```

*FIG. 4D* hy4   LPELSRLPTDWIHHPWNAPESVLQAAGIELGSNYPLPIVGLDEAKARLHEALSQMWQLEAASRAAIENGSEEGLG
trop A LEELHK-AEDSLAA-DETAAKAEADVASLNRRIQLVEEELDRAQERLATALQKLEEAEKAADES-ERG-MKVIE hy4   EVPRNMVNTNQAQQRRAEPASNQVTAMIPEFNIRIVAESTEDSTAESSSSGRRERSGGIVPEWSPGYSEQFPSEE
trop A TVTNNL-KSLEAQAEKYSQKEDKYEEEIKVLSDK-LKE-AETR-AEFAERSVTKLEKSIDDLEEKVAHAKEENLS

FIG. 4E

```
                          hy4-3  *       ↓ hy4-2 (T-DNA)
DSAEVEEAPIEFPRDITMEETEPTRLNPNRRYED--QMVPSITSSLIRPEEDEESLNLRNSVGDSRA  577
SRAQKDEKMEI-QEIQLKEAKHIAEDADRKYEEVARKLVIIESDLERAEERAELSEGKCAELEEELK  199

NRIGGSITSSYLDNHHEILNWRRLSQTG  681
MHQMLHQILLE-LNNM            284
```

FIG. 4F

Partial DNA Sequence of Rice HY4 Gene
(R2)

```
GGATCCCCCGGGCTGCAGGAATTCGGCACGAGGAGATGATGGCAGCGGAGGGCATCATCG
TGCAGTCTTTCAATGCAGACCTGCTGTACGAGCCGTGGGAAGTTGTCGACGACGAAGGCC
AATCTTTCACCATGTTTGCGCCTTTCTGGAATAGGTGCCTCAGCATGCCGTATGATCCTG
CCGCACCGCTGTTGCCTCCTAAGAGAATCAATTCAGGTGACTTATCAATGTGCCCATCAG
ATGATCTGATCTTTGAGGATGACTCGGAGAGGGGAAGCAATGCACTTCTTGCCCGAGCAT
GGTCACCAGGCTGGCAGAATGCAGACAAGGCACTGACAGCTTTCCTGAATGGTCCTTTGA
TCCACTACTCAGTGAATCGCAAGAAAGCAGACAGTGCAAGTACCTCCTCTTATCACCGT
ACCTGCATTTCGGTGAGCTGAGTGTGCGCAAGGTCTTCCACCTTGTTCGGATGAAGCAGC
TTGTGTGGAGCAATGAGGGCAATCGTGCAGCTGAAGAGAGCTGCACCCTGTTCTTCGGTC
CATTGGTCTCCGGGTCGTACTCACGGTATCTGAGTTTCAACCACCCATGCAGCCATGAGA
AGCCCCTTTTGGCACACCTCAGGTTCTTCCCCTGGGTGATCAATGAGTGCTACTTCAAGA
TATGGCGGCAGGGAAGGACTGGTTACCCCCTTGTTGATGCCGGCATGAGGGAGCTATGGG
CTACAGGGTGGTTGCATGATCGTATTCGTGTGGTAGTGTCAAGTTTCTTCGTCAAAGTCC
TTCAACTACCATGGCGATGGGGATGAAGTACTTTTGGGACACATTATTAGACGCAGATC
TTGAGAGCGATGCACTAGGCTGGCAGTATATCTCTGGCTCTCTTCCTGATGGCCGAGAACT
TGACCGCATTGACAATCCTCAGCTCGAAGGCTACAAGTTTGATCCGCATGGTGAGTATGT
CCGAAGGTGGCTTCCGGAGCTTGCAAGGTTGCCAACAGAATGGATACACCATCCATGGA
TGCACCCGCATCTGTGCTGCAAGCTGCAGGAGTCGAGTTAGGCTCCAACTACCCTCTCCC
TATAGTTGGGCTAGATGCAGCCAACGCCAGGCTGCAAGAAGCCCTGTCAGAAATGTGGCA
GCTTGAGGCAGCATCCAGGGCCGCAATGGACAATGGAATGGAAGAAGGCCTTGGCGACTC
CTCGGAGGTTCCACCAATTGAATTTCCTCGAGAACTACAGATGGAAGTTGACCGAGAACC
AGCTCGAGTAACAGCCAATGTGCTGACAACAGCTCGAAGACGCGAGGATCAGATGGTGCC
AACAATGACATCTTCACTAAACAGGGCTGAAACTGAGATTTCTGCCGATTTTATGAACAG
TGTGGACAGTAGGGCAGAGGTACCAACCCGTGTGAATTTTGAGCCTGCAACTGAGCGGGA
AGAAAATTTCCGTACCACTGCGGGAAATGTTGCTAGAACAAATGGTATTCATGAGCACAA
TAATTTCCAGCAACCTCAGCACCGTATGCGAAATGTTCTAGCACCATCTGTATCAGAGGC
ATCAAGTGGCTGGACTGGGAGAGAGGGAGGCGTAGTCCCAGTTTGGTCGCCTCCTGCAGC
ATCAGACCATTCAGAAACTTTTGCCTCTGATGAAGCTGACATTTCTAGTAGGAGTTATTT
GGATAGGCATCCACAGTCGCACCGGTTGATGAACTGGAGTCAATTATCCCAGTCATTGTT
GAGTTCAGATGCACGGACAACAAGGTCGGGGAAGTGGAAAATTCCATGCAACCAAATTGG
ATCGGTTAGGGTTTTCTCCGCCCCAGATTCATATGTAAATTGTCCACCTATGTGCTTATC
TATAGTCTGATGAGCATGCAAGCCAGGCAATTCTGAGTGTGACAATAGTTGTGTAATCTA
TCNTGTAGACTATCTGTTGGTCAACAGATTGTAGAGTGCTGAACTGGATATGTATAC
```

FIGURE 7a

Partial Amino Acid Sequence of Rice HY4 (R2)

IPRAAGIRHEEMMAAEGIIVQSFNADLLYEPWEVVDDEGQSFTMFAPFWNRCLSMPYDPA
APLLPPKRINSGDLSMCPSDDLIFEDDSERGSNALLARAWSPGWQNADKALTAFLNGPLI
HYSVNRKKADSASTSLLSPYLHFGELSVRKVFHLVRMKQLVWSNEGNRAAEESCTLFFGP
LVSGSYSRYLSFNHPCSHEKPLLAHLRFFPWVINECYFKIWRQGRTGYPLVDAGMRELWA
TGWLHDRIRVVVSSFFVKVLQLPWRWGMKYFWDTLLDADLESDALGWQYISGSLPDGREL
DRIDNPQLEGYKFDPHGEYVRRWLPELARLPTEWIHHPWDAPASVLQAAGVELGSNYPLP
IVGLDAANARLQEALSEMWQLEAASRAAMDNGMEEGLGDSSEVPPIEFPRELQMEVDREP
ARVTANVLTTARRREDQMVPTMTSSLNRAETEISADFMNSVDSRAEVPTRVNFEPATERE
ENFRTTAGNVARTNGIHEHNNFQQPQHRMRNVLAPSVSEASSGWTGREGGVVPVWSPPAA
SDHSETFASDEADISSRSYLDRHPQSHRLMNWSQLSQSLLSSDARTTRSGKWKIPCNQIG
SVRVFSAPDSYVNCPPMCLSIV**ACKPGNSECDNSCVIYXVDYLLVNRL*SAELDMY

FIGURE 7b

Partial DNA sequence of Pea HY4 gene:
(C3)
GGTGATAATCCACAGTTTGAGGGATACAAATGTGATCCAAACGGAGAATA
TGTGCGACGCTGGCTACCGGAACTTGCAAGACTACCGACTGAATGGATACAT
CATCCTTGGAATGCACCAGAATCAGTTCTCCAAGCTGCAGGTATTGAACTA
GGCTCAAACTACCCTCTTCCGATTGTGGAAATAGATGCAGCAACAGTGAGA
CTAGAAGAAGCACTTATTCAAATGTGGCAACTAGAAGCAGCTTCAAGAAC
TGCAGCCGAAAACGGAACCGAAGAAGGTCTCGGAGACTCGACTGAATCCGC
CCCTATTGCGTTTCCTCAAGACATACAAATGGAGGAAAGACACGAACCGGT
TAGGAACAATCCACCTCATGGTACTCGGCGCTACCAGGAAGAAATGGTACC
TAGTAGTACTTACTCTAGAGTGAGAGTGGAAGATGAAGAAACTTCTNNNN
TTCGAAACTCGGCGGAGACAGCCGAGCTGAAGTACCAACAAATGCAAATA
CACAGCAAAATGGACGGGAACCAATGGACCAAGGAATGTTGCAGAATGTA
AATAGAAACACTAGACAACGACGTAAT FIGURE 7c Partial amino acid sequence of Pea HY4
(C3)
GDNPQFEGYKCDPNGEYVRRWLPELARLPTEWIHHPWNAPESVLQAAGIEL
GSNYPLPIVEIDAATVRLEEALIQMWQLEAASRTAAENGTEEGLGDSTESAP
IAFPQDIQMEERHEPVRNNPPHGTRRYQEEMVPSSTYSRVRVEDEETSXXRNS
AETAELKYQQMQIHSKMDGNQWTKECCRMXIETLDNDV (Sequence similarity to Arabidopsis HY4 is89%)

FIGURE 7d

DNA Sequence for Arabidopsis Gene CRY2

```
CGCCGCTCTAGAACTAGTGGATCCCCCGGGCTGCAGGAATTCGCGGCCGCCACAGTCTTT
GATTCGAAGATCTTTGTCGCCGAGAGATAGCCACTCTGATTTGAGTTCTGAACTATTCTC
TGGAGGAGGTTGAGGTCTGAAATCATGGAACAACTTGGTTAGAGTGTGGAATTTTAGCTG
ATTTGATCTTTGATTCATCTGTGATCATAATAACTATGAAGATGGACAAAAAGACTATAG
TTTGGTTTAGAAGAGACCTAAGGATTGAGGATAATCCTGCATTAGCAGCAGCTGCTCACG
AAGGATCTGTTTTCCTGTCTTCATTTGGTGTCCTGAAGAAGAAGGACAGTTTATCCTGGA
AGAGCTTCAAGAGGTGGATGAAACAATCACTTGCTCACTTATCTCAATCCTTGAAGGCTC
TTGGATCTGACCTCACTTTAATCAAAACCCACAACACGATTTCAGCGATCTTGGATTGTA
TCCGCGTTACCGGTGCTACAAAAGTCGTCTTTAACCACCTCTATGATCCTGTTTCGTTAG
TTCGGGACCATACCGTAAAGGAGAAGCTGGTGGAACGTGGGATCTCTGTGCAAAGCTACA
ATGGAGATCTATTGTATGAACCGTGGGAGATATACTGCGAAAGGGCAAACCTTTTACGA
GTTTCAATTCTTACTGGAAGAAATGCTTAGATATGTCGATTGAATCCGTTATGCTTCCTC
CTCCTTGGCGGTTGATGCCAATAACTGCAGCGGCTGAAGCGATTTGGGCGTGTTCGATTG
AAGAACTAGGGCTGGAGAATGAGGCCGAGAAACCGAGCAATGCGTTGTTAACTAGAGCTT
GGTCTCCAGGATGGAGCAATGCTGATAGGTTACTAAATGAGTTCATCGAGAAGCAGTTGAT
AGATTATGCAAAGAACAGCAAGAAAGTTGTTGGGAATTCTACTTCACTACTTTCTCCGTA
TCTCCATTTCGGGGAAATAAGCGTCAGACACGTTTTCCAGTGTGCCCGGATGAAACAAAT
TATATGGGCAAGAGATAAGAACAGTGAAGGAGAAGAAAGTGCAGATCTTTTTCTTAGGGG
AATCGGTTTAAGAGAGTATTCTCGGTATATATGTTTCAACTTCCCGTTTACTCACGAGCA
ATCGTTGTTGAGTCATCTTCGGTTTTTCCCTTGGGATGCTGATGTTGATAAGTTCAAGGC
CTGGAGACAAGGCAGGACCGGTTATCCGTTGGTGGATGCCGGAATGAGAGAGCTTTGGGC
TACCGGATGGATGCATAACAGAATAAGAGTGATTGTTTCAAGCTTTGCTGTGAAGTTTCT
TCTCCTTCCATGGAAATGGGGAATGAAGTATTTCTGGGATACACTTTTGGATGCTGATTT
GGAATGTGACATCCTTGGCTGGCAGTATATCTCTGGGAGTATCCCCGATGGCCACGAGCT
TGATCGCTTGGACAATCCCGCGTTACAAGGCGCCAAATATGACCCAGAAGGTGAGTACAT
AAGGCAATGGCTTCCCGAGCTTGCAGGATTGCCAACTGAATGGATCCATCATCCATGGGA
CGCTCCTTTAACCGTACTCAAAGCTTCTGGTGTGGAACTCGGAACAAACTATGCGAAACC
CATTGTAGACATCGACACAGCTCGTGAGCTACTAGCTAAAGCTATTTCAAGAACCCGTGA
AGCACAGATCATGATCGGAGCAGCACCTGATGAGATTGTAGCAGATAGCTTCGAGGCCTT
AGGGGCTAATACCATTAAAGAACCTGGTCTTTGCCCATCTGTGTCTTCTAATGACCAACA
AGTACCTTCGGCTGTTCGTTACAACGGGTCAAAGAGAGTGAAACCTGAGGAAGAAGAAGA
GAGAGACATGGAGAAÅTCTAGGGGATTCGATGAAAGGGAGTTGTTTTCGACTGCTGAATC
TTCTTCTTCTTCGGAGTGTGTTTTCGTTTCGCAGTCTTGCTCGTTGGCATCAGAAGGGA
AGAATCTGGAAGGTATTCAAGATTCATCTGATCAGATTACTACAAGTTTGGGAAAAAATG
GTTGCAAATGATCAAAATAATGTGCTGTTATAAAGCCTAACATGTAGATGTGTGAATGTG
TCTTTTAACTCTTTGTTTCCTTTTGGTTATACTCAAAAGGATATGATTGGCGCGCGAATT
CGATATCAAGCTTATCGATACCGTCGACCTCGAGGGGGG
```

FIGURE 9b

Amino Acid Sequence of CRY2

MKMDKKTIVWFRRDLRIEDNPALAAAAHEGSVFLSSFGVLKKKDSLSWKSFKRWMKQSLAHLSQSLKALGSDLTL
IKTHNTISAILDCIRVTGATKVVFNHLYDPVSLVRDHTVKEKLVERGISVQSYNGDLLYEPWEIYCEKGKPFTSF
NSYWKKCLDMSIESVMLPPPWRLMPITAAAEAIWACSIEELGLENEAEKPSNALLTRAWSPGWSNADRLLNEFIE
KQLIDYAKNSKKVVGNSTSLLSPYLHFGEISVRHVFQCARMKQIIWARDKNSEGEESADLFLRGIGLREYSRYICF
NFPFTHEQSLLSHLRFFPWDADVDKFKAWRQGRTGYPLVDAGMRELWATGWMHNRIRVIVSSFAVKFLLLPWKWG
MKYFWDTLLDADLECDILGWQYISGSIPDGHELDRLDNPALQGAKYDPEGEYIRQWLPELAGLPTEWIHHPWDAP
LTVLKASGVELGTNYAKPIVDIDTARELLAKAISRTREAQIMIGAAPDEIVADSFEALGANTIKEPGLCPSVSSN
DQQVPSAVRYNGSKRVKPEEEEERDMEKSRGFDERELFSTAESSSSSECVFRFAVLLVGIRREESGRYSRFI*

FIGURE 9c

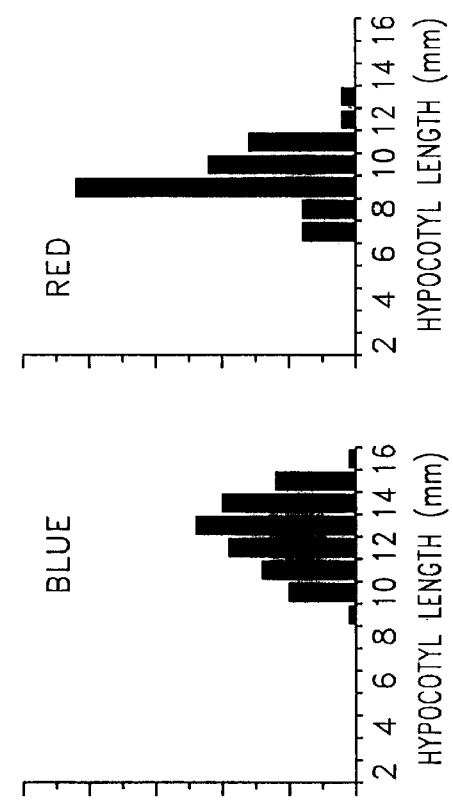
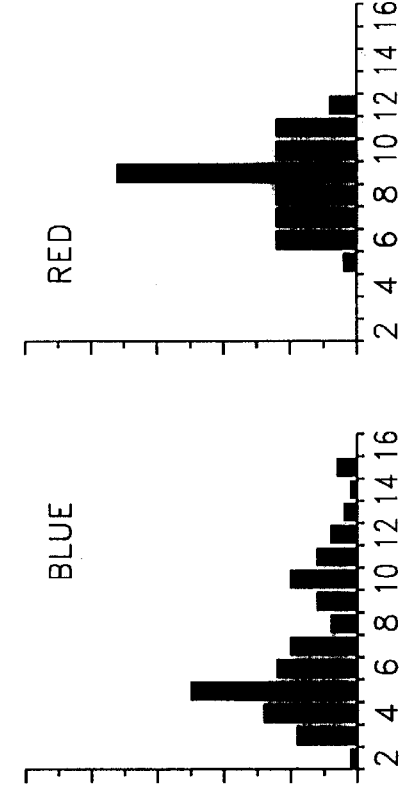
FIG. 17A  FIG. 17B  FIG. 17C  FIG. 17D
FIG. 17E  FIG. 17F  FIG. 17G  FIG. 17H

BLUE LIGHT PHOTORECEPTORS AND METHODS OF USING THE SAME

Portions of this invention were made with US Government support (Grant No. GM38409—NIH; DE FG02 87ER1680—DOE; and, 92-37304-7937—USDA). The US Government may therefore have certain rights in the invention.

The field of the invention is blue light/UV-A photoreceptor-mediated responses in biological systems.

BACKGROUND OF THE INVENTION

Many different wavelengths of light provide signals by which both eukaryotes and prokaryotes exist within and respond to their respective environments. The ability of a cell to sense a particular wavelength of light is mediated by specific photoreceptors such as rhodopsin, chlorophyll, phytochrome, cryptochrome and even photoreactivating enzymes. Some of these receptors, excluding the cryptochrome and blue light receptors, have been cloned and characterized.

Blue light responses have been characterized in a variety of organisms. For example, in fungi, in particular in Phycomyces and Neurospora, blue light serves as a major developmental stimulus in both sexual and asexual reproduction (Corrochano et al., 1992, TIG 8:278; Degli-Innocenti et al., 1984, Genetic analysis of blue light-induced responses in *Neurospora crassa*. In: Blue light effects in biological systems. H. Senger. p213–227. Berlin: Springer-Verlag). Mutants have been characterized in organisms which are defective in their ability to sense blue light, which mutants have defined multiple loci with similar phenotypes suggesting the existence of a multi-step signal transduction pathway. However, the nature of the blue light-sensitive photoreceptor in these organisms is unknown.

Animals are also capable of sensing blue light, which sensing provides a means of entrainment of behavioral circadian rhythms in flies and in mammals (Truman, 1976, Photochem. Photobiol 23:215; Foster et al., 1993, J. Biological Rhythms 8:S17–23) This light sensing mechanism in both flies and in mammals is distinct from that associated with the visual process in that blind flies and mammals continue to exhibit rhythm entrainment in response to blue light. In insects, this photoreception is extraretinal and is associated with the cerebral lobe region of the brain. In humans, blue light photoreception resides in the eye in parallel with the vision system.

Phototropic blue light responses in plants have also been studied (Konjevic et al., 1989, Proc. Natl. Acad. Sci. USA 86:9876; Khurana and Poff, 1989, Planta. 178:400; Khurana et al., 1989, Plant Physiol. 91:685). In addition, stem or hypocotyl elongation in plants is inhibited by light. Studies conducted in Arabidopsis describe a class of mutants which differ from each other according to their insensitivity to either red, far red, or blue light (Koornneef et al., 1980, Pflanzenphysiol. Bd. 100:147). Hypocotyl elongation is inhibited in a series of mutants termed blu and hy4 when such mutants are exposed to UVA light, but elongation is not inhibited when these mutants are exposed to blue light (Ahmad and Cashmore, 1993, Nature 366:162; Koornneef et al., 1980, Pflanzenphysiol. Bd. 100:147; Liscum and Hangarter, 1991, Plant Cell. 3:685).

Control of stomatal opening represents another blue light response in plants (Assmann et al., 1985, Nature 318:285; Poole, 1993, Proc. Natl. Acad. Sci. USA 90:3125; Shimazaki et al., 1992, Plant Physiol. 99:1416). Similar to the situation in hypocotyl elongation, this response is coupled tightly to changes in membrane polarization. For example, a single pulse of blue light results in hyperpolarization of guard cell membranes thereby effecting opening of voltage-gated potassium channels which in turn effects opening of the stomata.

Expression of nuclear genes associated with the photosynthetic process is frequently mediated by blue light via a photoreceptor which is distinct from phytochrome (Warpeha and Kaufman, 1990, Planta. 182:553; Warpeha et al., 1989, Plant Physiol. 91:1030). In addition, a blue light-activated heterotrimeric G protein has been discovered to be associated with the plasma membrane of pea apical buds (Warpeha et al., 1991, Proc. Natl. Acad. Sci. USA 88:8925; Warpeha et al., 1992, Photochem. Photobiol. 55:595) which exhibits blue light (but not red light)-dependent GTPase activity. This G protein may be a component in the signal transduction step between a blue light photoreceptor and gene expression. Blue light-induced protein kinase activity has been described in the plasma membrane of stem cells from corn and from Arabidopsis (Gallagher et al., 1988, Proc. Natl. Acad. Sci. USA 85:8003; Hager and Brich, 1993, Planta. 189:657; Hager et al., 1993, 190:120; Reymond et al., 1992, Plant Physiol. 100:655; Short and Briggs, 1990, Plant Physiol. 92:179). Further, blue light-induced absorbance changes have been observed in membrane fractions from a variety of plants including corn (Leong et al., 1981, Photochem. Photobiol. 34:697), Phycomyces and Dictyostelium (Poff and Buler, 1974, Nature 248:799) and Neurospora (Munoz and Butler, 1975, Plant Physiol. 55:421).

In addition to plants, animals and fungi, blue light-responsive molecules are known in bacteria and in particular, microbial photolyases are known to be blue light photoreceptors. Although it is believed that plant blue light responses are mediated by flavoproteins, and microbial photolyases are also flavoproteins, not all blue light-sensitive flavoproteins are photolyases. Rather, as flavoproteins, photolyases represent a rare class of enzymes whose activity is strictly dependent on the absorption of light.

Within the present invention there is described a heretofore unknown gene, HY4, encoding a blue light photoreceptor in plants, which receptor regulates stem length in plants. The discovery of this gene and manipulation of same, permits the generation of transgenic plants, which plants have significant advantages over their nontransgenic substantially homozygous counterparts.

SUMMARY OF THE INVENTION

The invention features compositions and methods for producing transgenic plants, which plants have shorter or longer stem lengths than substantially homozygous nontransgenic plants.

Accordingly, in one aspect, the invention features a substantially pure preparation of a nucleic acid specifying the sequence of a HY4 gene and a substantially pure preparation of a nucleic acid encoding a HY4 polypeptide. The nucleic acid of the invention is preferably Arabidopsis HY4, *Oryza sativa* HY4, or *Pisum sativum* HY4.

A "substantially pure preparation of a nucleic acid", as used herein, refers to a nucleic acid sequence which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., RNA, DNA or protein) in its natural state.

The invention further features a recombinant vector and a recombinant cell comprising a HY4 nucleic acid.

In another aspect, the invention features a transgenic plant, the cells and the seeds of the plant comprising a HY4 nucleic acid. The stem of the transgenic plant is shorter than the stem of a nontransgenic but otherwise substantially homozygous wild type plant. By the term "nontransgenic but otherwise substantially homozygous wild type plant" is meant a nontransgenic plant from which the transgenic plant was generated. Preferably, the transgenic plant is one of Oryza sativa, Avena spp, Triticum spp, Hordeum vulgare, Saccharum spp, Zea mays, Secale cereale, Glycine max, Lycopersicon esculentum or Zea mays and Sorghum bicolor.

In yet another aspect of the invention, there is provided a substantially pure preparation of a HY4 polypeptide and an antibody directed against HY4, which antibody is specific for either the N-terminal or the C-terminal portion of HY4. As used herein, the term "substantially pure" describes a compound, e.g., a protein or polypeptide, which has been separated from components which naturally accompany it. Typically, a compound is substantially pure when at least 10%, more preferably at least 20%, more preferably at least 50%, more preferably at least 60%, even more preferably at least 75%, more preferably at least 90%, and most preferably at least 99% of the total material (by volume, by wet or dry weight, or by mole per cent or mole fraction) of a sample is the compound of interest. Purity can be measured by any appropriate method, e.g., by column chromatography, polyacrylamide gel electrophoresis, or by HPLC analysis. A compound, e.g., a protein, is substantially purified when it is essentially free of naturally associated components or when it is separated from the native compounds which accompany it in its natural state.

In yet another aspect of the invention, there is provided a method of generating a transgenic plant, wherein the plant comprises a shorter stem than an otherwise substantially homozygous wild type plant. The method involves introducing into the cells of the transgenic plant an HY4 gene, wherein expression of said HY4 gene mediates growth of the shorter stem.

The invention further features a substantially pure preparation of a nucleic acid complementary to a portion or all of a HY4 gene, wherein the nucleic acid is capable of inhibiting expression of the HY4 gene when introduced into cells comprising the HY4 gene. The nucleic acid is complementary to either a portion or all of a HY4 gene, which gene is preferably Arabidopsis HY4, Oryza sativa HY4, or Pisum sativum HY4. By complementary to a portion or all of a HY4 gene is meant a sequence of nucleic acid which does not encode HY4 protein. Rather, the sequence which is being expressed in the cells is identical to the non-coding strand of the HY4 gene and thus, does not encode HY4.

In addition, there is featured in the invention a recombinant vector comprising a complementary HY4 nucleic acid, a recombinant cell comprising a complementary HY4 nucleic acid, and a transgenic plant comprising a complementary HY4 nucleic acid, the stem of which plant being longer than the stem of a nontransgenic but otherwise substantially homozygous wild type plant.

Complementary as used herein also refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

In yet another aspect of the invention, there is provided a method of inhibiting expression of HY4 in a cell comprising introducing into said cell a nucleic acid complementary to all or a portion of a HY4 gene.

The invention further features a method of generating a transgenic plant comprising a longer stem than an otherwise substantially homozygous wild type plant. The method involves introducing into the cells of the transgenic plant a nucleic acid complementary to an HY4 gene, wherein expression of the nucleic acid mediates growth of the longer stem. Preferably, the transgenic plant is selected from the group consisting of Camellia sinensis, Vitis spp, Gossypium spp, Pinus radiata and Populus tirichocarpa.

Also included in the invention is a substantially pure preparation of a nucleic acid specifying the sequence of a HY4 homolog and a HY4-related gene. Preferably, according to the invention, the HY4 homolog is either Oryza or Pisum sativum HY4, and the HY4-related gene is Arabidopsis CRY2.

By HY4 homolog is meant a HY4 gene in a species of plant, other than Arabidopsis, which is at least 70% homologous to the Arabidopsis HY4 gene in both the flavin and the non-flavin binding domain.

By HY4-related gene is meant a gene encoding a blue light/UV-A light photoreceptor which is a member of the HY4 family of genes. A HY4 related gene may be present in a cell which also encodes an HY4 gene. A HY4 related gene preferably is at least 70% homologous with respect to amino acid sequence in the flavin binding domain with the flavin binding domain of Arabidopsis HY4. A HY4 related gene may have at least 70% amino acid homology with Arabidopsis HY4 in their respective flavin binding domains and may also function as a blue light/UV-A photoreceptor, but not as a photolyase, or at least not exclusively as a photolyase.

As used herein, the term homologous refers to the subunit sequence similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are homologous at that position. The homology between two sequences is a direct function of the number of matching or homologous positions, e.g., if half (e.g., 5 positions in a polymer 10 subunits in length) of the positions in two polypeptide sequences are homologous then the two sequences are 50% homologous; if 70% of the positions, e.g., 7 out of 10, are matched or homologous, the two sequences share 70% homology. By way of example, the polypeptide sequences ACDEFG and ACDHIK share 50% homology.

BRIEF DESCRIPTION OF THE DRAWINGS

FIG. 2 depicts the results of Southern and Northern blot hybridization analysis of alleles of HY4.

FIG. 2c: The sequence extending into the third intron of HY4 is shown. Analysis of the end point of the deletion described in b above using Southern blot hybridization and Polymerase Chain Reaction (PCR) analysis revealed that the 3' intron splice junction and 3' untranslated region are absent in hy4-2.23N. The sequence of the unspliced intron was determined from the genomic sequence of hy4-2.23N and was found to extend the open reading frame to a putative polyadenylation site (underlined). The wild type DNA and amino acid sequences shown in FIG. 2c are designated SEQ ID NO:1 and 2, respectively; the DNA and amino acid sequence of 2.23N shown in this figure are designated SEQ ID NO:3 and 4 respectively.

FIG. 3A–3D is the DNA sequence [SEQ ID NO:5] of the HY4 gene and the putative amino acid sequence [SEQ ID NO:6] encoded by this gene. The nucleotide sequence of the longest of 10 cDNAs obtained from the same preparation of mRNA, isolated from a cDNA library of ectotype Columbia, was determined using the Sanger dideoxy sequencing protocol (Sanger et al., 1977, Proc. Natl. Acad. Sci. USA 74:5463) and an Applied Biosystems 370A automated DNA sequencer. The 5' and 3' ends of three additional cDNAs were also sequenced to confirm the locations of translation initiation and termination sites. The locations of the three introns was determined from the sequence of a genomic clone. Mutant alleles of HY4 were also characterized. PCR amplification of the coding sequence obtained from genomic DNA was performed in at least three independent reactions for each mutant. The products of this amplification were sequenced directly and mutations within the coding sequence were thus identified. Since identical nucleotide substitutions or deletions were found following each of the three independent reactions for each mutant, these deletions and substitutions represent bona fide mutations rather than artefacts. The locations and the nature of each of the mutations are as follows: hy4-1 and hy4-4 contain point mutations (the nucleotide and corresponding amino acid changes are indicated on the figure); the T-DNA insertion in hy4-2 is indicated and the 5 bp deletion in hy4-3 is underlined.

FIG. 4a is an amino acid sequence comparison between HY4 and photolyases. The amino acid sequence of HY4 [SEQ ID NO:9] was aligned with photolyases of short wavelength (*E. coli*, E.c. [SEQ ID NO:10]; *Salmonella typhimurium*; S.t. [SEQ ID NO:11]; *Neurospora crassa*, N.c. [SEQ ID NO:7]; *Saccharomyces cerevisiae*, S.c.) [SEQ ID NO:8] and of long wavelength (*Halobacterium halobium*, H.h. [SEQ ID NO:12]; *Anacystis nidulans*, A.n.; *Streptomyces griseus*, S.g.) types (Yasuhira and Yasui, 1992, J. Biol. Chem. 267:25644). Alignment was achieved using the PILE-UP program from GCG version 7-UNIX sequence analysis software (Higgins and Sharp, 1989, CABIOS 5:151). Amino acid identities between HY4 and any one of the photolyases genes are marked by grey shaded boxes. Amino acids which are conserved in HY4 and all seven photolyases are indicated by black boxes containing white lettering. Amino acids which are conserved in all seven photolyases but which are not present in HY4 are indicated by the clear boxes. Solid triangles depict those amino acids which are conserved among short wavelength photolyases within the first two thirds of the gene; open triangles depict those amino acids which are conserved among long wavelength photolyases. The locations of E. coli W227, W306, hy4-4 (G337-D) and hy4-1 (G340-E) mutations are indicated.

FIG. 4b–4f shows the amino acid sequence homology between the C-terminal domain of HY4 [SEQ ID NO:15] with rat smooth muscle tropomyosin A [SEQ ID NO:16] (Ruiz-Apazo and Nadai-Ginard, 1987, J. Biol. Chem. 262:4755). The alignment was conducted using a MacVector version 3.5 sequence analysis software package. Regions of homology are shaded; regions of identity are indicated by black boxes with white lettering. The positions of the C-terminal mutations in HY4 mutant alleles (hy4-2, hy4-3) are indicated. Whereas the C-terminal domain of HY4 does not appear to contain the extensive α-helix region predicted by the Chou-Fasman parameters for tropomyosin, there are small regions of predicted helicity throughout this region.

The domain structure of HY4 indicating the two domains of HY4 and the positions of the mutations is also shown. The location of the putative chromophore-binding domains is indicated; a 40 amino acid overlap between the region of photolyase homology and tropomyosin homology is indicated by the grey box. In the hy4-3 mutant the open reading frame stops at 8 amino acids downstream from the deletion.

Figure 5:
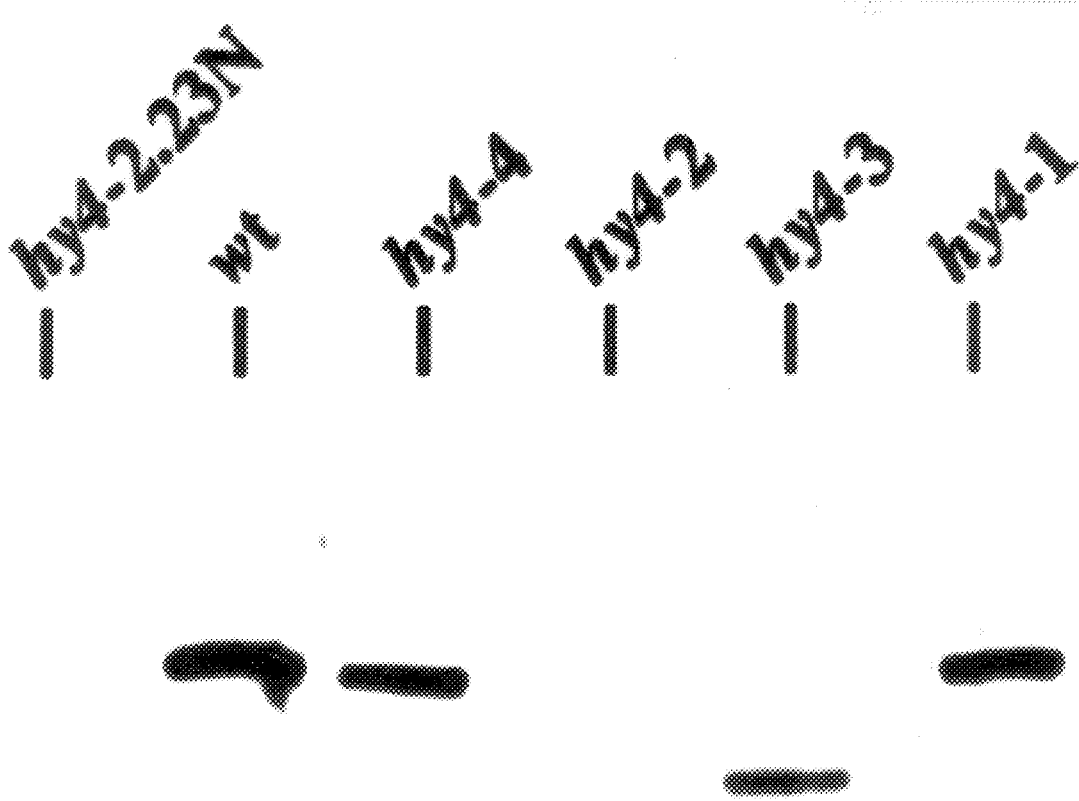

FIG. 5 is a photograph of an immunoblot of proteins obtained from various mutants of HY4 probed with antibody directed against HY4. The hy4 strains from which the proteins were obtained are indicated at the top of the figure.

Figure 6A:
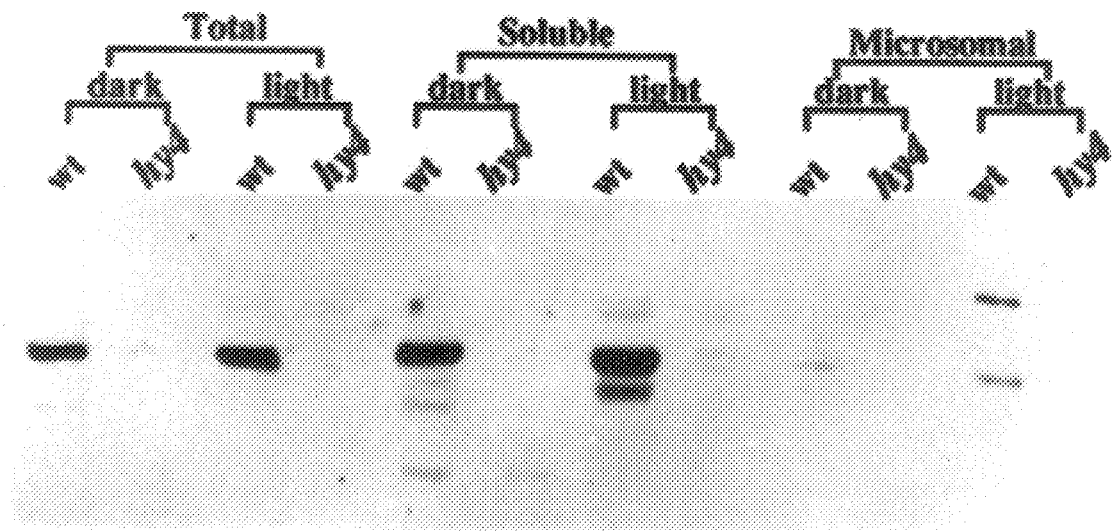
Figure 6B:
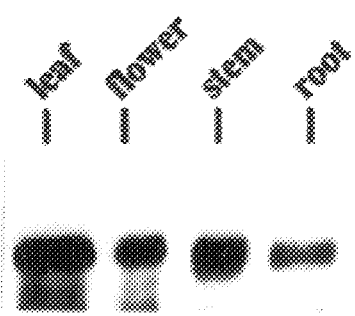

FIG. 6 is a photograph of an immunoblot showing that HY4 is a soluble protein in both light and dark grown seedlings (A) and that HY4 is found in all tissues of the plant (B). FIG. 6A Seven day old Arabidopsis wild type (wt) and hy4 mutant (hy4) seedlings grown in the dark (dark) or under white light (light) were homogenized in a buffer comprising 0.1M Tris, pH 7.5, 0.1M NaCl, 0.1% polyvinylpolypyrolidone (PVPP), 1 mM polymethylsulfonyl fluoride (PMSF) and 2 mM N-ethylmaleimide (NEM). The homogenate was then either boiled directly in SDS-PAGE sample buffer (Total), or was first centrifuged at 100,000×g for 30 minutes to separate the soluble (Solub.) and microsomal Micros.) fractions. Samples were electrophoresed through 10% SDS-PAGE, then transferred to nitrocellulose and incubated in the presence of antiserum to HY4 (⅕₀₀₀). Bound antibodies were visualized using horseradish peroxidase coupled to protein A. FIG. 6B Total proteins were obtained from three week old Arabidopsis leaf, stem, root and flower tissues and were assayed in a Western blot as described above.

FIG. 7 is the partial nucleotide and amino acid sequence of HY4 in Oryza sativa A and B, respectively) and Pisum sativum (C and D, respectively). [SEQ ID NOS:17,18,19, and 20 respectively].

Figure 8:
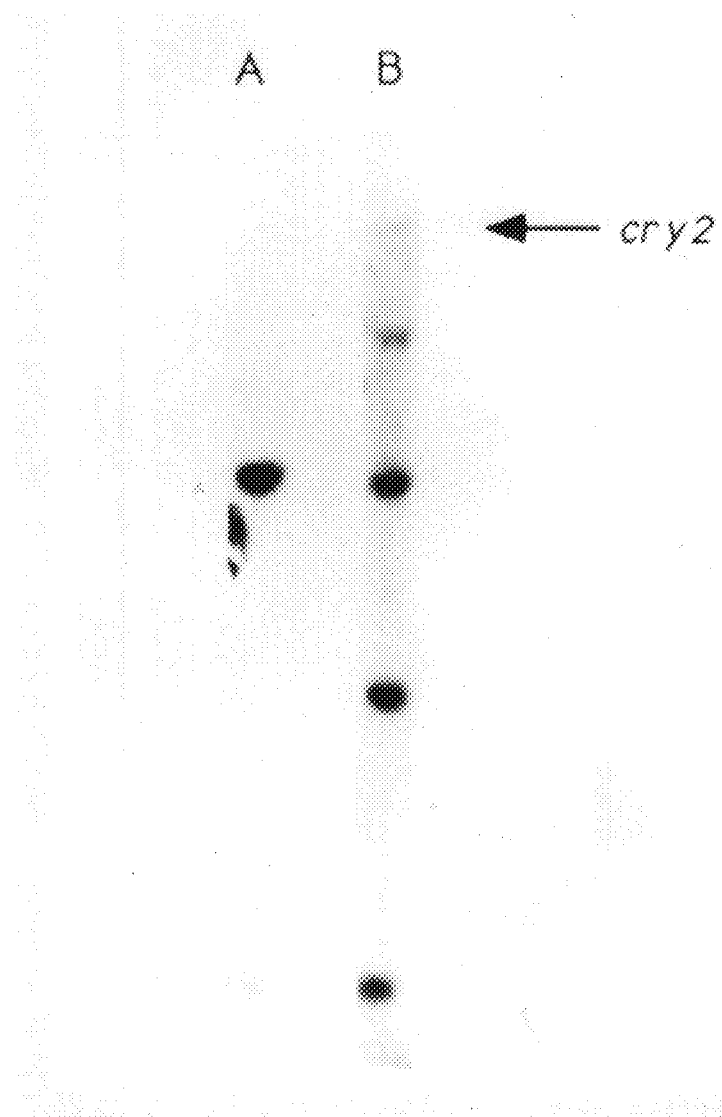

FIG. 8 is a photograph of a gel depicting that HY4 is a member of a small gene family. Southern blot hybridization was conducted on DNA obtained from Arabidopsis ectotype Col.GL. Each lane on the gel contains DNA digested with BamHI which was electrophoresed through a 0.7% agarose gel and transferred to nitrocellulose. Hybridization was carried out using a probe consisting of a 350 bp fragment of HY4 obtained from the flavin binding domain. In lane A, hybridization was carried out under high stringency conditions (5×SSPE, 50% formamide at 42° C. In lane B, hybridization was carried out under low stringency conditions (5×SSPE, 30% formamide at 42° C.). The additional bands present in B represent HY4 family members; the band corresponding to CRY2 is indicated.

Figure 9A:
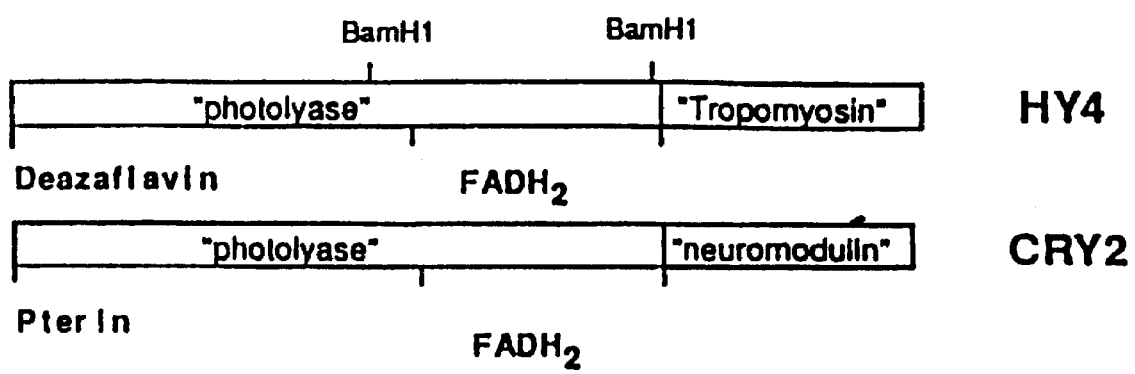

FIG. 9A is the structure of CRY2.

FIG. 9B is the nucleic acid sequence of CRY2.

FIG. 9C is the amino acid sequence of CRY2.

Figure 10:
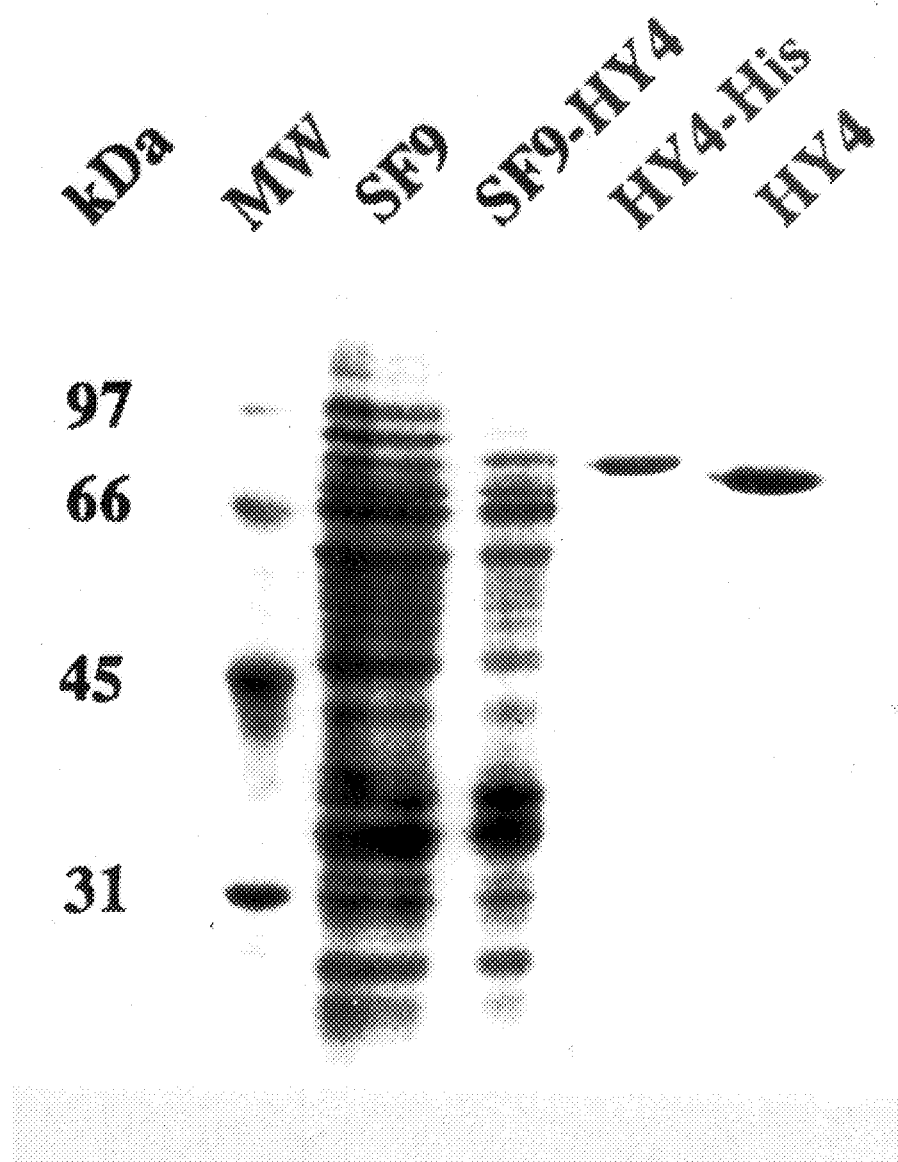

FIG. 10 is a photograph of a gel depicting expression and purification of HY4 protein. MW (molecular weight markers), SF9 (Stopdotera frugiperda cell lysate), SF9-HY4 (lysate of SF9 cells expressing HY4), HY4-His (purified HY4 recombinant protein), HY4 (HY4 protein further purified after the fusion portion was removed by thrombin cleavage).

Figure 11:
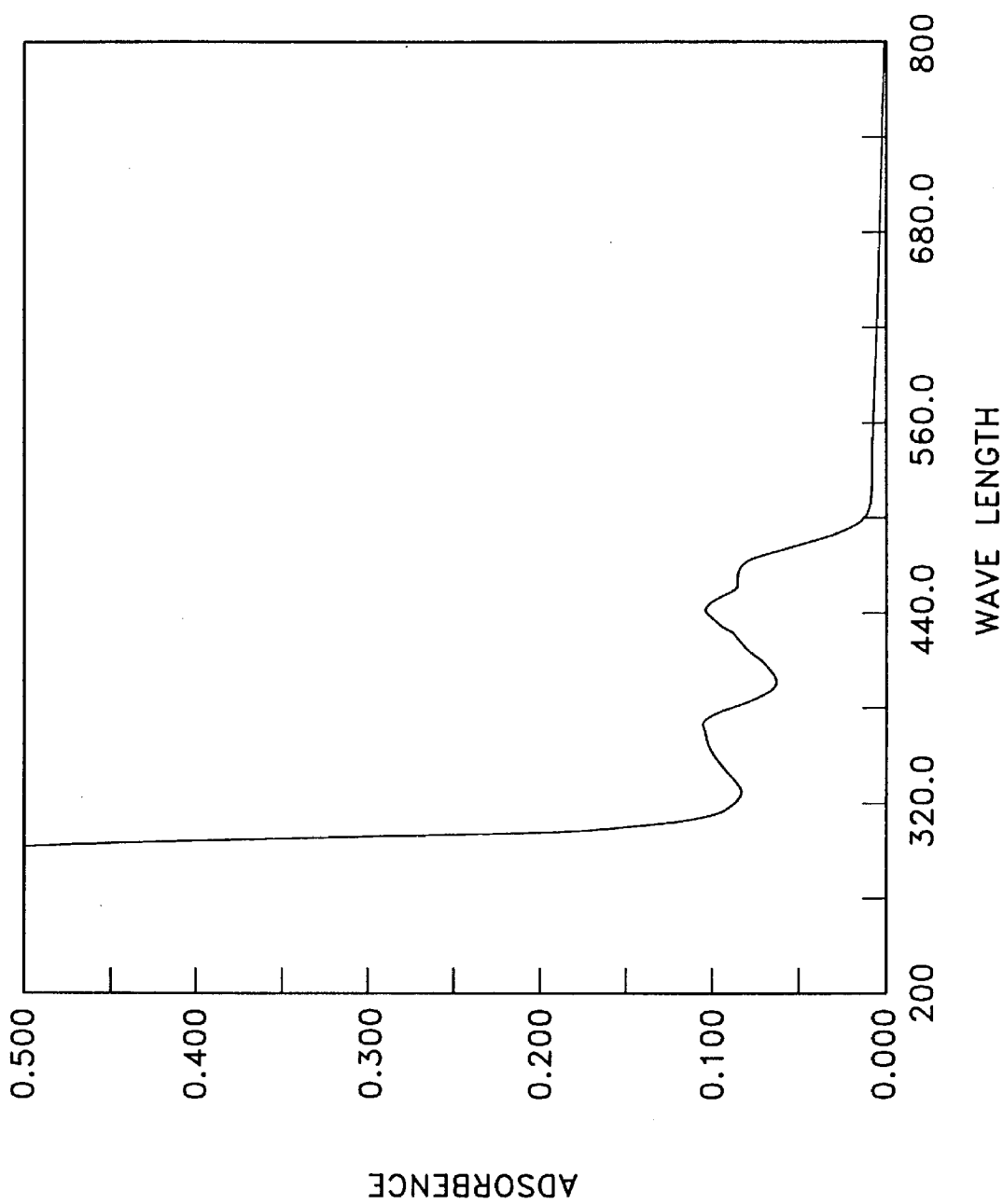

FIG. 11 is a graph depicting the absorbance spectrum of HY4 protein (2 mg/ml HY4 in 50 mM Tris, pH 7.5, 150 mM NaCl, 5 mM DTT, 1 mM EDTA). The absorption maxima are 445, 356, and 278 nm.

Figure 12:
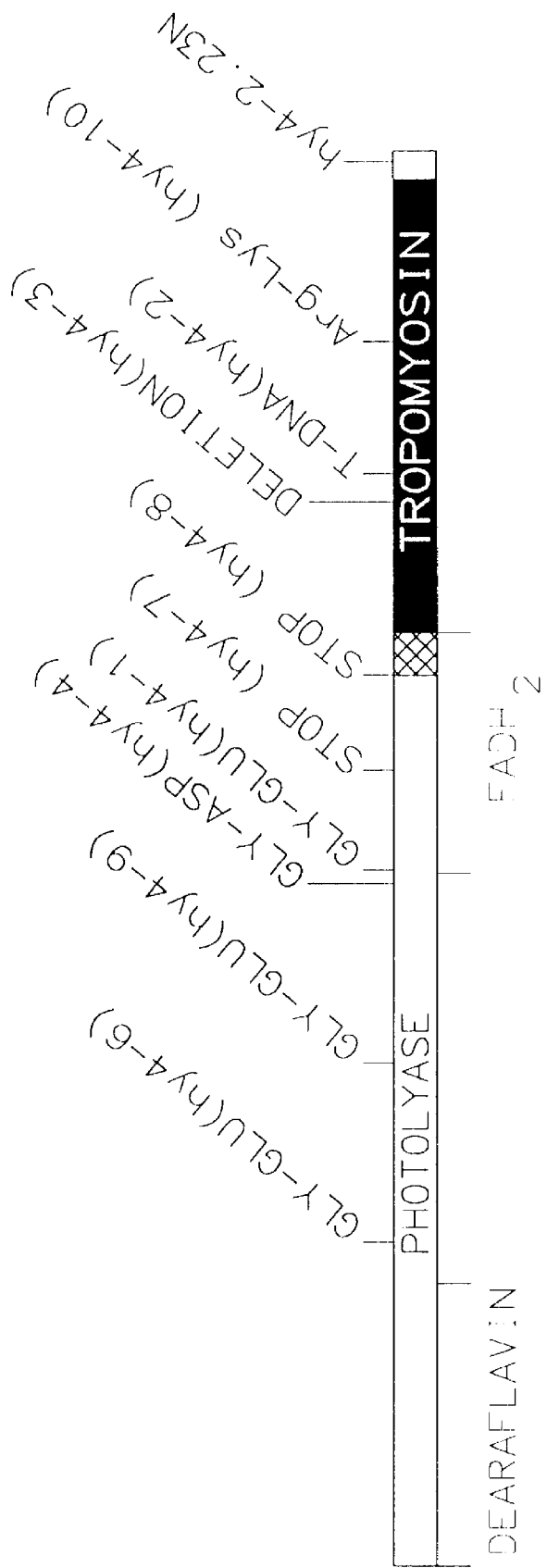

FIG. 12 is a diagram showing the relative positions of mutant alleles of HY4. The nature and position of the lesions are indicated for the different mutant alleles of HY4.

Figure 13:
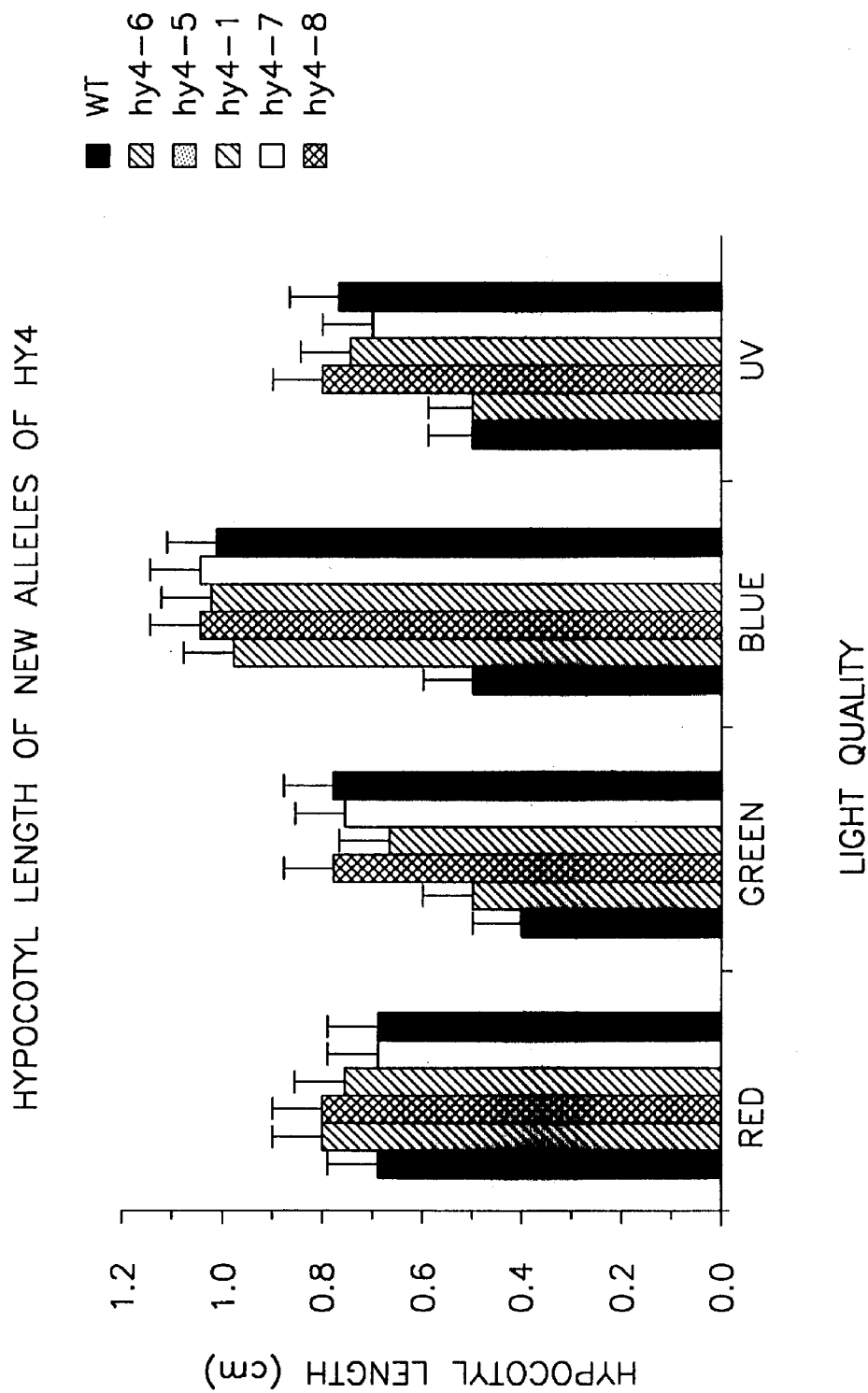

FIG. 13 is a graph depicting the hypocotyl lengths of five day old seedlings grown under the light conditions indicated on the graph.

Figure 14A:
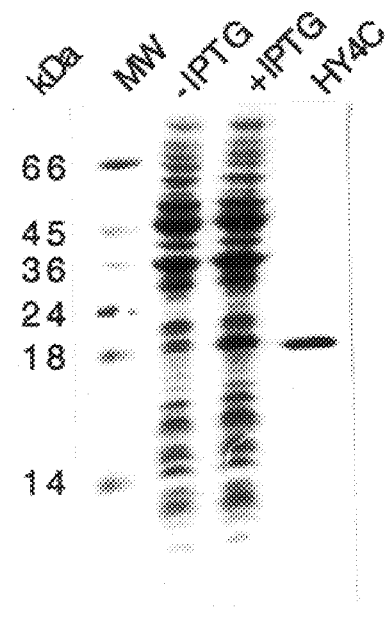
Figure 14B:
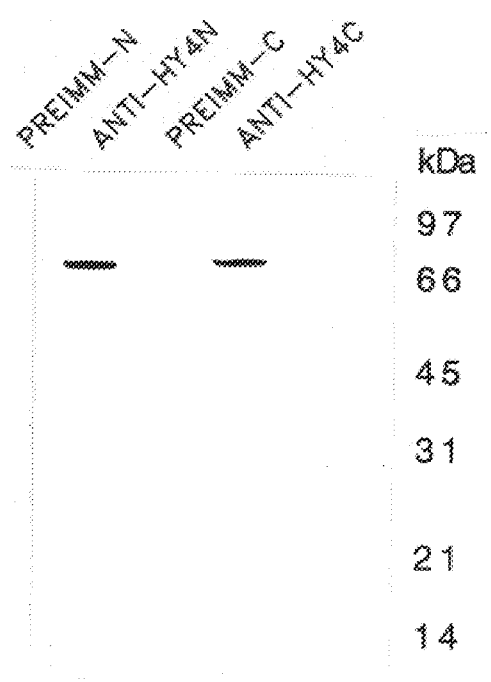

FIG. 14 is a photograph of a gel showing preparation of antibodies specific for HY4 protein. FIG. 14A shows purification of HY4C. Cultures of E. coli containing HY4C DNA were grown either in the presence or absence of IPTG and were electrophoresed in a Tricine SDS-polyacrylamide gel as indicated on the figure. Purified HY4C was also electrophoresed on this gel. Molecular weight markers were loaded and electrophoresed in the far lefthand lane. FIG. 14B HY4 cDNA was transcribed and translated in vitro. The in vitro translation product was immunoprecipitated with preimmune HY4C serum (preimm-C) or by antiserum raised against HY4C (anti-HY4C), or was immunoprecipitated with preimmune HY4 N-terminal serum (preimm-N) or by antiserum raised against the N-terminal portion of HY4 (anti-HY4N). Immunoprecipitated products were electrophoresed through a 10% SDS-polyacrylamide gel. Molecular weight markers were loaded and electrophoresed on the far righthand side of the gel and the remaining lanes were loaded as indicated on the figure.

Figure 15A:
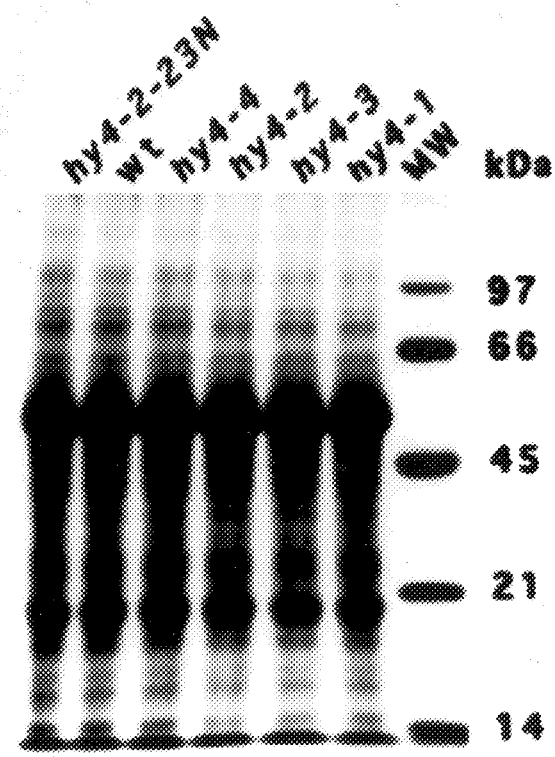
Figure 15B:
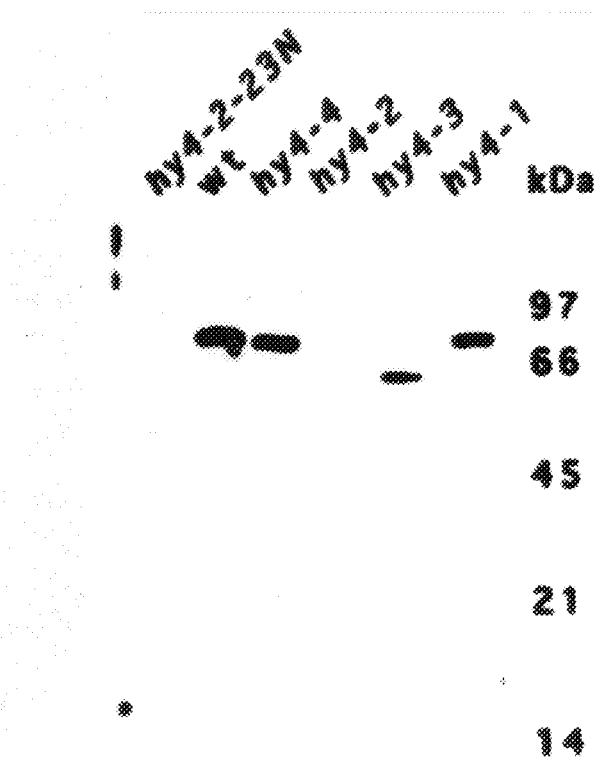

FIG. 15 is a photograph of a gel depicting reaction of anti-HY4C antibody with Arabidopsis HY4. FIG. 15A Total leaf proteins were extracted from wild type Arabidopsis (wt) or from hy4 mutant cell lines and were electrophoresed by SDS-PAGE as indicated on the figure. Electrophoresed proteins were visualized by coommassie blue staining. FIG. 15B Aliquots of the same protein samples as in A were examined by Western blot analysis using anti-HY4C IgG at a concentration of 26.6 ng/ml.

Figure 16:
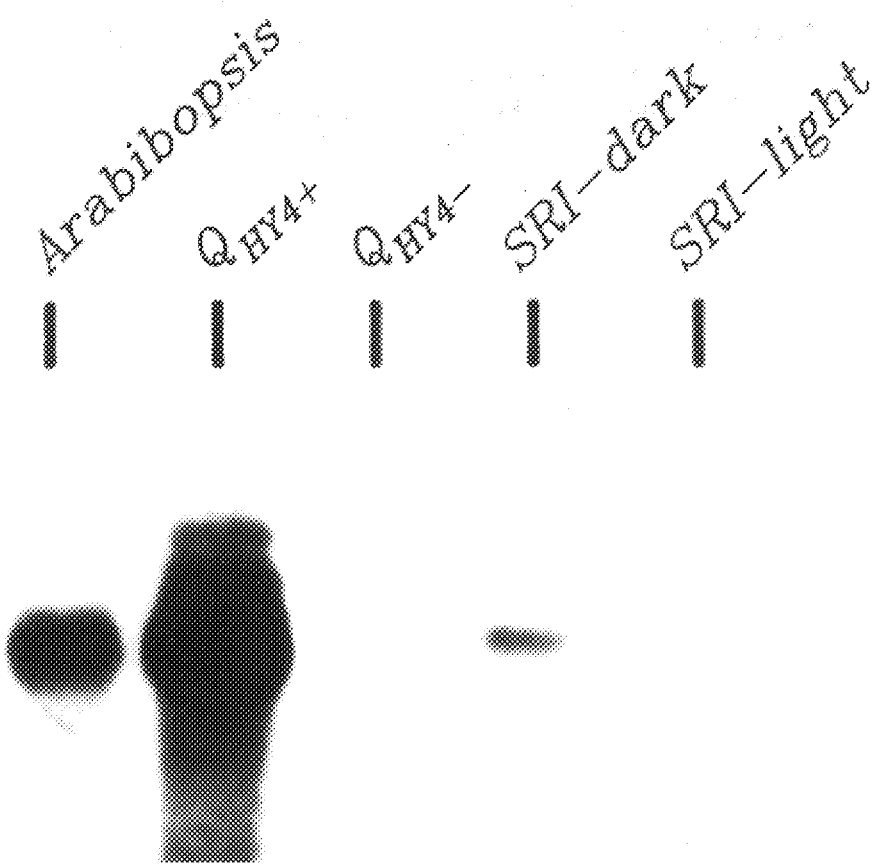

FIG. 16 is a photograph of a gel depicting expression of HY4 in wild type and transgenic plants. Total leaf proteins were extracted from wild type plants grown either under white light (Arabidopsis, SRI-light) or grown in the dark (SRI-dark), and from the $T_2$ progeny of transgenic tobacco plants also grown under white light (Q-HY4+) or in the dark (Q-HY4−). Proteins obtained from each set of plants were analyzed by Western blotting using anti-HY4C antibody.

FIG. 17A–17H is a series of graphs depicting the respective hypocotyl lengths of transgenic and wild type plants grown under various light conditions. Seeds obtained from the transgenic tobacco plant, Q, and the wild type parent plant, SRI, were germinated in soil under white light for 4 days. Seeds so germinated were then grown under blue light (5 μmole m$^{-2}$ s$^{-1}$), red light (19 μmole m$^{-2}$ s$^{-1}$), white light (16 w m$^{-2}$), or in the dark for 7 days, after which the hypocotyl length of each seedling was measured. The number of seedlings measured (n) and the average hypocotyl length (A) are indicated on each panel. FIG. 17A: QHY4$^-$; FIG. 17B QHY4$^+$.

Figure 18:

FIG. 18 is a photograph of a gel showing cosegregation of hypersensitivity to blue light cosegregates with overexpression of HY4 in transgenic tobacco plants. Seeds from T$_2$ progeny of the transgenic tobacco plant line, Q, were grown on agar plates under white light for 4 days. Seeds so germinated were then grown under blue light (5 μmole m$^{-2}$ s$^{-1}$), red light (19 μmole m$^{-2}$ s$^{-1}$), white light (16 w m$^{-2}$), or in the dark for 7 days. Seedlings grown under the same light treatment which were relatively higher (H) or relatively shorter (S) were pooled into H and S groups. Total leaf proteins were prepared from each group of seedlings and were analyzed by Western blotting using anti-HY4C antibody.

Figure 19:
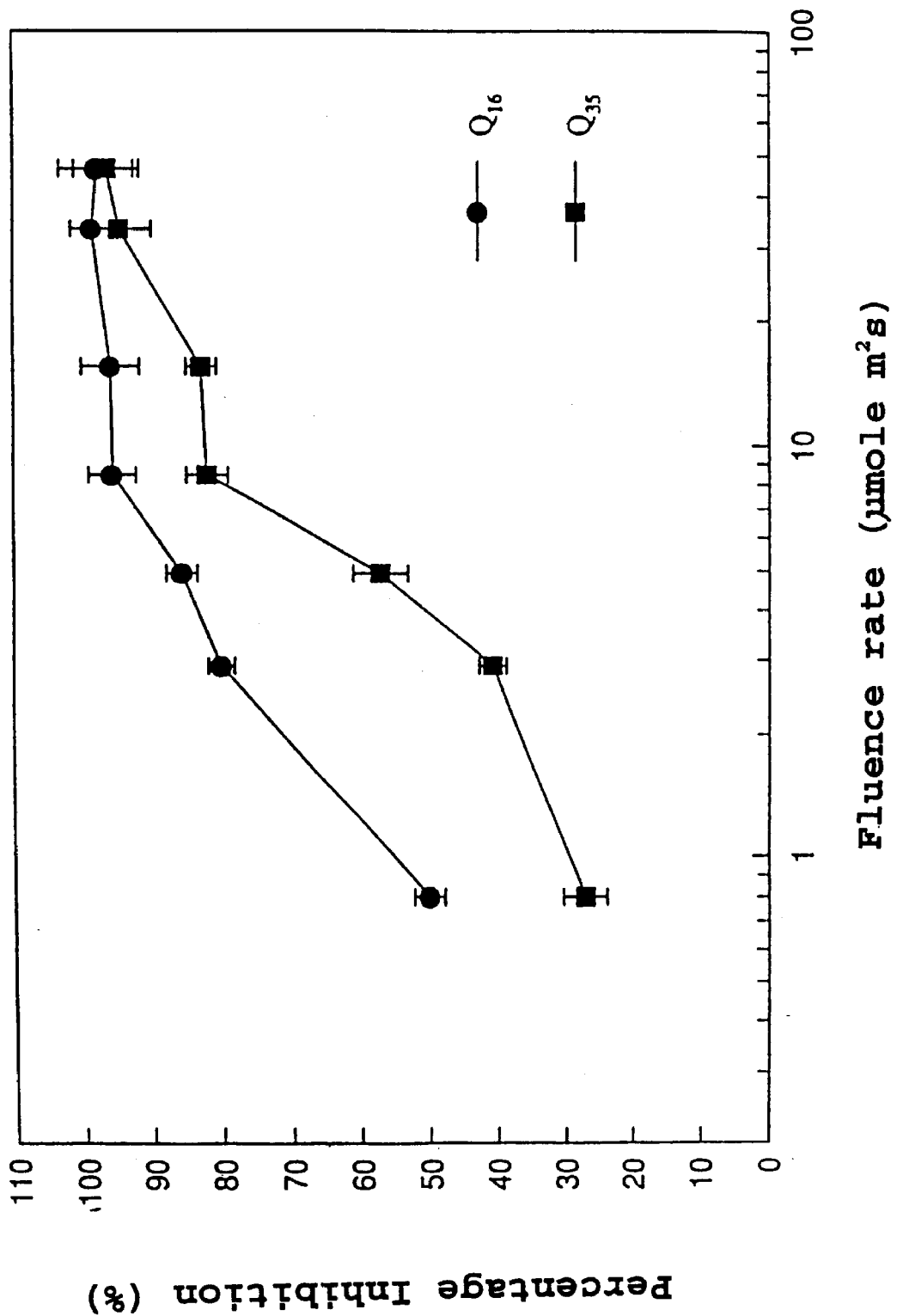

FIG. 19 is a graph showing dependence of blue light hypersensitivity in HY4 overexpressing tobacco plants upon the fluence rate. Seeds from the T$_2$ line Q$_{16}$, which is homozygous for overexpression of HY4 and for kanamycin resistance, and from the T$_2$ line Q$_{35}$, which is homozygous for kanamycin sensitivity and does not overexpress HY4, were germinated on agar plates for 4 days under white light and were then grown for 7 days under blue light of the following fluence rates: 0.8, 2.3, 4.9, 8.4, 15.5, 33.3 and 46.5 μmole m$^{-2}$ s$^{-1}$. Hypocotyl lengths were then measured. The percent of inhibition of hypocotyl growth was calculated as [Ld-Lb]/[Ld-Lw]×100, where L=hypocotyl length; d=dark; b=blue light; and w=white light. The values presented are the average values obtained from three independent measurements.

DETAILED DESCRIPTION OF THE PREFERRED EMBODIMENTS

Specific responses to blue light are known throughout nature and although blue light responses in plants were described by Darwin over a century ago (Darwin, 1881, The Power of Movement in Plants, Appleton, N.Y.), the data presented herein represent the first definitive report of the identification of a blue light photoreceptor. A gene corresponding to the HY4 locus of the plant *Arabidopsis thaliana*, has been isolated and characterized. The hy4 mutant (Koornneef et al., 1980, Pflanzenphysiol. Bd. 100:147) is one of several mutants (Liscum and Hangarter, 1991, Plant Cell 3:685) which are selectively insensitive to blue light in that the hypocotyl elongation response is not inhibited by exposure to blue light. This suggests that these mutants lack an essential component of the cryptochrome-associated light-sensing pathway.

The isolation and characterization of the HY4 gene and its protein product is described below. The use of the HY4 gene and its protein product for generation of transgenic plants, which plants have improved agronomic potential compared with their wild type counterparts, is also described below.

Figure 1:
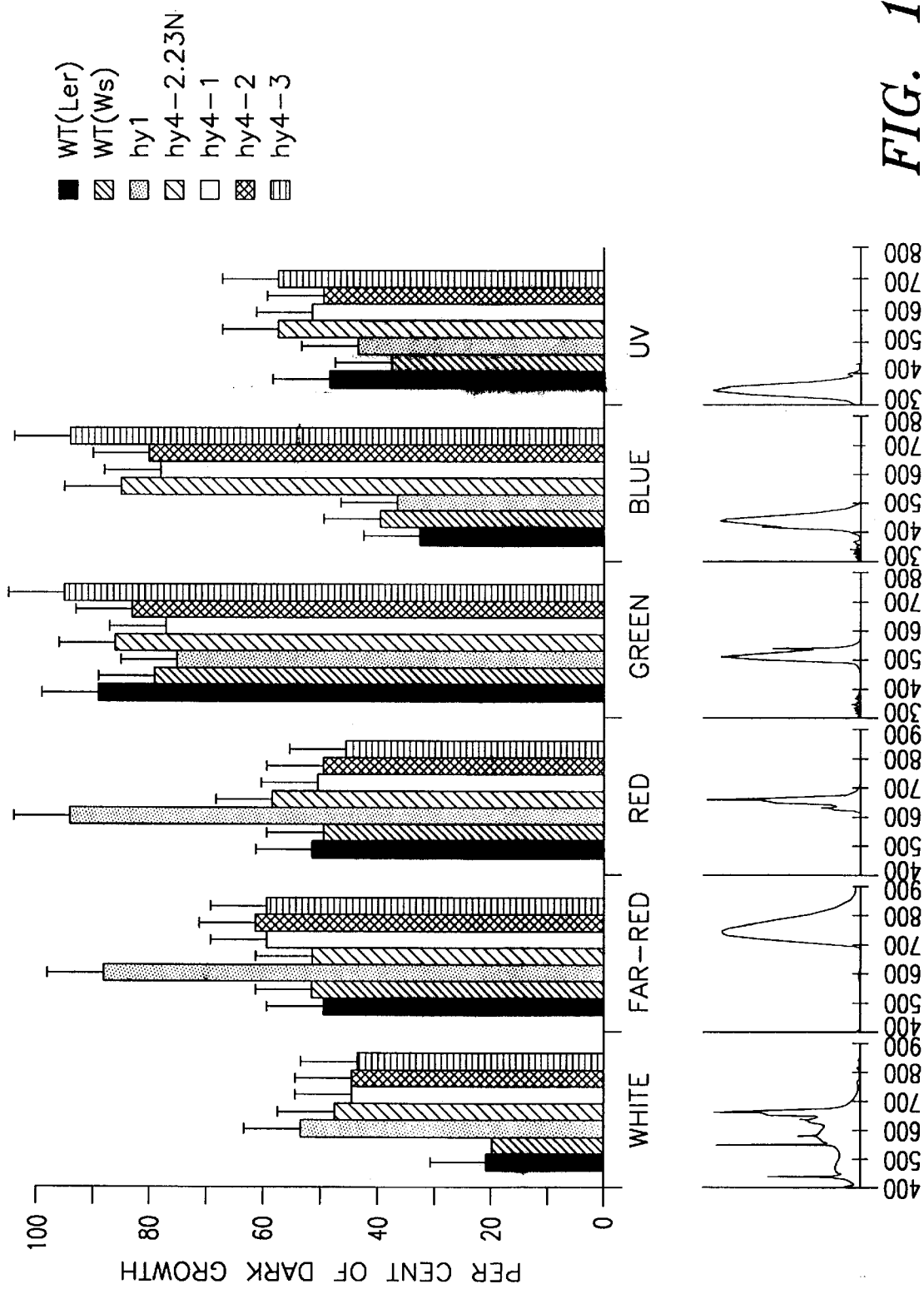
FIG. 1 is a graph depicting hypocotyl elongation in alleles of HY4. Seeds of alleles of HY4 (hy4-2.23N; hy4-1; hy4-2; hy4-3), hy1 (Koornneef et al., 1980, Pflanzenphysiol. Bd. 100:147) and wild type ectotypes Landsberg erecta (Ler: parental background of hy4-2.23N, hy4-1) and Ws (Wassilewskija, background of hy4-2, hy4-3) were plated on MS agar plates (Murashige and Skoog, 1962) Physiol. Plant 15:473) and were stored for two days at 4° C. before germination. Plates were shifted to white light for 36 hour to induce germination and were then transferred to the light condition indicated on the figure for an additional 5 days. For each treatment, hypocotyl lengths from 10 seedlings were measured and expressed as a percentage of the hypocotyl length of seedlings from a control plate which had been grown in the dark after induction of germination (hypocotyl lengths for dark-grown seedlings were similar for all mutants and parental ecotypes). Experimental light sources were from Sylvania (Danvers Mass.); the bulb type, filters and photon fluence rates ($\mu$mol m$^{-2}$ s$^{-1}$) were as follows: far-red, F40/232/RS, filter FRF 700 (Westlake Plastics, Lenni, Pa.), fluence 17 (700–800 nm) ; red, F40/2364/RS, filter Red Shinkolite (Argo Plastic, Calif.), fluence 26; green, F40/2196/RS, filter 2092 (Polycast Technology, Calif.) , fluence 25; blue, F40/246, filter 2424 (Polycast Technology), fluence 28; UV, F40 BLB, fluence 25; white, 'cool white', fluence 65. Photon fluence rates and spectra which are shown here were determined by a LabSpec VNIR 512 spectroradiometer (Analytical Spectral Devices, Boulder, Colo.).

In order to isolate and characterize the HY4 gene, several new mutant alleles of HY4 in *Arabidopsis thaliana* were isolated. To confirm that these mutants were impaired in blue light-dependent inhibition of hypocotyl elongation (Koornneef et al., 1980, Pflanzenphysiol. Bd. 100:147), wild type and hy4 seedlings were grown under various light sources and the length of the hypocotyls was measured after 6 days (FIG. 1). A mutant which was deficient in the red light photoreceptor (phytochrome), hy1 (Koornneef et al., 1980, Pflanzenphysiol. Bd. 100:147), was included for comparison. All hy4 alleles exhibited an impaired blue light response compared with wild type plants and with hy1. In addition, all of the hy4 mutant alleles exhibited a slightly impaired response to UV light compared with wild type plants. In contrast, the hy4 mutant alleles responded normally to red or far-red light unlike those plants containing the hy1 lesion which are insensitive to this region of the spectrum.

A mutant allele of HY4 (hy4-2) was isolated from a population of 8,000 transgenic lines of Arabidopsis which contain random T-DNA insertions (Feldman, 1991, Plant J. 1:71). Genetically, the identity of this allele was established by the inability of the tagged mutant to complement the original hy4 allele (hy4-2.23N; Koornneef et al., 1980, Pflanzenphysiol. Bd. 100:147). Furthermore, when hy4-2 was out-crossed to wild type plants and 2,500 F$_2$ progeny were screened for cosegregation of the hy4 phenotype and resistance to kanamycin, all of the seedlings with a hy4 phenotype were also kanamycin resistant and therefore contained the T-DNA insertion.

Figures 2A, 2B:
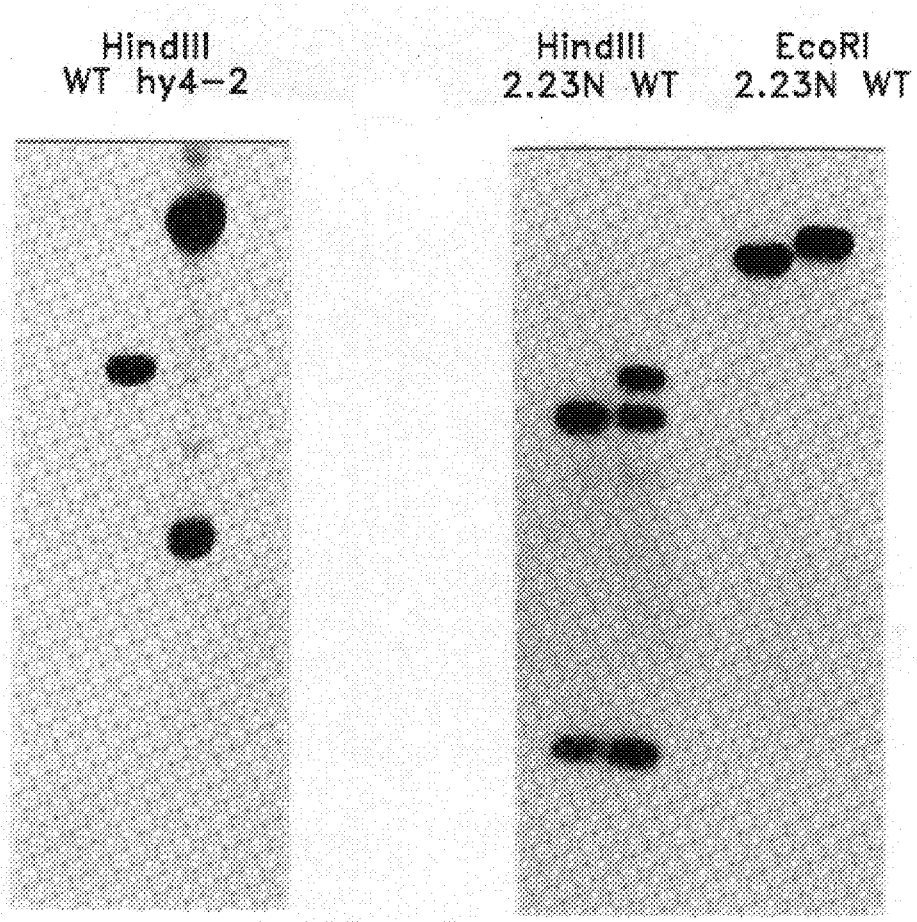
FIG. 2a: The HY4 locus is shown to be disrupted by T-DNA in the hy4-2 allele. Plant genomic DNA flanking the site of a T-DNA insertion was cloned using standard methods (Maniatis et al., 1982, Molecular Cloning: A Laboratory Manual, Cold Spring Harbor, N.Y.). Genomic DNA was prepared from hy4-2 (the T-DNA tagged mutant). This DNA was digested with SalI and BstEII (which do not cut within the vector sequences) and was then religated and electroporated into *Escherichia coli* (*E. coli*) and plated on medium containing ampicillin. Resulting colonies were screened for the presence of plant DNA flanking the T-DNA integration site. Two colonies were identified each containing approximately 15 kb of plant DNA. DNA (5 $\mu$g) obtained from hy4-2 and from the wild type parental Ws strain (WT) was digested with HindIII, electrophoresed through 0.7% agarose and blotted onto nitrocellulose filters. This DNA was probed with a fragment of rescued DNA containing left-border vector sequences in addition to plant genomic DNA downstream of the T-DNA insertion site (indicated in FIG. 3 below). The hybridizing band present in the wild type DNA is absent in the mutant and is replaced by two new bands resulting from the insertion of the T-DNA.
FIG. 2b: The hy4-2.23N allele is shown to contain a small deletion. DNA (5 $\mu$g) obtained from hy4-2.23N and the wild type isogenic parent (Landsberg erecta) were digested with restriction endonucleases, electrophoresed through 0.7% agarose and transferred to nitrocellulose filters. DNA on the filters was probed with full length HY4 cDNA. The difference in the electrophoretic pattern between hy4-2.23N and the wild type is indicative of a deletion of approximately 2 kb in the mutant genome.

DNA which flanked the site of the T-DNA insertion was rescued and was used to probe a Southern blot containing genomic DNA obtained from both the hy4-2 mutant and the wild type parent (*A. thaliana*, ectotype Ws). In FIG. 2a, it is evident that the probe (which contained T-DNA border sequences as well as plant sequences) hybridized to a single band in the lane containing wild type DNA. Hybridization to two bands was evident in the lane containing hy4-2 DNA, indicating that the wild type sequence had been interrupted in the mutant by the insertion of T-DNA.

The cloned plant DNA immediately adjacent to the site of T-DNA integration was used to screen an Arabidopsis complementary DNA library (Schindler et al., 1992, EMBO J. 11:1261) and ten overlapping cDNAs were subsequently isolated. The longest of these cDNAs was sequenced and was found to contain an open reading frame encoding a predicted protein of 681 amino acids in length (M$_r$ 75.8K) downstream from the first in-frame ATG start codon (FIG. 3). When genomic clones of HY4 were subsequently isolated and sequenced, three introns within the coding region were evident, one of which was positioned at the nucleotide immediately preceding the termination codon.

To confirm that the cDNA which was cloned and sequenced corresponded to the HY4 gene, four additional hy4 alleles were sequenced. The original hy4 allele (hy4-2.23N) was generated by fast neutron irradiation (Koornneef et al., 1980, Pflanzenphysiol. Bd. 100:147) and was therefore expected to contain a gross rearrangement in HY4-specific DNA. Indeed, when the hy4-2.23N allele was compared with the isogenic wild type parent by Southern analysis, a deletion beginning within the third intron, removing the 3' intron boundary and the 3' untranslated region of the cDNA, was revealed. However, the majority of the coding sequence and all of the promoter sequences of the HY4 gene remained intact in hy4-2.23N (FIG. 2b). The coding region of hy4-2.23N is extended due to the presence of sequences from the unspliced intron and there is no in-frame stop codon within 150 bases of the intron 5' junction (FIG. 2c). However, a putative polyadenylation signal (AATAAG) is present close to the intron 5' boundary. Northern analysis confirmed that the transcript in hy4-2.23N was shorter (by approximately 300 base pairs) than that expressed from the wild type HY4 gene (FIG. 2d), suggesting that the putative polyadenylation signal may indeed be used in this mutant. Furthermore, in general, levels of transcripts expressed from the mutant allele were reduced compared with the wild type which may be indicative of inefficient processing or of instability of mRNA in the mutant.

Figure 4B:
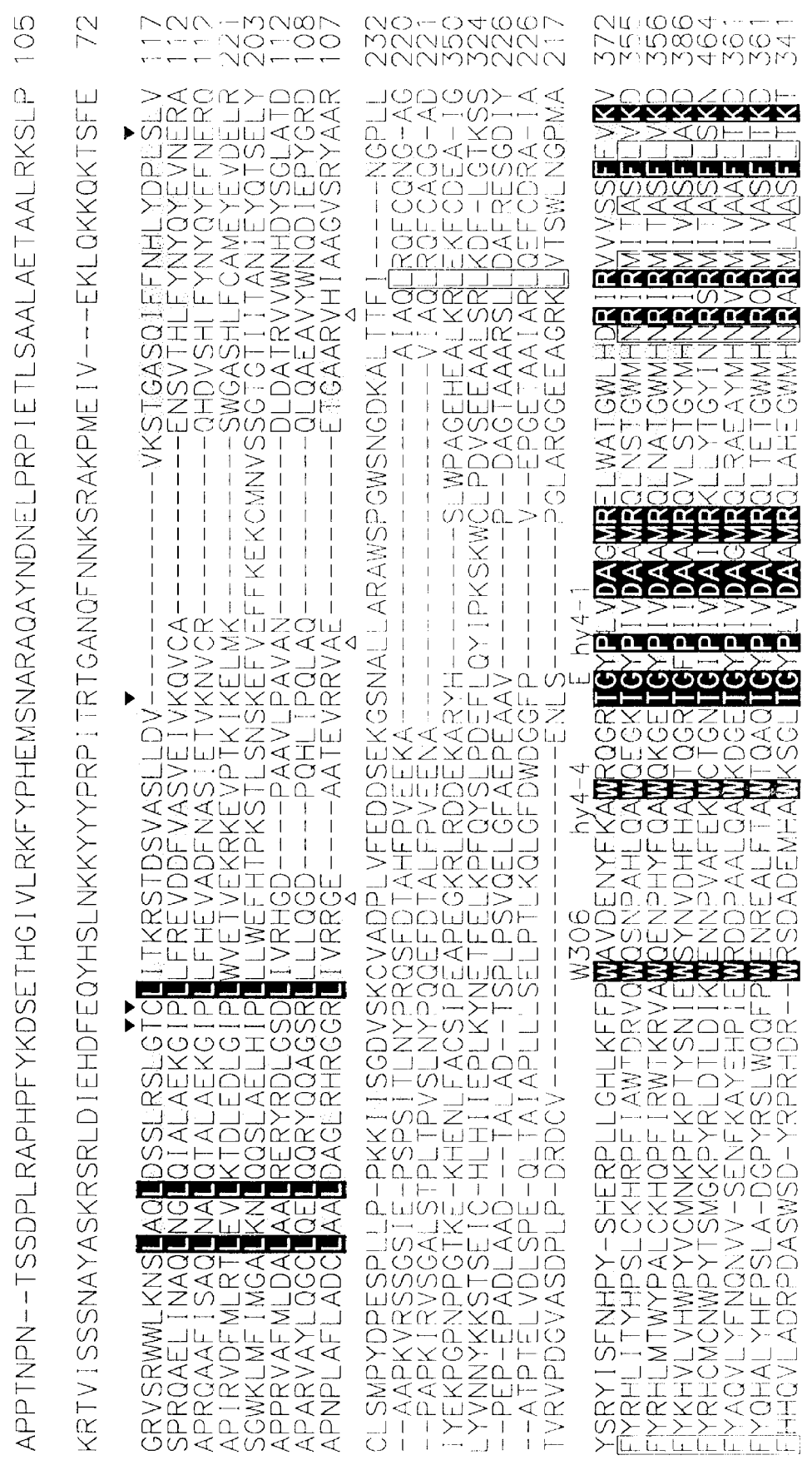
Figure 4C:
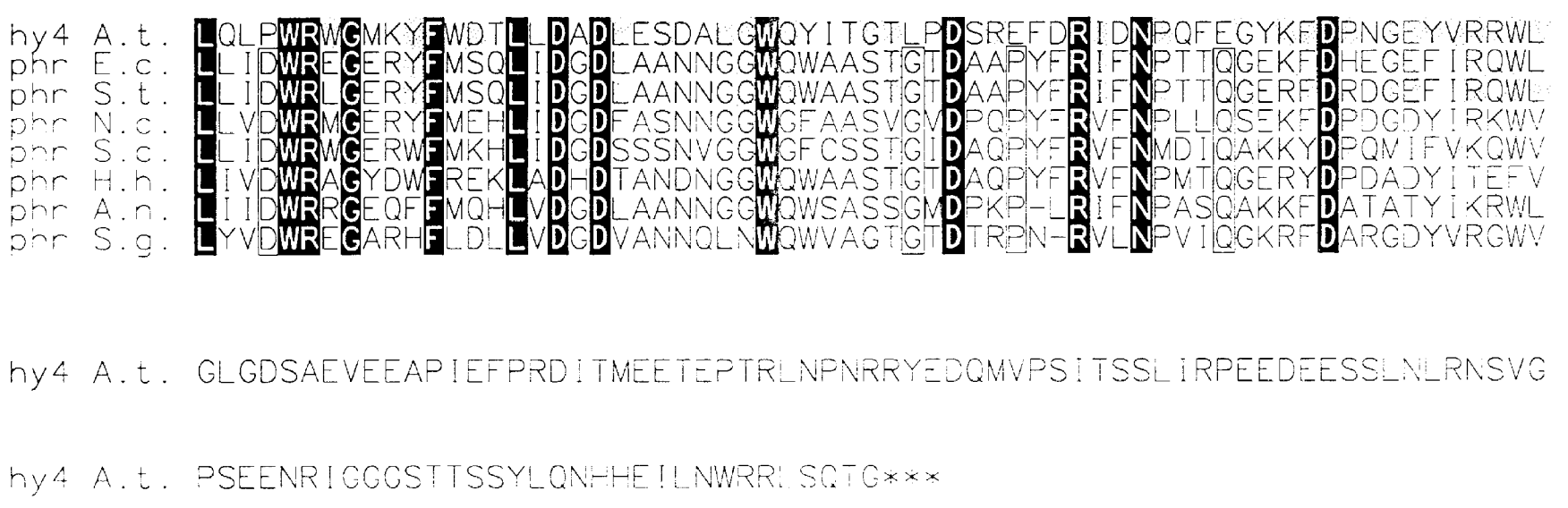

Two mutant alleles of HY4 generated by ethyl methane sulphonate (EMS) mutagenesis (hy4-1 and hy4-4) and an untagged allele (hy4-3) isolated from the T-DNA tagged Arabidopsis lines, were also characterized. Mutant hy4-1 was found to contain the amino acid substitution Gly340→Glu, and mutant hy4-4 contained the amino acid substitution Gly337→Asp. In addition, a 5 bp deletion (nucleotides 1,636–1,640) resulting in a frameshift causing premature termination of the protein was identified in hy4-3 (FIGS. 3, 4b and 4c).

The amino acid sequence of HY4 exhibited a striking sequence homology to the microbial DNA photolyases, a class of flavoproteins which catalyze light-dependent repair of pyrimidine dimers in UV-damaged DNA (Sancar, 1990, Mut. Res. 236:147). Optimal alignment of the HY4 sequence with those of seven characterized photolyases (FIG. 4a) revealed a sequence identity of 30% over a length of 500 amino acids and regions of homology as high as 70% (*E. coli* photolyase, amino acids 5–45) and 80% (amino acids 330–371) were also identified. The regions of highest homology occurred in those regions of the photolyase known to be involved in photolyase chromophore binding ((Malhotra et al., 1992, J. Biol. Chem. 267:2909). The carboxy-terminal domain of photolyase binds a reduced flavin (FADH$_2$), whereas the amino-terminal domain binds either a pterin (in the so-called short wavelength photolyases having an absorption maximum at 380 nm) or a deazaflavin derivative (in the long wavelength photolyases, absorption maximum of approximately 435 nm). That this homology has functional significance is indicated by the fact that two of the identified mutations in alleles of hy4 (hy4-1 and hy4-4) comprise amino acid substitutions in a region of exceptional sequence conservation in photolyases (FIG. 4a). Moreover, disruption of the homologous region in *E. coli* results in an inactive enzyme (Yamamoto, 1992, Molec. Gen. Genet. 232:1). Interestingly, a tryptophan residue which is conserved in all seven photolyases which is implicated in specific recognition of the pyrimidine-dimer substrate (*E. coli* Trp 277; Li and Sancar, 1990, Biochemistry, 29:5698), is not conserved in HY4.

Analysis of the amino-terminal region of the HY4 gene revealed additional sequence relatedness to the long wavelength class of photolyases. These photolyases possess a conserved Phe residue (Phe 34 in *S. griseus*) and a conserved sequence (Pro, His/Ala, Leu, His/Lys, Phe; residues 236–240 in *S. griseus*) which is characteristic of long wavelength-type photolyases (Kobayashi et al., 1989, Nucl. Acids Res. 17:4731; Yajima et al., 1991, Nucl. Acids Res. 19:5359). It is therefore likely that HY4 is capable of binding a deazaflavin derivative as a second chromophore which would account for the relative spectral sensitivity determined for HY4 (FIG. 1). Importantly, Arabidopsis photolyase activity has been reported to be of the short wavelength type (Pang and Hays, 1991, Plant Physiol. 95:536).

Within the HY4 molecule there is also significant sequence relatedness to rat smooth muscle tropomyosin A (Ruiz-Apazo and Nadal-Ginard, 1987, J. Biol. Chem. 262:4755). An identity of 30% and a relatedness of 45% over a stretch of 86 amino acids is evident between the two molecules (FIG. 4b). In HY4 this region of similarity is confined to the C-terminal one third of the protein, i.e., in a region distinct from that which shares homology with photolyases. Two of the mutant alleles of HY4 described above contain disruptions in this C-terminal portion of the protein (FIGS. 3 and 4c). One of these alleles contains a T-DNA insertion (hy4-2) and the other contains a 5 bp deletion which results in premature termination of the protein (hy4-3). Collectively, these data provide evidence that this region of HY4 is functionally important. Moreover, these data serve to distinguish the HY4 protein from DNA photolyases since photolyases typically do not contain additional sequences extending beyond the carboxy terminal flavin-binding domain.

Figure 2D:
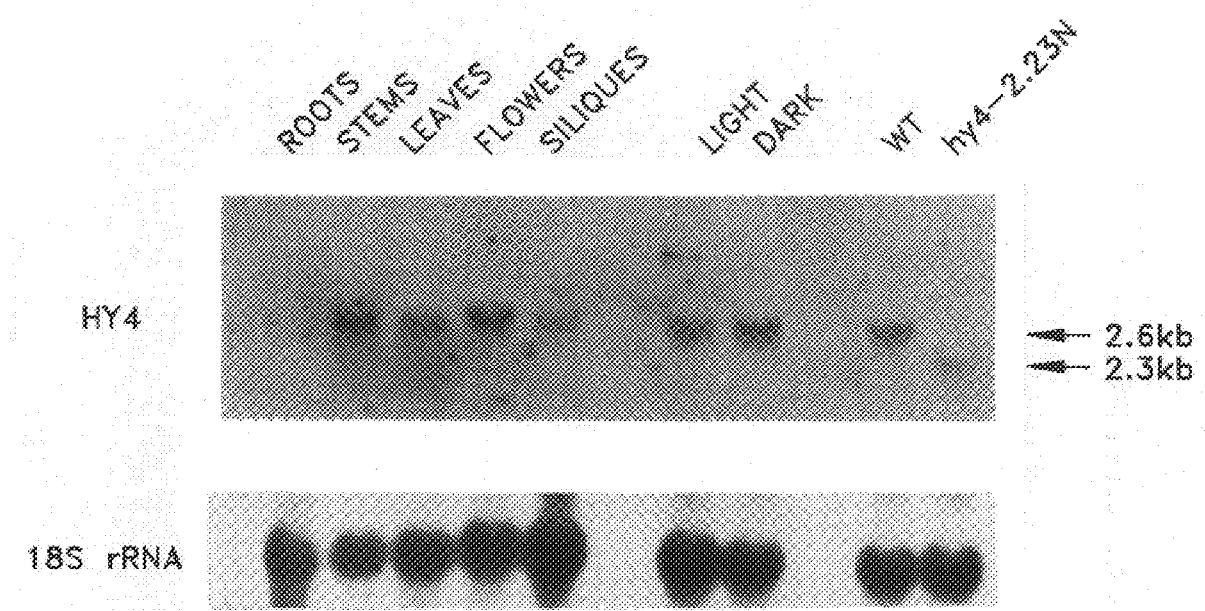
FIG. 2d: Analysis of transcription in HY4 is shown. RNA was prepared from roots, stems, leaves, flowers and immature siliques of 5-week old plants using standard methods (Ausebel et al., 1989, Current Protocols in Molecular Biology, Greene Wiley-Interscience). The dark adaption experiment involved 3-week old leaf tissue from plants either which were grown in continuous white light ('Light') or were placed in the dark for two days before sampling ('Dark'); light-grown and dark-grown 5-day old seedlings contained similar amounts of HY4 transcripts which were not significantly different from levels in the samples shown here. Wild type (Landsberg erecta) and mutant (hy4-2.23N) RNA was obtained from 3-week old leaf tissue. RNA (40 $\mu$g) which was resolved on a 1% formaldehyde agarose gel was transferred to nitrocellulose. This RNA was then probed under high stringency conditions with HY4 cDNA and was exposed for 4 days to X-ray film. The 18S ribosomal RNA obtained for each sample is shown for comparison.

It is unlikely that expression of HY4 is light regulated because the levels of HY4-specific mRNA were equivalent in dark-adapted and light-grown leaves, and were not altered in etiolated seedlings. Furthermore, expression of this gene is ubiquitous throughout the plant in that transcripts were evident in stems, leaves, flowers, siliques, and (following longer exposure of the filter to film) in roots (FIG. 2d).

The data described herein provide evidence that the HY4 gene encodes the apoprotein of a blue light photoreceptor. The hy4 mutant phenotype specifically impairs blue light responsiveness in Arabidopsis. The HY4 gene encodes a protein with significant homology to a very rare class of flavoproteins which catalyze blue light-dependent reactions. This homology has functional significance as evidenced by the discovery of point mutations in conserved domains which result in inactivation of both HY4 and photolyases. The action spectrum of blue light inhibition of hypocotyl elongation matches the absorption spectrum of the homologous long wavelength class of photolyases. However, it is now known that HY4 has no detectable photolyase activity.

The hydrophilicity profile of HY4 does not suggest an obvious membrane spanning domain, and the protein is a soluble protein (see below). For this reason, the reported blue light-dependent phosphorylation activity in isolated Arabidopsis membranes (Reymond et al., 1992, Proc. Natl. Acad. Sci. USA 89:4718) is unlikely to involve HY4.

The data presented above may be summarized as follows: 1) hy4 mutants are selectively insensitive to blue light; 2) these mutants exhibit semi-dominance similar to the corresponding red/far-red light photoreceptor mutants; and, 3) the sequence of the HY4 protein exhibits a striking similarity to that of microbial photolyases which are a known class of flavoproteins. These data therefore suggest that HY4 encodes a blue light photoreceptor. Additional support for this is derived from that fact that photolyases are themselves photoreceptors. They are members of a unique class of flavoproteins which are dependent for their activity on the absorption of light; this light may correspond to the near-UV or the blue region of the spectrum.

There is now described data which demonstrate that HY4 forms part of a small gene family, the cryptochrome (CRY) family, a group of genes also likely to encode photoreceptors. The DNA sequence of genes within this family differ from HY4 in the "non-photolyase" region (corresponding to the tropomyosin region of HY4) which presumably influences the type of substrates the products of these genes are capable of interacting with. These photoreceptors are likely to play a role in a wide variety of blue light responses, such as phototropism and stomatal opening, known in Arabidopsis to be mediated by sequences distinct from HY4. Furthermore, since there are two basic classes of photolyases, a near-UV-A absorbing and a blue light-absorbing class, it is likely that members of the CRY family include photolyase-related proteins which absorb light in the UVA region of the spectrum.

Blue light photoreceptors similar to HY4 exist in organisms distantly related to Arabidopsis. As discussed in more detail below, homologs of HY4 have been isolated and characterized in pea, tomato (the sequence of tomato HY4 is very similar to that of Arabidopsis, *Oryza sativa* and *Pisum savitum*) and rice and there is evidence, using Southern hybridization analysis, that there are related sequences in Ginkgo (a Gymnosperm).

Evidence that HY4 is a soluble protein.

Polyclonal antibodies against HY4 were prepared by immunization of rabbits with a 17 kD C-terminal fragment of HY4. The preparation of these antibodies is described below. This C-terminal domain, which is not homologous to photolyases, was obtained by overexpression of the recombinant HY4 gene in *E. coli*. The antibody recognized both the 75 kD in vitro translation product of HY4 RNA (obtained by in vitro transcription of the HY4 gene) and the 75 kD HY4 protein in wild type Arabidopsis; this protein was either missing or was present as a truncated protein in some of the hy4 mutants (FIG. 5).

Immunoblot and immunoprecipitation studies using this antibody demonstrated that HY4 was present in all of the tissues examined including leaf, root, stem, and flower and its accumulation was not dramatically effected by light. Moreover, the results establish that HY4 is a soluble protein in that it is most abundant in the soluble fraction, and is barely detectable in the microsomal fraction of Arabidopsis extracts (FIG. 6 A and B).

Homologs of HY4 in other plant species.

HY4-related proteins have been detected in other plant species including pea, mung bean, broccoli, cauliflower, and tobacco using antibody to Arabidopsis HY4. It was found that the HY4-related protein in pea and tobacco was labile to light; in the presence of light, HY4 was rapidly degraded in pea and was virtually undetectable in tobacco plants grown under light (see below). Using the Arabidopsis HY4 gene as a probe, HY4 related genes have been isolated from other plant species, namely pea, tomato and rice. Sequence analysis indicates that these genes are highly conserved among different plant species. The predicted amino acid sequence of Arabidopsis HY4 is approximately 80% and 60% identical to its homolog in pea and rice, respectively. This degree of sequence relatedness among HY4 proteins from different plant species is very similar to that of phytochrome proteins from Arabidopsis and rice which range from 65 to 73% in predicted amino acid sequence identity (Quail, 1991, Ann. Rev. Genet. 25:389).

To isolate the homologous HY4 gene in pea and rice, cDNA clones were isolated by screening rice and pea cDNA libraries using standard methods (Sambrook et al., 1989, Molecular Cloning, A Laboratory Manual, Cold Spring Harbor, N.Y.) The actual hybridization conditions were as follows:

Pea—Hybridization was carried out in 30% formamide, 5×Denharts and 5×SSPE at 42° C. for 24 hours; washing was conducted in 30% formamide, 5×SSPE, 0.5% SDS at 42° C. three times for 30 minutes each; the probe used was a random primer labeled C-terminal BamHI fragment (973 bp running from 541 to 1514 bp) of Arabidopsis HY4 cDNA, 1.4×10⁶ cpm/ml. Five positive clones were obtained from 250,000 plaques. Rice—Hybridization was carried out in 0.25% nonfat milk and 5×SSC at 48° C. for 16 hours; washing was conducted in 2×SSC and 0.1% SDS at 48° C. for 30 minutes followed by three washes of 30 minutes each in 2×SSC and 0.1% SDS at 45° C.; the probe used was a random primer labeled EcoRV/XbaI fragment (308 bp running from 1018 to 1325 bp from the 5' end of the HY4 DNA) of Arabidopsis HY4 cDNA at 2×10⁶ cpm/ml. Seventeen positive clones were obtained from 200,000 plaques. The nucleotide and predicted amino acid sequence of rice and pea specific HY4 is given in FIG. 7.

Family members of HY4.

A genomic Southern blot of Arabidopsis DNA was prepared and was hybridized under low stringency conditions to a fragment of HY4 containing the conserved flavin-binding domain. This fragment is a 308 bp fragment of HY4 spanning the EcoRV site at 1018 bp to the XbaI site at 1325 bp from the 5' end of the cDNA. Multiple bands of DNA hybridized to the probe under low stringency conditions which did not hybridize when high stringency conditions were employed (FIG. 8, A and B). Based on the number of bands, and their relative positions compared with known genes, a family of genes consisting of three or four members encoding HY4-related proteins in the Arabidopsis genome is contemplated. One of these genes has been cloned and sequenced, the experimental details of which cloning and sequencing are described below.

Numerous clones were isolated when the cDNA library described above was screened under low stringency conditions. DNA from one of these clones was sequenced and corresponds to a sequence which is closely related to HY4 in the amino-terminal chromophore-binding domain, but is entirely distinct from HY4 within a C-terminal extension of approximately 150 amino acids (FIG. 9). At the nucleotide level, 64% of this gene is identical to HY4. At the amino acid level, within the N-terminal photolyase-like domain, the new sequence has 53% identity and 70% similarity to HY4. Within the C-terminal domain, the sequence exhibits significant homology to domain E of the goldfish neuromodulin (46% similarity and 26% identity over a stretch of 50 amino acids; sequence search performed on PIR database at NCBI). Interestingly, the homology within the neuromodulin protein resides in a region believed to interact with the cytoskeletal proteins (LaBate and Skene, 1989, Neuron. 3:299). Thus, both HY4 and this related sequence have C-terminal extensions whose structure is consistent with a role in protein-protein interactions.

The related sequence thus corresponds to a structure predicted, according to the criteria discussed above, to be a member of the photoreceptor family. This sequence contains a conserved chromophore-binding domain and a divergent C-terminal "effector" region presumably capable of reacting with a different substrate. This family of HY4 related proteins has been named the CRY family (for cryptochrome) and the HY4-related gene has been named CRY2. The nucleotide and amino acid sequence of CRY2 is given in FIG. 9.

Characterization of HY4.

The coding region of the HY4 gene was cloned into a recombinant baculovirus vector wherein HY4 was fused to six histidine residues, a protein kinase A phosphorylation motif, and the thrombin cleavage motif (vector pAc-SGHisA, PharMingen, San Diego, Calif.). The cloning was accomplished as follows. A 575 bp fragment at the 5' end of the original HY4 cDNA, p3A, was synthesized using PCR and then was digested with SmaI and BamHI. The SmaI-BamHI fragment was then cloned into the plasmid pBS (Stratagene, La Jolla, Calif.) generating the plasmid pBS-3AN. The plasmid pBS-3AF was generated by obtaining a 1632 bp fragment comprising the 3' end of HY4 from the clone p3A and ligating this fragment into BamHI digested p3AN. The plasmid pAC-3AF was generated by obtaining a 2.2 kb SmaI fragment of pBS-3AF onto which was added XhoI linkers. This fragment was then ligated into the plasmid pAC.SGHisA. To generate the plasmid p3Ar (a plasmid expressing the complementary sequence to HY4, the orientation of HY4 in the original cDNA clone p3A was reversed by EcoRI digestion followed by religation of the insert into the vector in the opposite orientation.

SF9 cells were infected with a recombinant baculovirus which contains the the sequence within plasmid pAC-3AF. The HY4 protein was expressed to relatively high levels (approximately 4 mg/l) as a soluble protein which was specifically recognized by anti-HY4C antibodies. Anti-HY4C antibodies react with the C-terminal domain of HY4 and were prepared as described below. The HY4 protein so expressed was purified to near homogeneity using a nickel affinity column as described in Gruenwald and Heitz (1993, Baculovirus expression vector system: Procedures and methods manual. Pharminfen) with the following modifications: Protein which bound to the nickel column was eluted using 15 column volumes of 0.3 M NaCl. 0.05M Tris-HCl, pH 7.5, 0.001M EDTA, 0.005M dithiothreitol, 10% glycerol and 0.2M immidazol. The effluent was dialyzed against 400 volumes of dialysis buffer (0.25M NaCl, 0.05M Tris-HCl, pH 7.5) at 4° C. for 24 hr, and was concentrated by Centraprep 30 (Amicon) to one column volume. The high degree of purity of the HY4 is illustrated in FIG. 10 in the last two right hand lanes of the gel wherein a single band of protein is evident.

Purified HY4 appeared as a yellow color exhibiting absorption maxima at approximately 280, 360, and 450 nm, and a fluorescence emission peak at 520 nm (excitation at 360 nm). These spectral data are presented in FIG. 11. The fine structure of the 450 nm peak was similar to that observed for photolyase containing oxidized FAD, an indication of the hydrophobic environment of the flavin binding site (Payne et al., 1990, Biochemistry 29:5706). When the purified HY4 protein was denatured by either boiling or by addition of SDS, a chromophore was released which exhibited similar absorption peaks to that of HY4 at 360 and 450 nm. Thus, the chromophore was non-covalently bound to HY4, a situation which is identical to that in photolyases. When HY4 was reduced with dithionite, the absorption peak at 450 nm disappeared. However, when fully reduced HY4 was reoxidized overnight by residual oxygen in a tightly sealed tube,the 40 nm peak reappeared. These spectral data suggest the presence of an oxidized flavin adenine dinucleotide (FAD). No evidence was obtained suggesting the presence of a second deazaflavin chromophore in HY4 despite predictions obtained through DNA sequence analysis (Ahmad and Cashmore, 1993, Nature 366:162). However, it is possible that insufficient amounts of deazaflavin chromophore are available in insect cells for binding to HY4.

The spectral data strongly suggest that purified HY4 contains a fully oxidized FAD. This distinguishes purified HY4 from the photolyases. All photolyases purified to date under aerobic conditions contain this cofactor in blue neutral radical or partially-oxidized form (FADH°); this free radical form of FAD is believed to be the consequence of oxidization of the fully reduced, physiological form (FADH$_2$) during purification. Absorption maxima at 300–400 nm (UV-A) and at 500–600 nm (green) are characteristic of the free radical FADH°-containing photolyase. It is believed that the fully oxidized flavin of the purified HY4 is not simply the result of the experimental conditions used and that the flavin chromophore of HY4 possesses redox properties which are distinct from that of photolyase-associated flavoprotein. This conclusion is supported by the action spectral data for HY4, in that, given the correlation between the strong absorption in the green range observed for both the free radical FADH° and the action spectrum of HY4, it is likely that this free radical species represents the in vivo redox state of the flavin of HY4.

Inhibition of hypocotyl growth by HY4.

Six additional hy4 alleles were isolated whose respective locations on the HY4 gene are shown in FIG. 12. Further, a blue light insensitive elongated hypocotyl mutant which is not a member of the hy4 complementation group and which is therefore likely to be similar to the blu mutants isolated by Liscum and Hangarter (1991, Plant Cell. 3:685) has been isolated. Inhibition of hypocotyl elongation was examined under red light (600–700 nm, 26 micromole m$^{-2}$ s$^{-1}$), green light (500–600 nm, 50 micromole m$^{-2}$ s$^{-1}$), blue light (400–500 nm, 28 micromole m$^{-2}$ s$^{-1}$), and UV-A light (300–400 nm, 25 micromole m$^{-2}$ s$^{-1}$). All of the new alleles of hy4 with the exception of hy4-6, had a similar action spectrum to the original hy4 allele, including when higher fluences were used, a decreased response to green light (FIG. 13). Thus, these hy4 alleles exhibit decreased sensitivity to green and UV-A light, in addition to virtual "blindness" to blue light. In contrast, the putative blu mutant exhibited responses to both green and UV-A light which were similar to that of the wild type allele.

The hy4-6 mutant allele exhibited a wild type response in the green and UV-A regions of the spectrum (consistent with intact flavin binding and catalysis), but had virtually no response to blue light. This is consistent with the absence of binding or activity of the primary light harvesting deazaflavin chromophore. Sequence analysis of this mutant revealed a point mutation (Gly→Glu) at position 215 of the HY4 protein. This lesion is positioned between two conserved regions corresponding to the chromophore binding domains of the photolyase. Thus, since this lesion results in a change in the action spectrum, the identification of HY4 as the photoreceptor involved in inhibition of hypocotyl elongation is confirmed.

Overexpression of HY4 in plants.

There is now described experiments for the generation of transgenic tobacco plants, wherein the Arabidopsis HY4 gene is overexpressed. Several transgenic tobacco plant lines so generated contained significant amounts of HY4 protein in both dark- and light-grown plants. In contrast, the endogenous tobacco HY4-related protein in these plants was only evident in dark-grown plants and was undetectable in light-grown plants. When the progeny of these transgenic tobacco plants were grown under blue light, they exhibited a short-hypocotyl phenotype. This phenotype was blue-light dependent and was not observed in either etiolated seedlings or in seedlings grown under red light. Moreover, the short-hypocotyl phenotype in these plants cosegregated with overexpression of the HY4 gene, and was clearly regulated by the fluence rate of the light. Collectively, these data establish that enhanced expression of HY4 results in enhanced sensitivity of transgenic tobacco plants to blue light and as a consequence, short bushy tobacco plants are generated.

It is immediately apparent that since it is shown above to be possible to generate transgenic tobacco plants exhibiting a short hypocotyl phenotype using the Arabidopsis HY4 gene, it is also possible to generate short hypocotyl transgenic plants from other species using the Arabidopsis HY4 gene, or in fact HY4 genes from yet other species. Thus, the invention should be construed to include HY4 genes from many different types of plant species which genes may be used to generate transgenic plants with the desired phenotype from yet other either related or unrelated plant species. Further, the invention is not limited to the hypocotyl of the plant, in that, the hypocotyl of the plant and the stem of the plant should be considered synomonous for the purposes of the invention.

Plant materials and light treatment used in the experiments described below. For hypocotyl-length determination, seeds were sown on soil or agar plates containing MS salt medium. The seeds were germinated under continuous white light (200 micromole $m^{-2}$ $s^{-1}$) for 3–4 days to facilitate uniform germination, and were then subjected to different light or dark treatments for 7–8 days except where otherwise stated. Plants grown on soil were covered with a thin transparent plastic membrane and were sub-irrigated throughout the experiment; all treatments were carried out in an environmentally-controlled growth chamber. Experimental light sources, filters, and fluence rates were as follows: white (400–800 nm): "cool white" fluorescent tubes, 20–200 micromole $m^{-2}$ $s^{-1}$; blue (400–510 nm): F40/246 bulb (Sylvania, Danvers, Mass.), 2424 filter (Polycast Tech, Los Angeles, Calif.), 0.8–46.5 micromole $m^{-2}$ $s^{-1}$; red (600–700 nm): F40/2364/RS bulb (Sylvania), Red Shinkolite filter (Argo Plastic, Los Angeles, Calif.), 20 micromole $m^{-2}$ $s^{-1}$. Photon fluence rates and spectra were determined using a LabSpec VNIR 512 spectroradiometer (Analytical Spectral Devices, Boulder, Colo.).

The HY4 gene encodes a 75 kD protein which comprises two domains. The N-terminal domain (of approximately 55 kD) shares homology with photolyases and is believed to correspond to the chromophore binding domain of this class of enzymes. The C-terminal domain of HY4 is believed to act as the "effector" portion of the molecule. As noted above, HY4 is a member of a small gene family, wherein each member shares significant sequence homology in the "photolyase domain" of the molecule. Thus, in order to ensure detection of HY4 rather than the protein products of other members of this family of genes in transgenic plants, antibody was prepared against the C-terminal (HY4C) domain of HY4, which domain exhibits homology to tropomyosin.

Polyclonal antibodies directed against the HY4 protein were obtained by immunizing rabbits with a 17 kD C-terminal fragment of HY4 (referred to as HY4C), that region of the protein which does not exhibit homology to the photolyases. The HY4C sequence was expressed as an E. coli fusion protein containing six histidine residues using the E. coli expression vector pET16b (Novagen, Madison, Wis.). The protein so produced was purified using a nickel affinity column (Qiagen, Chatsworth, Calif.). Rabbits were injected with 100 mg of HY4C fusion protein followed by the administration of several booster injections containing 300 to 500 mg of protein every 3 to 4 weeks. Serum was obtained from the rabbits and anti-HY4C IgG was extracted therefrom using a CM Affi-Gel blue gel, followed by an immunoaffinity column comprising HY4C-coupled Affi-Gel 15 gel (BioRad, Melville, N.Y.). This procedure resulted in the generation of anti-HY4C IgG antibody at a concentration of 40 mg/ml which was then stored in 40% glycerol at −20° C.

Purified HY4C (FIG. 13A) was used to prepare polyclonal antibodies directed against this protein in rabbits. Serum obtained from rabbits so immunized immunoprecipitate an in vitro transcription/translation product of HY4 cDNA (FIG. 13B). The specificity of the anti-HY4C antibody was further established by Western blot analysis wherein proteins prepared from wild type and hy4 mutant Arabidopsis plants were tested (FIG. 14).

HY4 was detected using either immunoprecipitation or Western blotting methods. Immunoprecipitation was performed using standard technology well known in the art. Briefly, an in vitro transcribed and translated HY4C product was reacted with anti-HY4C and the resulting immunoprecipitated product was detected using standard methods. For Western blot analysis, crude extracts of plants were prepared by mixing, by homogenization, approximately 5 mg of plant tissue per 0.1 ml of 2×SDS-PAGE sample buffer and boiling the mixture for 3 minutes immediately after homogenization. Proteins were fractionated in an SDS-PAGE mini-gel and were then transferred to a nitrocellulose filter. Equal amounts of fresh tissue homogenate were loaded in each lane of the gel, which amounts were monitored by staining the filter with Ponceau S (Sigma, St. Louis, Mo.). The filter was destained and rinsed with PBS containing 0.3% Tween-20. The filter was then incubated in the presence of either anti-HY4 antisera (1/3000 dilution) or anti-HY4C IgG (25 ng/ml). Binding of either antibody to proteins on the filter was assessed by their reaction with goat anti-rabbit IgG conjugated to horseradish peroxidase (1/5000) (Amersham, Arlington Heights, Ill.); bound antibodies were detected by ECL (enhanced chemiluminescence, Amersham) and the amount of antibody bound was recorded by exposing the filter to X-ray film for approximately 10 to 60 seconds. Anti-HY4N antibody, i.e., that antibody which reacts exclusively with the N-terminal portion of HY4, was prepared in an identical manner to that described above except that a 30 kD N-terminal fragment of HY4 was used.

As illustrated in FIG. 15, the 75 kD HY4 protein was detected in crude plant extracts obtained from wild type Arabidopsis (Landsberg) and two hy4 mutant alleles, hy4-1 and hy4-4. These two alleles have been shown by DNA sequence analysis to contain point mutations which result in amino acid substitutions (Gly 340→Glu in hy4-1 and Gly 337→Asp in hy4-4). No HY4 protein was detected in two other alleles, hy4-2.23N (Koornneef et al., 1980, Pflanzenphysiol. Bd. 100:147) and hy4-2; these alleles have been shown to contain either a deletion in the third intron (hy4-2.23N) or a T-DNA insertion in the coding region (hy4-2) of HY4. Another allele, hy4-3, contains a 5 bp deletion which results in a shift in the HY4 reading frame and thus, premature termination of the protein. The hy4-3 allele encodes a protein of a 63 kD in place of a 75 kD wild type HY4 as expected based upon sequence analysis (FIG. 15). Collectively, the results presented in FIG. 15 establish that anti-HY4C specific antibody is monospecific for HY4. The same antibody also recognized a single 70–80 kD protein in samples prepared from other plant species including pea, mung bean, broccoli, cauliflower and tobacco (described below).

Generation of transgenic plants expressing HY4. Tobacco plants (Nicotiana tabacum cv. SR1) were transformed with the plasmid pTCOE3. This plasmid contains a 2.3 kb Arabidopsis HY4 cDNA (obtained as described above) fused to the cauliflower mosaic virus (CaMV) 35S promoter inserted into the EcoRI site of the Ti vector plasmid, pKYLX7 (Schard et al., 1987, Gene 61:1). Transformation of tobacco plants was accomplished using the Agrobacterium-mediated leaf disc transformation method described by Horsch et al. (1988, Leaf Disc transformation, Plant Molecular Biology Manual A5:1). Transformants which were resistant to 100–500 mg/l of kanamycin and which overexpressed HY4 (assayed by Western blot analysis) were designated as primary transformants and were referred to as $T_0$. The progeny of the selfed $T_0$ were referred to as $T_1$; the progeny of the selfed $T_1$ were referred to as $T_2$, etc.

At least five primary transformants ($T_0$) expressed detectable quantities of Arabidopsis HY4 when assessed by Western blot analysis. Among these five transformants, three plant lines appeared to segregate kanamycin resistance consistent with this gene being inserted at a single locus. The remaining two plant lines appeared to contain two sites wherein kanamycin resistance was inserted (Table 1).

TABLE 1

Segregation of Kanamycin Resistance and Hypocotyl Length of the Transgenic Tobacco Plants

| Plant Lines | Kanamycin Resistance | | | | Hypocotyl Length | | | |
|---|---|---|---|---|---|---|---|---|
| | Resistance | Sensitive | $X^2$ (3:1) | $X^2$ (15:1) | Short (3–6 mm) | High (10–14 mm) | $X^2$ (3:1) | $X^2$ (15:1) |
| Q | 243 | 87 | 0.36 | | 251 | 78 | 0.19 | |
| E | 52 | 17 | 0.12 | | 139 | 48 | 0.02 | |
| P | 112 | 28 | 1.87 | | | | | |
| G | 130 | 9 | | 0.11 | 135 | 14 | | 1.5 |
| H | 106 | 8 | | 0.14 | | | | |
| B | 0 | 114 | | | 0 | 111 | | |
| SRI | 0 | 127 | | | 0 | 120 | | |

Progenies of 6 regenerated tobacco lines (Q, E, P, G, H, B) and the wild type tobacco (SRI) plants were germinated under white light and grown either on the agar plates containing kanamycin (500 mg/l) for 14 days before scoring for the kanamycin resistance, or on agar plate containing no kanamycin for 7 days under blue light (20 $\mu$mole/m$^2$S$^2$) before measuring of the hypocotyl length. The numbers in each column represent numbers of plants.

The transgenic line Q, believed to contain a single transgene, was selected for further analysis. Data are presented in FIG. 16 which demonstrate expression of HY4 in two Q line progeny both of which exhibit kanamycin resistance. The HY4-related protein in wild-type tobacco (SRI) was detected in etiolated plants but not in light-grown plants (FIG. 16). In view of this, the HY4 present in the transgenic Q plants is presumed to be encoded by the Arabidopsis HY4 gene.

$T_o$ transgenic plants which did not overexpress HY4 did not exhibit obvious phenotypic differences compared with regenerants which do not overexpress HY4. However, when the $T_1$ seedling progeny of the HY4 overexpressing transformants were grown under dim white light (20 micromole m$^{-2}$ s$^{-1}$), a significant proportion of the seedlings were shorter than that of the wild-type plants. This exaggerated light-induced inhibition of hypocotyl elongation was found to be blue-light specific (FIG. 16). The hypocotyl length for the progeny ($T_1$) of the Q transgenic line were very similar to that of wild-type plants grown under either red light, in the dark, or under strong white light. As shown in FIG. 17, the distribution of hypocotyl length of Q and wild-type tobacco seedlings was almost indistinguishable (about 21 mm) when these plants were grown in the dark. However, the hypocotyl length of both transgenic and wild-type seedlings was reduced to about 4 mm when these plants were grown under strong white light (200 micromole m$^{-2}$ s$^{-1}$). When grown under red light, both transgenic and wild-type seedlings exhibited an average seedling length of about 17 mm. Irrespective of whether these plants were grown under red light, strong white light, or whether they were grown in the dark, the no difference was detected between wild type or transgenic plants. In contrast, when the plants were grown under blue light or white light, the transgenic Q line progeny clearly segregated into two distinct populations according to hypocotyl length—one population exhibited hypocotyl lengths similar to that of wild-type plants, whereas the second population exhibited a substantial inhibition of hypocotyl elongation (FIG. 16). This segregation of the short-hypocotyl phenotype was further analyzed in $T_1$ Q, E and G transgenic lines. Within each line tested, the ratio of the number of short:wild-type hypocotyl lengths was the same as the ratio of the number of kanamycin resistant:sensitive plants (Table 1). This ratio was 3:1 for transgenic lines Q and E, and was 15:1 for the transgenic line G (Table 1). Thus, both blue-light induced short hypocotyl length and kanamycin resistance were transferred to the transgenic plants following introduction of the plasmid PTCOE3 encoding HY4 and kanamycin resistance.

The blue-light dependent short-hypocotyl phenotype exhibited by transgenic tobacco plants was found to be correlated with overexpression of HY4. In this part of the study, groups of twenty seedlings exhibiting either the short (S) and wild-type sized (H) phenotype grown under blue light were examined for expression of HY4 by Western blot analysis. The results of this experiment are presented in FIG. 18. HY4 was detected in seedlings exhibiting short-hypocotyl length but not in wild type seedlings (FIG. 17, blue).

In an independent study, seedlings from the transgenic Q line were grown under blue light, hypocotyl lengths were measured after which the seedlings were transplanted to soil for growth under white light. Following two weeks of growth, each plant was individually analyzed for hypocotyl length and for expression of HY4. Each of the plants in the short hypocotyl group accumulated significant quantities of Arabidopsis HY4, while most of the plants exhibiting wild-type hypocotyl length exhibited no detectable HY4. These data clearly establish that the short-hypocotyl phenotype exhibited by the transgenic plants cosegregates with overexpression of Arabidopsis HY4. In contrast, when transgenic seedlings were grown either in the dark or under red light, only a small variation in hypocotyl length was observed among these plants which did not serve to distinguish them from wild type plants, which wild type plants also exhibited similar variations. When these transgenic seedlings were divided into "short" and "high" hypocotyl groups and the proteins contained therein were analyzed as described above, HY4 was detected in both groups (FIG. 17, red and dark). These data confirm that the short-hypocotyl phenotype is blue-light specific. These results have been reproduced using additional HY4-overexpressing transgenic tobacco lines. When the "short" and "high" seedlings were grown under dim white light (20 micromole m$^{-2}$ s$^{-1}$) and were then assayed for the presence of HY4, HY4 was clearly present in the "short" seedlings but was barely detectable in the "high" seedlings (FIG. 17, white). This result is consistent with the conclusion described above, as the plants are likely to be responding to the blue light region of the spectrum provided in the "cool" white light.

The data described herein demonstrate that overexpression of HY4 in seedlings gives rise to a short hypocotyl length phenotype. To determine whether this phenotype correlates with sensitivity to blue light, the relative sensitivities of transgenic plants generated as described above, to different light intensities was compared with corresponding light sensitivities in wild-type plants. The phenotype of the HY4-overexpressing line $Q_{16}$ (a $T_2$ line of Q which is homozygous for the HY4 transgene) was compared with the "wild-type" line $Q_{35}$ (a $T_2$ line of Q lacking the HY4 transgene) when each set of plants was grown under different fluence rates of blue light. The data are presented in FIG. 19. It was evident that the short-hypocotyl phenotype of $Q_{16}$ seedlings was most marked at a fluence rate of 2.8 micromole $m^{-2} s^{-1}$. At lower or higher fluence rates, the difference in hypocotyl length between transgenic and wild type plants was less marked. When the fluence rate (46 micromole $m^{-2} s^{-1}$) was near saturation for the wild type plant, almost no difference was observed between the two types of plants. These data therefore establish that the short-hypocotyl phenotype in the transgenic tobacco seedlings is a consequence of hypersensitivity to blue light resulting from overexpression of the Arabidopsis HY4 gene. Based on the data presented in FIG. 19, an approximate 4 to 5 fold increase in sensitivity of the transgenic HY4 overexpressing line to blue light is evident.

In summary, the studies presented above establish that (i) the HY4 gene product is a 75 kD protein, which protein is recognized by anti-HY4C antibody; (ii) transgenic tobacco plants overexpressing Arabidopsis HY4 produce shorter hypocotyls when grown under blue light than those produced by non-overexpressing siblings; and, (iii) the short hypocotyl phenotype is mediated by elevated sensitivity of these transgenic plants to blue light, which elevated sensitivity is a direct result of overexpression of HY4.

Generation of transgenic plants which are shorter than otherwise substantially homozygous wild type plants. Transgenic plants may be generated which are shorter than their wild type counterparts by inserting into the cells of a plant an HY4 gene capable of being expressed in the cells and thereby conferring upon the cells enhanced sensitivity to blue light, which sensitivity mediates reduced hypocotyl (stem) growth of the plant compared with a substantially homozygous wild type plant. As noted above, such transgenic plants are not limited to the combination in the example given above (i.e., the Arabidopsis HY4 gene in tobacco plants), rather this example provides evidence that it is possible to generate transgenic plants with the desired phenotype using different combinations of genes and plant species.

In order to ensure expression of HY4 in a plant cell, the gene is cloned into a vector such as, but not limited to, the Ti vector pKYLXN, wherein expression of HY4 is placed under the control of a promoter such as, but not limited to, the CaMV 35S promoter. In general, suitable vectors such as pKYLXN also encode resistance to one or more antibiotics in order to provide an initial screen to determine whether or not successful transformation of the cells has taken place. The vector and promoter sequences to be used will vary depending upon the type of plant being used. However, suitable vector, promoter and plant combinations will be readily apparent to those of skill in the art and can be found for example in Maliga et al. (1994, Methods in Plant Molecular Biology: A Laboratory Manual. Cold Spring Harbor, N.Y.). Plants are transformed by the leaf disc transformation method described above, or by other methods which are known in the art and can be found for example in Maliga et al. (1994, Methods in Plant Molecular Biology: A Laboratory Manual. Cold Spring Harbor, N.Y.).

Cells so transformed may examined for the presence of HY4 by Southern blot hybridization analysis. Expression of HY4 in these cells is assessed using anti-HY4 antibody following the methods described above. Seedlings are obtained from transgenic plants derived from cells so transformed. These seedlings are then examined for their sensitivity to blue light and for their ability to give rise to hypocotyls (stems) which are shorter than hypocotyls produced by seedlings from otherwise substantially homozygous wild type plants, also using the methods described above.

Transgenic shorter than normal plants which can conceivably be generated using the methods and compositions of the invention include all plants both known and unknown. Examples of such plants include, but are not limited to, Gymnosperms and Angiosperms, which Angiosperms include rice, oats, wheat, barley, sugarcane, maize, rye, soybean, sorghum, tomato and corn.

Generation of transgenic plants which are longer than otherwise substantially homozygous wild type plants. Based upon the data provided above, it follows that transgenic plants which are longer than otherwise substantially homozygous wild type plants may be generated in a manner similar to that described above for short plants, except that cells are transformed with a nucleic acid sequence which is complementary to all or a portion of the HY4 gene (i.e., the sequence is oriented in the cell such that it specifies the non-coding strand of the HY4 gene). Expression of complementary HY4 sequences in such plant cells will serve to diminish or ablate expression of wild type HY4, thereby reducing the sensitivity of the plant to blue light resulting in increased hypocotyl length.

Following the procedures described above, cells are transformed with a plasmid containing HY4 complementary sequences cloned under the control of a suitable promoter. Transgenic plants are generated from cells so transformed and the cells of these transgenic plants are examined for expression of complementary HY4 sequences. Seedlings from plants which express HY4 complementary sequences are selected and examined for their ability to give rise to longer hypocotyls and therefore plants which are longer than their wild type nontransgenic counterparts. This type of technology is common in the art of plant biology in that complementary sequences have been used to inhibit fruit ripening (Gray et al., 1992, Plant Molec. Biol. 19:69; Oeller et al., 1991, Science 254:437; Smith et al., 1988, Nature 334:724).

Alternatively, the technique of cosuppression may be used to inhibit expression of HY4. In this case, the subject gene (e.g., HY4 is positioned juxtaposed to a promoter in the "sense" orientation, which positioning results in suppression of expression of the subject gene (Assaad et al., 1993, Plant Mol. Biol. 22:1067; Brusslan et al., 1993, Plant Cell 5:667; Napoli et al., 1990, Plant Cell 2:279).

Nucleic acid sequences complementary to HY4 which are useful for reducing or inhibiting expression of HY4 in a transformed cell include sequences which are complementary to the entire coding region of the HY4 gene or sequences which are complementary to a portion of the gene. Complementary sequences comprising a portion of HY4 which are useful in the invention are those which are as short as 10 nucleotides in length or which are almost as long as the entire HY4 gene. It will be apparent to those skilled in the art, based upon what is known about the function of HY4, and in view of the teaching provided above, which complementary regions of HY4 are most useful for inhibition of expression of HY4. It is also apparent from the teaching provided above that generation of long stemed plants is not limited to use of the Arabidopsis HY4 gene. Rather, HY4 genes from other plants species may also be used.

Plants for which there is an agronomic advantage in being taller than their wild type counterparts include all plants which are relatively non-susceptible to lodging, for example, woody plants. Examples of such plants include, but are not limited to *Camellia sinensis*, Vitis spp, Gossypium, *Pinus radiata* and *Populus trichocarpa*.

Following the methods described herein, it is now possible to generate transgenic plants which give rise to stems, preferably hypocotyls, which are either shorter or longer than their respective substantially homozygous wild type counterparts. Such plants may have significant agronomic advantages over their wild type counterparts. For example, transgenic plants which are insensitive to blue light regulation of their growth may grow taller than wild type plants in regions which receive less than optimal sunlight. In addition, taller plants are likely to be thinner and thus it may be possible to cultivate larger numbers of taller plants, rather than shorter plants, per square foot of land. In addition, taller, woody plants which are not susceptible to lodging may also be useful as wind breakers.

In contrast, in other situations shorter plants have significant advantages over their taller homozygous counterparts. For example, shorter plants do not lodge (fall over) as easily as taller plants upon application of large amounts of fertilizer. In addition, it is now possible, using the compositions and methods of the invention, to envisage generation of "dwarf" plants by recombinant means which may have significant advantages over the conventional breeding techniques now used. For example, it has apparently heretofore not been possible to breed "dwarf" varieties of rice plants which retain the ability to produce "sticky" rice, possibly because the "dwarf" gene is linked to "stickiness". Since the genome of rice plants encode a HY4 homolog (described above), HY4 overexpressing rice plants may be generated which will not lodge and yet will retain the ability to produce "sticky" rice. Alternatively, the conventional "dwarfing" process may be dependent upon a change in hormone balance in the plant, which change may be incompatible with other desirable traits in the plant such as production of a source of food. For these reasons, the ability to manipulate one feature of the plant, i.e., tallness or shortness, has inherent advantages over conventional breeding techniques which likely result in alteration in many features of the plant.

While the particular cultivar of tobacco used in the experiments described herein did not yield an adult "dwarf" phenotype, other cultivars of tobacco are likely to yield "dwarf" plants when transformed with the HY4 gene. Those of skill in the art will know which cultivar of plant to use which will result in a "dwarf" phenotype. For example, it is known that *Nicotiana tabacum* cultivar SR1 (that used in the experiments described herein) did not yield a "dwarf" phenotype in experiments using phytochrome (Nagatani et al., 1991, Proc. Natl. Acad. Sci. USA 88:5207). However, overexpression of phytochrome in *Nicotiana plumbagnifolia* or *Nicotiana tabacum* (cultivar Xanthi) did yield a "dwarf" phenotype (Keller et al., 1989, EMBO J. 8:1005). Similarly, oat phytochrome is biologically active in transgenic tomatoes and gives rise to "dwarf" plants (Boylan et al., 1989, Plant Cell 1:765). Thus, by choosing the correct cultivar of plant, it is a simple matter, following the description provided herein, to generate "dwarf" plants.

The HY4 gene, its protein product and antibody directed to the protein may also be useful for identification of additional HY4 homologs in plants and even in animals. In plants, for example, HY4 homologs may be involved in regulation of stomatal opening. Manipulation of these HY4 homologs may therefore result in plants which are more resistant than their wild type counterparts to the absence of water. Thus, transgenic plants may be generated which are capable of growth in arid climates. In animals, regulation of circadian rhythms is controlled in part by blue light responses, which responses may be mediated by HY4-like genes. The methods and compositions of the invention may eventually prove useful in identifying and characterizing the genes involved in these processes.

In addition to HY4 genes in plants, HY4 related genes, i.e., HY4 family members, including but not limited to the CRY genes, are useful as probes for identification of additional genes encoding blue light/UV-A photoreceptors, which photoreceptors may be capable of such diverse functions such as stomatal opening in plants, influencing the response of plants to photoperiod, controlling spore formation in fungi, such as Penicillium spp, or regulation of circadian rhythms in animals.

Manipulation of the HY4 blue light photoreceptor (or related blue light/UV-A photoreceptors) may also be conducted to influence the production of secondary metabolites, such as flavonoids, in plants. Flavonoids are synthesized in plants via the phenylpropanoid pathway, which types of pathway are commonly regulated by blue light/UV-A photoreceptors. HY4 may be involved in regulation of this pathway because in the hy4 mutant, control of chalcone synthetase (a key enzyme in the phenylpropanoid pathway) is reduced. Flavonoids play a role in plant defense mechanisms (Hahlbrock et al., 1989, Ann. Rev. Plant Physiol. and Plant Mol. Biol. 40:347) and may also have pharmaceutical value. By manipulation of HY4, it may be possible to increase the production of these metabolites in plants/and or plant tissue.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A substantially pure preparation of a nucleic acid specifying the sequence of a plant HY4 gene, said gene comprising all mutants, derivatives or homologs of SEQ ID #5 which retain the activity of modifying stem length in a plant.

2. A substantially pure preparation of a nucleic acid encoding a plant HY4 polypeptide, said polypeptide comprising all mutants, derivatives or homologs of SEQ ID #6 which retain the activity of modifying stem length in a plant.

3. The nucleic acid of claim 1 comprising the DNA sequence of Arabidopsis HY4.

4. The nucleic acid of claim 1 comprising the DNA sequence of *Oryza sativa* HY4.

5. The nucleic acid of claim 1 comprising the DNA sequence of *Pisum sativum* HY4.

6. The nucleic acid of claim 3 which encodes the amino acid sequence of Arabidopsis HY4.

7. The nucleic acid of claim 4 which encodes the amino acid sequence of *Oryza sativa* HY4.

8. The nucleic acid of claim 5 which encodes the amino acid sequence of *Pisum sativum* HY4.

9. A recombinant vector comprising the nucleic acid of claim 1.

10. A recombinant cell comprising the nucleic acid of claim 1.

11. A transgenic plant, the cells of said plant comprising a substantially pure preparation of the nucleic acid of SEQ ID NO: 5, or any mutants, derivatives or homologs thereof which retain the activity of modifying stem length in said plant.

12. The transgenic plant of claim 11, the seeds of said plant comprising a substantially pure preparation of the nucleic acid of SEQ ID NO: 5, or any mutants, derivatives or homologs thereof which retain the activity of modifying stem length in said plant.

13. The transgenic plant of claim 11, the progeny of said plant comprising a substantially pure preparation of the nucleic acid of SEQ ID NO: 5, or any mutants, derivatives or homologs thereof which retain the activity of modifying stem length in said plant.

14. The transgenic plant of claim 11, wherein said nucleic acid is overexpressed in cells of said plant when compared with expression of said nucleic acid in a nontransgenic but otherwise substantially homozygous plant.

15. The transgenic plant of claim 14, the stem of said plant being shorter than the stem of a nontransgenic but otherwise substantially homozygous wild type plant.

16. The transgenic plant of claim 15, wherein said plant is selected from the group consisting of *Oryza sativa*, Avena spp, Triticum spp, *Hordeum vulgare*, Saccharum spp, *Zea mays, Secale cereale, Glycine max, Lycopersicon esculentum, Zea mays* and *Sorghum bicolor.*

17. A method of generating a transgenic plant having a substantially pure preparation of the nucleic acid of SEQ ID NO: 5, said plant comprising a shorter stem than an otherwise substantially homozygous wild type plant, comprising introducing into cells of said transgenic plant the nucleic acid of SEQ ID NO: 5, or any mutants, derivatives or homologs thereof which retain the activity of modifying stem length in said plant.

18. A substantially pure preparation of a nucleic acid complementary to a portion of the plant HY4 gene of SEQ ID #5, or any mutants, derivatives or homologs thereof which retain the activity of modifying stem length in a plant, wherein said nucleic acid is capable of inhibiting expression of said HY4 gene when introduced into cells comprising said HY4 gene.

19. A substantially pure preparation of a nucleic acid complementary to the plant HY4 gene of SEQ ID #5, or any mutants, derivatives or homologs thereof which retain the activity of modifying stem length in a plant, wherein said nucleic acid is capable of inhibiting expression of said HY4 gene when introduced into cells comprising said HY4 gene.

20. The nucleic acid of claim 18 or 19, comprising a sequence complementary to Arabidopsis HY4 nucleic acid.

21. The nucleic acid of claim 18 or 19, comprising a sequence complementary to *Oryza sativa* nucleic acid.

22. The nucleic acid of claim 18 or 19, comprising a sequence complementary to *Pisum sativum* HY4 nucleic acid.

23. A recombinant vector comprising the nucleic acid of claim 18 or 19.

24. A recombinant cell comprising the nucleic acid of claim 18 or 19.

25. A transgenic plant, the cells of said plant comprising a recombinant transgene comprising a nucleic acid complementary to a plant HY4 gene, said HY4 gene being SEQ ID NO: 5, or any portion, mutants, derivatives or homologs thereof which retain the activity of modifying stem length in said plant.

26. A transgenic plant, the cells of said plant comprising a recombinant transgene comprising a nucleic acid complementary to a HY4 gene, said HY4 gene being SEQ ID NO: 5, or any mutants, derivatives or homologs thereof which retain the activity of modifying stem length in said plant.

27. The transgenic plant of claim 25, the seeds of said plant comprising a recombinant transgene comprising a nucleic acid complementary to a plant HY4 gene, said HY4 gene being SEQ ID NO: 5, or any portion, mutants, derivatives or variants thereof which retain activity of modifying stem length in said plant.

28. The transgenic plant of claim 26, the seeds of said plant comprising a recombinant transgene comprising a nucleic acid complementary to a plant HY4 gene, said HY4 gene being SEQ ID NO: 5, or any mutants, derivatives or homologs thereof which retain the activity of modifying stem length in said plant.

29. The transgenic plant of claim 25, the progeny of said plant comprising a recombinant transgene comprising a nucleic acid complementary to a plant HY4 gene, said HY4 gene being SEQ ID NO: 5, or any portion, mutants, derivatives or variants thereof which retain the activity of modifying stem length in said plant.

30. The transgenic plant of claim 26, the progeny of said plant comprising a recombinant transgene comprising a nucleic acid complementary to a plant HY4 gene, said HY4 gene being SEQ ID NO: 5, or any mutants, derivatives or homologs thereof which retain the activity of modifying stem length in said plant.

31. The transgenic plant of claim 25 or 26, the stem of said plant being longer than the stem of a nontransgenic but otherwise substantially homozygous wild type plant.

32. A method of inhibiting expression of HY4 in a cell comprising introducing into said cell a recombinant transgene comprising a nucleic acid complementary to a plant HY4 gene, said HY4 gene being SEQ ID NO: 5, or any portion, mutants, derivatives or variants thereof which retain the activity modifying stem length in a plant.

33. A method of generating a transgenic plant comprising a longer stem than an otherwise substantially homozygous wild type plant, comprising introducing into cells of said transgenic plant a recombinant transgene comprising a nucleic acid complementary to a plant HY4 gene, said HY4 gene being SEQ ID NO: 5, or any mutants, derivatives or homologs thereof which retain the activity of modifying stem length in said transgenic plant.

34. The transgenic plant of claim 25 or 26, wherein said plant is selected from the group consisting of *Camellia sinensis*, Vitis spp, Gossypium spp, *Pinus radiata* and *Populus trichocarpa.*

\* \* \* \* \*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..6

( x i ) SEQUENCE DESCRIPTION: SEQ ID NO:1:

```
ACC  GGG  TAAAAAGTGC ATTTG                                             21
Thr  Gly
  1
```

( 2 ) INFORMATION FOR SEQ ID NO:2:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr  Gly
  1
```

( 2 ) INFORMATION FOR SEQ ID NO:3:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..102

( x i ) SEQUENCE DESCRIPTION: SEQ ID NO:3:

```
ACC  GGG  TAT  GTA  ACT  CGC  AAA  TCG  ACT  CTC  TCA  ACA  ATA  AGT  TCA  CAT    48
Thr  Gly  Tyr  Val  Thr  Arg  Lys  Ser  Thr  Leu  Ser  Thr  Ile  Ser  Ser  His
  1              5                        10                       15

AAA  GAT  CCT  AAA  CAT  TTT  CAA  ATT  GAA  AGT  CTC  CAA  ATT  TTC  AGT  AAG    96
Lys  Asp  Pro  Lys  His  Phe  Gln  Ile  Glu  Ser  Leu  Gln  Ile  Phe  Ser  Lys
            20                        25                       30

TTT  CAA                                                                         102
Phe  Gln
```

( 2 ) INFORMATION FOR SEQ ID NO:4:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr Gly Tyr Val Thr Arg Lys Ser Thr Leu Ser Thr Ile Ser Ser His
 1               5                   1 0                  1 5

Lys Asp Pro Lys His Phe Gln Ile Glu Ser Leu Gln Ile Phe Ser Lys
              2 0                  2 5                  3 0

Phe Gln
```

( 2 ) INFORMATION FOR SEQ ID NO:5:

( i ) SEQUENCE CHARACTERISTICS:
        ( A ) LENGTH: 2458 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 148..2190

( x i ) SEQUENCE DESCRIPTION: SEQ ID NO:5:

```
TCAAAAATCT TTTTTTTTG TTGTCTTTCT TCTCGAGAGA GATAAGTGAC CAAAGGGTTT       60

CGATTTCTGG AAATAGTTTG AATAAAAAAG TAATTTTTAT GTGATTATTG CCAAAGAAAA      120

GTTTTAGTTT TTTTTAGTTT GTGAGAG ATG TCT GGT TCT GTA TCT GGT TGT          171
                             Met Ser Gly Ser Val Ser Gly Cys
                              1               5

GGT TCT GGT GGT TGT AGT ATT GTA TGG TTT AGA AGA GAT CTT AGG GTT        219
Gly Ser Gly Gly Cys Ser Ile Val Trp Phe Arg Arg Asp Leu Arg Val
         1 0              1 5                  2 0

GAA GAT AAT CCA GCT TTA GCA GCA GCA GTA AGA GCT GGT CCA GTG ATT        267
Glu Asp Asn Pro Ala Leu Ala Ala Ala Val Arg Ala Gly Pro Val Ile
2 5              3 0                  3 5                  4 0

GCT CTG TTT GTT TGG GCA CCA GAA GAA GAA GGA CAC TAT CAT CCA GGT        315
Ala Leu Phe Val Trp Ala Pro Glu Glu Glu Gly His Tyr His Pro Gly
             4 5                  5 0                  5 5

AGG GTT TCT AGG TGG TGG CTC AAG AAC AGT TTG GCT CAG CTT GAT TCT        363
Arg Val Ser Arg Trp Trp Leu Lys Asn Ser Leu Ala Gln Leu Asp Ser
         6 0                  6 5                  7 0

TCT CTT AGA AGT CTT GGT ACT TGT CTT ATC ACC AAG AGA TCT ACT GAT        411
Ser Leu Arg Ser Leu Gly Thr Cys Leu Ile Thr Lys Arg Ser Thr Asp
     7 5                  8 0                  8 5

AGT GTT GCT TCT CTT CTT GAT GTT GTT AAA TCC ACT GGT GCT TCT CAG        459
Ser Val Ala Ser Leu Leu Asp Val Val Lys Ser Thr Gly Ala Ser Gln
     9 0                  9 5                 1 0 0

ATC TTC TTC AAC CAT TTG TAT GAT CCA TTG TCT TTG GTG CGT GAT CAC        507
Ile Phe Phe Asn His Leu Tyr Asp Pro Leu Ser Leu Val Arg Asp His
1 0 5                1 1 0                 1 1 5                1 2 0

CGA GCT AAA GAT GTT TTG ACG GCG CAA GGC ATA GCG GTT CGA TCA TTC        555
Arg Ala Lys Asp Val Leu Thr Ala Gln Gly Ile Ala Val Arg Ser Phe
             1 2 5                 1 3 0                1 3 5

AAC GCA GAC TTG CTT TAT GAG CCA TGG GAA GTG ACT GAT GAA TTA GGC        603
Asn Ala Asp Leu Leu Tyr Glu Pro Trp Glu Val Thr Asp Glu Leu Gly
         1 4 0                 1 4 5                 1 5 0

CGT CCT TTC TCT ATG TTT GCT GCG TTT TGG GAG AGA TGT CTT AGT ATG        651
Arg Pro Phe Ser Met Phe Ala Ala Phe Trp Glu Arg Cys Leu Ser Met
         1 5 5                1 6 0                1 6 5

CCT TAT GAC CCT GAG TCT CCT CTT CTT CCA CCT AAG AAG ATC ATT TCA        699
Pro Tyr Asp Pro Glu Ser Pro Leu Leu Pro Pro Lys Lys Ile Ile Ser
1 7 0                1 7 5                 1 8 0
```

| | | | | | | | | | | | | | | | | |
|---|---|---|---|---|---|---|---|---|---|---|---|---|---|---|---|---|
| GGG | GAT | GTG | TCT | AAA | TGT | GTT | GCG | GAT | CCA | TTG | GTG | TTT | GAG | GAT | GAC | 747 |
| Gly | Asp | Val | Ser | Lys | Cys | Val | Ala | Asp | Pro | Leu | Val | Phe | Glu | Asp | Asp | |
| 185 | | | | 190 | | | | | 195 | | | | | | 200 | |
| TCT | GAG | AAA | GGA | AGC | AAT | GCA | CTT | CTG | GCT | CGT | GCT | TGG | TCT | CCT | GGA | 795 |
| Ser | Glu | Lys | Gly | Ser | Asn | Ala | Leu | Leu | Ala | Arg | Ala | Trp | Ser | Pro | Gly | |
| | | | | 205 | | | | | 210 | | | | | 215 | | |
| TGG | AGT | AAT | GGT | GAT | AAA | GCT | CTC | ACA | ACG | TTT | ATA | AAC | GGT | CCA | TTG | 843 |
| Trp | Ser | Asn | Gly | Asp | Lys | Ala | Leu | Thr | Thr | Phe | Ile | Asn | Gly | Pro | Leu | |
| | | | 220 | | | | | 225 | | | | | 230 | | | |
| CTT | GAA | TAC | TCT | AAG | AAC | CGC | AGA | AAA | GCC | GAT | AGT | GCT | ACA | ACC | TCG | 891 |
| Leu | Glu | Tyr | Ser | Lys | Asn | Arg | Arg | Lys | Ala | Asp | Ser | Ala | Thr | Thr | Ser | |
| | | 235 | | | | 240 | | | | | 245 | | | | | |
| TTT | CTT | TCT | CCA | CAC | TTG | CAT | TTT | GGG | GAA | GTG | AGT | GTG | AGA | AAA | GTT | 939 |
| Phe | Leu | Ser | Pro | His | Leu | His | Phe | Gly | Glu | Val | Ser | Val | Arg | Lys | Val | |
| 250 | | | | | 255 | | | | | 260 | | | | | | |
| TTT | CAT | CTT | GTT | CGG | ATC | AAA | CAG | GTC | GCG | TGG | GCA | AAC | GAA | GGA | AAC | 987 |
| Phe | His | Leu | Val | Arg | Ile | Lys | Gln | Val | Ala | Trp | Ala | Asn | Glu | Gly | Asn | |
| 265 | | | | | 270 | | | | | 275 | | | | | 280 | |
| GAG | GCC | GGG | GAA | GAA | AGC | GTG | AAT | CTT | TTC | CTG | AAA | TCT | ATT | GGT | CTC | 1035 |
| Glu | Ala | Gly | Glu | Glu | Ser | Val | Asn | Leu | Phe | Leu | Lys | Ser | Ile | Gly | Leu | |
| | | | | 285 | | | | | 290 | | | | | 295 | | |
| AGG | GAG | TAT | TCT | AGG | TAC | ATA | AGT | TTT | AAC | CAT | CCA | TAT | TCC | CAT | GAA | 1083 |
| Arg | Glu | Tyr | Ser | Arg | Tyr | Ile | Ser | Phe | Asn | His | Pro | Tyr | Ser | His | Glu | |
| | | | 300 | | | | | 305 | | | | | 310 | | | |
| AGA | CCA | CTT | CTT | GGC | CAT | CTA | AAG | TTC | TTC | CCT | TGG | GCT | GTG | GAT | GAG | 1131 |
| Arg | Pro | Leu | Leu | Gly | His | Leu | Lys | Phe | Phe | Pro | Trp | Ala | Val | Asp | Glu | |
| | | 315 | | | | 320 | | | | | 325 | | | | | |
| AAC | TAT | TTC | AAG | GCA | TGG | AGG | CAA | GGC | CGG | ACT | GGA | TAT | CCG | TTG | GTC | 1179 |
| Asn | Tyr | Phe | Lys | Ala | Trp | Arg | Gln | Gly | Arg | Thr | Gly | Tyr | Pro | Leu | Val | |
| | 330 | | | | | 335 | | | | | 340 | | | | | |
| GAT | GCC | GGG | ATG | AGA | GAG | TTA | TGG | GCT | ACT | GGT | TGG | TTG | CAT | GAT | CGC | 1227 |
| Asp | Ala | Gly | Met | Arg | Glu | Leu | Trp | Ala | Thr | Gly | Trp | Leu | His | Asp | Arg | |
| 345 | | | | 350 | | | | | 355 | | | | | 360 | | |
| ATA | AGA | GTA | GTT | GTT | TCA | AGC | TTC | TTT | GTT | AAA | GTG | CTT | CAA | TTA | CCA | 1275 |
| Ile | Arg | Val | Val | Val | Ser | Ser | Phe | Phe | Val | Lys | Val | Leu | Gln | Leu | Pro | |
| | | | | 365 | | | | | 370 | | | | | 375 | | |
| TGG | AGA | TGG | GGG | ATG | AAG | TAT | TTC | TGG | GAC | ACA | CTT | CTT | GAT | GCG | GAT | 1323 |
| Trp | Arg | Trp | Gly | Met | Lys | Tyr | Phe | Trp | Asp | Thr | Leu | Leu | Asp | Ala | Asp | |
| | | | 380 | | | | | 385 | | | | | 390 | | | |
| TTA | GAA | AGC | GAT | GCT | CTT | GGT | TGG | CAA | TAC | ATT | ACC | GGT | ACT | CTC | CCG | 1371 |
| Leu | Glu | Ser | Asp | Ala | Leu | Gly | Trp | Gln | Tyr | Ile | Thr | Gly | Thr | Leu | Pro | |
| | | 395 | | | | 400 | | | | | 405 | | | | | |
| GAT | AGC | CGG | GAG | TTT | GAT | CGC | ATA | GAT | AAC | CCT | CAG | TTT | GAA | GGG | TAC | 1419 |
| Asp | Ser | Arg | Glu | Phe | Asp | Arg | Ile | Asp | Asn | Pro | Gln | Phe | Glu | Gly | Tyr | |
| | | 410 | | | | 415 | | | | | 420 | | | | | |
| AAG | TTT | GAT | CCA | AAT | GGT | GAA | TAC | GTA | AGG | CGA | TGG | CTT | CCT | GAA | CTC | 1467 |
| Lys | Phe | Asp | Pro | Asn | Gly | Glu | Tyr | Val | Arg | Arg | Trp | Leu | Pro | Glu | Leu | |
| 425 | | | | | 430 | | | | | 435 | | | | | 440 | |
| TCT | AGA | CTC | CCG | ACA | GAC | TGG | ATA | CAT | CAT | CCG | TGG | AAC | GCA | CCT | GAG | 1515 |
| Ser | Arg | Leu | Pro | Thr | Asp | Trp | Ile | His | His | Pro | Trp | Asn | Ala | Pro | Glu | |
| | | | | 445 | | | | | 450 | | | | | 455 | | |
| TCC | GTT | CTT | CAA | GCT | GCT | GGT | ATC | GAG | CTT | GGA | TCA | AAC | TAT | CCT | CTA | 1563 |
| Ser | Val | Leu | Gln | Ala | Ala | Gly | Ile | Glu | Leu | Gly | Ser | Asn | Tyr | Pro | Leu | |
| | | | 460 | | | | | 465 | | | | | 470 | | | |
| CCA | ATT | GTT | GGA | TTA | GAC | GAA | GCA | AAA | GCA | CGG | CTT | CAT | GAA | GCG | CTT | 1611 |
| Pro | Ile | Val | Gly | Leu | Asp | Glu | Ala | Lys | Ala | Arg | Leu | His | Glu | Ala | Leu | |
| | | 475 | | | | 480 | | | | | 485 | | | | | |
| TCA | CAG | ATG | TGG | CAA | CTA | GAA | GCT | GCT | TCA | AGA | GCT | GCA | ATA | GAG | AAC | 1659 |
| Ser | Gln | Met | Trp | Gln | Leu | Glu | Ala | Ala | Ser | Arg | Ala | Ala | Ile | Glu | Asn | |
| | | 490 | | | | 495 | | | | | 500 | | | | | |

```
GGA  TCC  GAA  GAA  GGA  CTT  GGA  GAT  TCT  GCT  GAG  GTA  GAG  GAA  GCT  CCT    1707
Gly  Ser  Glu  Glu  Gly  Leu  Gly  Asp  Ser  Ala  Glu  Val  Glu  Glu  Ala  Pro
505                      510                      515                      520

ATA  GAG  TTC  CCA  AGG  GAC  ATT  ACA  ATG  GAA  GAG  ACT  GAA  CCA  ACC  AGA    1755
Ile  Glu  Phe  Pro  Arg  Asp  Ile  Thr  Met  Glu  Glu  Thr  Glu  Pro  Thr  Arg
                    525                      530                      535

CTC  AAC  CCA  AAC  AGG  AGA  TAT  GAG  GAT  CAG  ATG  GTT  CCA  AGC  ATT  ACT    1803
Leu  Asn  Pro  Asn  Arg  Arg  Tyr  Glu  Asp  Gln  Met  Val  Pro  Ser  Ile  Thr
               540                      545                      550

TCT  TCT  TTG  ATC  AGA  CCT  GAA  GAA  GAC  GAA  GAG  TCG  TCT  CTT  AAT  TTG    1851
Ser  Ser  Leu  Ile  Arg  Pro  Glu  Glu  Asp  Glu  Glu  Ser  Ser  Leu  Asn  Leu
          555                      560                      565

AGA  AAT  TCA  GTA  GGA  GAT  AGC  AGA  GCA  GAG  GTT  CCA  AGG  AAC  ATG  GTT    1899
Arg  Asn  Ser  Val  Gly  Asp  Ser  Arg  Ala  Glu  Val  Pro  Arg  Asn  Met  Val
570                      575                      580

AAC  ACC  AAC  CAA  GCT  CAG  CAG  CGG  AGA  GCA  GAA  CCG  GCT  TCA  AAC  CAA    1947
Asn  Thr  Asn  Gln  Ala  Gln  Gln  Arg  Arg  Ala  Glu  Pro  Ala  Ser  Asn  Gln
585                      590                      595                      600

GTC  ACT  GCT  ATG  ATT  CCA  GAA  TTT  AAT  ATC  AGA  ATT  GTT  GCA  GAG  AGC    1995
Val  Thr  Ala  Met  Ile  Pro  Glu  Phe  Asn  Ile  Arg  Ile  Val  Ala  Glu  Ser
                    605                      610                      615

ACT  GAA  GAC  TCA  ACA  GCG  GAA  TCT  TCC  AGC  AGC  GGA  AGG  AGA  GAA  AGA    2043
Thr  Glu  Asp  Ser  Thr  Ala  Glu  Ser  Ser  Ser  Ser  Gly  Arg  Arg  Glu  Arg
               620                      625                      630

AGC  GGA  GGC  ATA  GTC  CCC  GAG  TGG  TCT  CCA  GGG  TAC  TCA  GAG  CAG  TTC    2091
Ser  Gly  Gly  Ile  Val  Pro  Glu  Trp  Ser  Pro  Gly  Tyr  Ser  Glu  Gln  Phe
          635                      640                      645

CCT  AGT  GAA  GAA  AAT  CGT  ATT  GGA  GGA  GGA  AGT  ACA  ACG  TCT  AGC  TAC    2139
Pro  Ser  Glu  Glu  Asn  Arg  Ile  Gly  Gly  Gly  Ser  Thr  Thr  Ser  Ser  Tyr
650                      655                      660

TTG  CAG  AAT  CAC  CAT  GAA  ATA  CTG  AAC  TGG  AGA  CGG  CTT  TCA  CAA  ACC    2187
Leu  Gln  Asn  His  His  Glu  Ile  Leu  Asn  Trp  Arg  Arg  Leu  Ser  Gln  Thr
665                      670                      675                      680

GGG  TAAAAAGTGC  ATTTGGAGGT  GCAAAGGAG  AGGAACATCA  TAAGGGCTGT                     2240
Gly

AACTCCGGGT  GAAATCTGGT  TGGACTGTAA  ACCGAGTACA  TTTGGTACGG  TTTAATGTAA              2300

TTCCGGTTAT  GGGGCTGGAG  AGAAACTATG  TAGGAGTTTG  TCTGATGTAC  ATTTTTATT               2360

TATCTCTGGT  TCCATCATGT  TATAATACAC  TGTATAGTAA  GTAGTCTGTT  GCTTGTGGTA              2420

TTAGACCAGG  TCTCATACTT  GTTGGCTTTC  AAAGTTTT                                        2458
```

( 2 ) INFORMATION FOR SEQ ID NO:6:

( i ) SEQUENCE CHARACTERISTICS:
        ( A ) LENGTH: 681 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ser  Gly  Ser  Val  Ser  Gly  Cys  Gly  Ser  Gly  Gly  Cys  Ser  Ile  Val
1                   5                   10                      15

Trp  Phe  Arg  Arg  Asp  Leu  Arg  Val  Glu  Asp  Asn  Pro  Ala  Leu  Ala  Ala
               20                      25                      30

Ala  Val  Arg  Ala  Gly  Pro  Val  Ile  Ala  Leu  Phe  Val  Trp  Ala  Pro  Glu
          35                      40                      45

Glu  Glu  Gly  His  Tyr  His  Pro  Gly  Arg  Val  Ser  Arg  Trp  Trp  Leu  Lys
     50                      55                      60

Asn  Ser  Leu  Ala  Gln  Leu  Asp  Ser  Ser  Leu  Arg  Ser  Leu  Gly  Thr  Cys
```

-continued

```
             65                      70                      75                      80
Leu  Ile  Thr  Lys  Arg  Ser  Thr  Asp  Ser  Val  Ala  Ser  Leu  Leu  Asp  Val
                    85                      90                      95

Val  Lys  Ser  Thr  Gly  Ala  Ser  Gln  Ile  Phe  Phe  Asn  His  Leu  Tyr  Asp
               100                     105                     110

Pro  Leu  Ser  Leu  Val  Arg  Asp  His  Arg  Ala  Lys  Asp  Val  Leu  Thr  Ala
               115                     120                     125

Gln  Gly  Ile  Ala  Val  Arg  Ser  Phe  Asn  Ala  Asp  Leu  Leu  Tyr  Glu  Pro
          130                     135                     140

Trp  Glu  Val  Thr  Asp  Glu  Leu  Gly  Arg  Pro  Phe  Ser  Met  Phe  Ala  Ala
145                     150                     155                     160

Phe  Trp  Glu  Arg  Cys  Leu  Ser  Met  Pro  Tyr  Asp  Pro  Glu  Ser  Pro  Leu
                    165                     170                     175

Leu  Pro  Pro  Lys  Lys  Ile  Ile  Ser  Gly  Asp  Val  Ser  Lys  Cys  Val  Ala
               180                     185                     190

Asp  Pro  Leu  Val  Phe  Glu  Asp  Asp  Ser  Glu  Lys  Gly  Ser  Asn  Ala  Leu
               195                     200                     205

Leu  Ala  Arg  Ala  Trp  Ser  Pro  Gly  Trp  Ser  Asn  Gly  Asp  Lys  Ala  Leu
          210                     215                     220

Thr  Thr  Phe  Ile  Asn  Gly  Pro  Leu  Leu  Glu  Tyr  Ser  Lys  Asn  Arg  Arg
225                     230                     235                     240

Lys  Ala  Asp  Ser  Ala  Thr  Thr  Ser  Phe  Leu  Ser  Pro  His  Leu  His  Phe
                    245                     250                     255

Gly  Glu  Val  Ser  Val  Arg  Lys  Val  Phe  His  Leu  Val  Arg  Ile  Lys  Gln
               260                     265                     270

Val  Ala  Trp  Ala  Asn  Glu  Gly  Asn  Glu  Ala  Gly  Glu  Glu  Ser  Val  Asn
          275                     280                     285

Leu  Phe  Leu  Lys  Ser  Ile  Gly  Leu  Arg  Glu  Tyr  Ser  Arg  Tyr  Ile  Ser
290                     295                     300

Phe  Asn  His  Pro  Tyr  Ser  His  Glu  Arg  Pro  Leu  Leu  Gly  His  Leu  Lys
305                     310                     315                     320

Phe  Phe  Pro  Trp  Ala  Val  Asp  Glu  Asn  Tyr  Phe  Lys  Ala  Trp  Arg  Gln
                    325                     330                     335

Gly  Arg  Thr  Gly  Tyr  Pro  Leu  Val  Asp  Ala  Gly  Met  Arg  Glu  Leu  Trp
               340                     345                     350

Ala  Thr  Gly  Trp  Leu  His  Asp  Arg  Ile  Arg  Val  Val  Val  Ser  Ser  Phe
          355                     360                     365

Phe  Val  Lys  Val  Leu  Gln  Leu  Pro  Trp  Arg  Trp  Gly  Met  Lys  Tyr  Phe
          370                     375                     380

Trp  Asp  Thr  Leu  Leu  Asp  Ala  Asp  Leu  Glu  Ser  Asp  Ala  Leu  Gly  Trp
385                     390                     395                     400

Gln  Tyr  Ile  Thr  Gly  Thr  Leu  Pro  Asp  Ser  Arg  Glu  Phe  Asp  Arg  Ile
                    405                     410                     415

Asp  Asn  Pro  Gln  Phe  Glu  Gly  Tyr  Lys  Phe  Asp  Pro  Asn  Gly  Glu  Tyr
               420                     425                     430

Val  Arg  Arg  Trp  Leu  Pro  Glu  Leu  Ser  Arg  Leu  Pro  Thr  Asp  Trp  Ile
          435                     440                     445

His  His  Pro  Trp  Asn  Ala  Pro  Glu  Ser  Val  Leu  Gln  Ala  Ala  Gly  Ile
          450                     455                     460

Glu  Leu  Gly  Ser  Asn  Tyr  Pro  Leu  Pro  Ile  Val  Gly  Leu  Asp  Glu  Ala
465                     470                     475                     480

Lys  Ala  Arg  Leu  His  Glu  Ala  Leu  Ser  Gln  Met  Trp  Gln  Leu  Glu  Ala
                    485                     490                     495
```

Ala Ser Arg Ala Ala Ile Glu Asn Gly Ser Glu Glu Gly Leu Gly Asp
            500                 505                 510

Ser Ala Glu Val Glu Glu Ala Pro Ile Glu Phe Pro Arg Asp Ile Thr
            515                 520                 525

Met Glu Thr Glu Pro Thr Arg Leu Asn Pro Asn Arg Arg Tyr Glu
530                 535                 540

Asp Gln Met Val Pro Ser Ile Thr Ser Ser Leu Ile Arg Pro Glu Glu
545                 550                 555                 560

Asp Glu Glu Ser Ser Leu Asn Leu Arg Asn Ser Val Gly Asp Ser Arg
            565                 570                 575

Ala Glu Val Pro Arg Asn Met Val Asn Thr Asn Gln Ala Gln Gln Arg
            580                 585                 590

Arg Ala Glu Pro Ala Ser Asn Gln Val Thr Ala Met Ile Pro Glu Phe
            595                 600                 605

Asn Ile Arg Ile Val Ala Glu Ser Thr Glu Asp Ser Thr Ala Glu Ser
610                 615                 620

Ser Ser Ser Gly Arg Arg Glu Arg Ser Gly Gly Ile Val Pro Glu Trp
625                 630                 635                 640

Ser Pro Gly Tyr Ser Glu Gln Phe Pro Ser Glu Glu Asn Arg Ile Gly
            645                 650                 655

Gly Gly Ser Thr Thr Ser Ser Tyr Leu Gln Asn His His Glu Ile Leu
            660                 665                 670

Asn Trp Arg Arg Leu Ser Gln Thr Gly
            675                 680

( 2 ) INFORMATION FOR SEQ ID NO:7:

( i ) SEQUENCE CHARACTERISTICS:
      ( A ) LENGTH: 615 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:7:

Met Ala Pro Ser Lys Arg Lys Ala Ser Ala Pro Pro Gln Thr Ser His
1               5                   10                  15

Val Asn Gly Asn Pro Ser Ala Asp Lys Arg Lys Thr Thr Thr Asp
            20                  25                  30

Ala Pro Pro Thr Asn Pro Asn Thr Ser Ser Asp Pro Leu Arg Ala Pro
            35                  40                  45

His Pro Phe Tyr Lys Asp Ser Glu Thr His Gly Ile Val Leu Arg Lys
            50                  55                  60

Phe Tyr Pro His Glu Met Ser Asn Ala Arg Ala Gln Ala Tyr Asn Asp
65                  70                  75                  80

Asn Glu Leu Pro Arg Pro Ile Glu Thr Leu Ser Ala Ala Leu Ala Glu
            85                  90                  95

Thr Ala Ala Leu Arg Lys Ser Leu Pro Val Arg Gln Ala Val Val His
            100                 105                 110

Trp Phe Lys Met Asp Leu Arg Leu His Asp Asn Arg Ser Leu Trp Leu
            115                 120                 125

Ala Ser Gln Lys Ala Lys Glu Ala Gly Val Pro Leu Ile Cys Leu Tyr
            130                 135                 140

Val Leu Ser Pro Leu Asp Leu Glu Ala His Leu Arg Ala Pro Ile Arg
145                 150                 155                 160

Val Asp Phe Met Leu Arg Thr Leu Glu Val Leu Lys Thr Asp Leu Glu

-continued

```
                        165                     170                     175
Asp  Leu  Gly  Ile  Pro  Leu  Trp  Val  Thr  Val  Glu  Lys  Arg  Lys  Glu
               180                     185                     190

Val  Pro  Thr  Lys  Ile  Lys  Glu  Leu  Met  Lys  Ser  Trp  Gly  Ala  Ser  His
               195                     200                     205

Leu  Phe  Cys  Ala  Met  Glu  Tyr  Glu  Val  Asp  Glu  Leu  Arg  Arg  Glu  Ala
     210                     215                     220

Lys  Leu  Val  Lys  Leu  Leu  Ala  Glu  Gly  Lys  Gly  Lys  Met  Ala
225                      230                     235                     240

Ala  Asp  Val  Val  His  Asp  Thr  Cys  Val  Val  Met  Pro  Gly  Ala  Leu  Gln
                    245                     250                     255

Ser  Gly  Ser  Gly  Gly  Gln  Tyr  Ala  Val  Tyr  Ser  Pro  Trp  Phe  Arg  Ala
               260                     265                     270

Trp  Ile  Lys  His  Ile  Glu  Glu  Asn  Pro  Glu  Cys  Leu  Glu  Ile  Tyr  Glu
          275                     280                     285

Lys  Pro  Gly  Pro  Asn  Pro  Pro  Gly  Thr  Lys  Glu  Lys  His  Glu  Asn  Leu
     290                     295                     300

Phe  Ala  Cys  Ser  Ile  Pro  Glu  Ala  Pro  Glu  Gly  Lys  Arg  Leu  Arg  Asp
305                      310                     315                     320

Asp  Glu  Lys  Ala  Arg  Tyr  His  Ser  Leu  Trp  Pro  Ala  Gly  Glu  His  Glu
                    325                     330                     335

Ala  Leu  Lys  Arg  Leu  Glu  Lys  Phe  Cys  Asp  Glu  Ala  Ile  Gly  Lys  Tyr
               340                     345                     350

Ala  Glu  Arg  Arg  Asn  Ile  Pro  Ala  Met  Gln  Gly  Thr  Ser  Asn  Leu  Ser
          355                     360                     365

Val  His  Phe  Ala  Ser  Gly  Thr  Leu  Ser  Ala  Arg  Thr  Ala  Ile  Arg  Thr
     370                     375                     380

Ala  Arg  Asp  Arg  Asn  Asn  Thr  Lys  Lys  Leu  Asn  Gly  Gly  Asn  Glu  Gly
385                      390                     395                     400

Ile  Gln  Arg  Trp  Ile  Ser  Glu  Val  Ala  Trp  Arg  Asp  Phe  Tyr  Lys  His
                    405                     410                     415

Val  Leu  Val  His  Trp  Pro  Tyr  Val  Cys  Met  Asn  Lys  Pro  Phe  Lys  Pro
               420                     425                     430

Thr  Tyr  Ser  Asn  Ile  Glu  Trp  Ser  Tyr  Asn  Val  Asp  His  Phe  His  Ala
          435                     440                     445

Trp  Thr  Gln  Gly  Arg  Thr  Gly  Phe  Pro  Ile  Ile  Asp  Ala  Ala  Met  Arg
     450                     455                     460

Gln  Val  Leu  Ser  Thr  Gly  Tyr  Met  His  Asn  Arg  Leu  Arg  Met  Ile  Val
465                      470                     475                     480

Ala  Ser  Phe  Leu  Ala  Lys  Asp  Leu  Leu  Val  Asp  Trp  Arg  Met  Gly  Glu
                    485                     490                     495

Arg  Tyr  Phe  Met  Glu  His  Leu  Ile  Asp  Gly  Asp  Phe  Ala  Ser  Asn  Asn
               500                     505                     510

Gly  Gly  Trp  Gly  Phe  Ala  Ala  Ser  Val  Gly  Val  Asp  Pro  Gln  Pro  Tyr
          515                     520                     525

Phe  Arg  Val  Phe  Asn  Pro  Leu  Leu  Gln  Ser  Glu  Lys  Phe  Asp  Pro  Asp
     530                     535                     540

Gly  Asp  Tyr  Ile  Arg  Lys  Trp  Val  Glu  Glu  Leu  Arg  Asp  Leu  Pro  Glu
545                      550                     555                     560

Leu  Lys  Gly  Gly  Lys  Gly  Gly  Glu  Ile  His  Asp  Pro  Tyr  Gly  Arg  Gly
                    565                     570                     575

Ser  Glu  Lys  Val  Lys  Lys  Lys  Leu  Glu  Glu  Lys  Gly  Tyr  Pro  Arg  Pro
               580                     585                     590
```

| Ile | Val | Glu | His | Ser | Gly | Ala | Arg | Asp | Arg | Ala | Leu | Asp | Ala | Tyr | Lys |
|---|---|---|---|---|---|---|---|---|---|---|---|---|---|---|---|
| | | 595 | | | | | 600 | | | | | 605 | | | |

| Arg | Gly | Leu | Ala | Arg | Asp | Leu |
|---|---|---|---|---|---|---|
| 610 | | | | | | 615 |

( 2 ) INFORMATION FOR SEQ ID NO:8:

( i ) SEQUENCE CHARACTERISTICS:
        ( A ) LENGTH: 566 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

| Met | Lys | Arg | Thr | Val | Ile | Ser | Ser | Ser | Asn | Ala | Tyr | Ala | Ser | Lys | Arg |
|---|---|---|---|---|---|---|---|---|---|---|---|---|---|---|---|
| 1 | | | | 5 | | | | | 10 | | | | | 15 | |

| Ser | Arg | Leu | Asp | Ile | Glu | His | Asp | Phe | Glu | Gln | Tyr | His | Ser | Leu | Asn |
|---|---|---|---|---|---|---|---|---|---|---|---|---|---|---|---|
| | | | 20 | | | | | 25 | | | | | 30 | | |

| Lys | Lys | Tyr | Tyr | Tyr | Pro | Arg | Pro | Ile | Thr | Arg | Thr | Gly | Ala | Asn | Gln |
|---|---|---|---|---|---|---|---|---|---|---|---|---|---|---|---|
| | | | 35 | | | | | 40 | | | | | 45 | | |

| Phe | Asn | Asn | Lys | Ser | Arg | Ala | Lys | Pro | Met | Glu | Ile | Val | Glu | Lys | Leu |
|---|---|---|---|---|---|---|---|---|---|---|---|---|---|---|---|
| | 50 | | | | | 55 | | | | | 60 | | | | |

| Gln | Lys | Lys | Gln | Lys | Thr | Ser | Phe | Glu | Asn | Val | Ser | Thr | Val | Met | His |
|---|---|---|---|---|---|---|---|---|---|---|---|---|---|---|---|
| 65 | | | | | 70 | | | | | 75 | | | | | 80 |

| Trp | Phe | Arg | Asn | Asp | Leu | Arg | Leu | Tyr | Asp | Asn | Val | Gly | Leu | Tyr | Lys |
|---|---|---|---|---|---|---|---|---|---|---|---|---|---|---|---|
| | | | | 85 | | | | | 90 | | | | | 95 | |

| Ser | Val | Ala | Leu | Phe | Gln | Gln | Leu | Arg | Gln | Lys | Asn | Ala | Lys | Ala | Lys |
|---|---|---|---|---|---|---|---|---|---|---|---|---|---|---|---|
| | | | 100 | | | | | 105 | | | | | 110 | | |

| Leu | Tyr | Ala | Val | Tyr | Val | Ile | Asn | Glu | Asp | Asp | Trp | Arg | Ala | His | Met |
|---|---|---|---|---|---|---|---|---|---|---|---|---|---|---|---|
| | | | 115 | | | | | 120 | | | | | 125 | | |

| Asp | Ser | Gly | Trp | Lys | Leu | Met | Phe | Ile | Met | Gly | Ala | Leu | Lys | Asn | Leu |
|---|---|---|---|---|---|---|---|---|---|---|---|---|---|---|---|
| | 130 | | | | | 135 | | | | | 140 | | | | |

| Gln | Gln | Ser | Leu | Ala | Glu | Leu | His | Ile | Pro | Leu | Leu | Leu | Trp | Glu | Phe |
|---|---|---|---|---|---|---|---|---|---|---|---|---|---|---|---|
| 145 | | | | | 150 | | | | | 155 | | | | | 160 |

| His | Thr | Pro | Lys | Ser | Ser | Leu | Ser | Asn | Thr | Lys | Glu | Phe | Val | Glu | Phe |
|---|---|---|---|---|---|---|---|---|---|---|---|---|---|---|---|
| | | | | 165 | | | | | 170 | | | | | 175 | |

| Phe | Lys | Glu | Lys | Cys | Met | Asn | Val | Ser | Ser | Gly | Thr | Gly | Thr | Ile | Ile |
|---|---|---|---|---|---|---|---|---|---|---|---|---|---|---|---|
| | | | 180 | | | | | 185 | | | | | 190 | | |

| Thr | Ala | Asn | Ile | Glu | Tyr | Gln | Thr | Ser | Glu | Leu | Tyr | Arg | Asp | Ile | Arg |
|---|---|---|---|---|---|---|---|---|---|---|---|---|---|---|---|
| | | 195 | | | | | 200 | | | | | 205 | | | |

| Leu | Leu | Glu | Asn | Glu | Asp | His | Arg | Leu | Gln | Leu | Lys | Tyr | Tyr | His | Asp |
|---|---|---|---|---|---|---|---|---|---|---|---|---|---|---|---|
| | 210 | | | | | 215 | | | | | 220 | | | | |

| Ser | Cys | Ile | Val | Ala | Pro | Gly | Leu | Ile | Thr | Thr | Asp | Arg | Gly | Thr | Asn |
|---|---|---|---|---|---|---|---|---|---|---|---|---|---|---|---|
| 225 | | | | | 230 | | | | | 235 | | | | | 240 |

| Tyr | Ser | Val | Phe | Thr | Pro | Trp | Tyr | Lys | Lys | Trp | Val | Leu | Tyr | Val | Asn |
|---|---|---|---|---|---|---|---|---|---|---|---|---|---|---|---|
| | | | | 245 | | | | | 250 | | | | | 255 | |

| Asn | Tyr | Lys | Lys | Ser | Thr | Ser | Glu | Ile | Cys | His | Leu | His | Ile | Ile | Glu |
|---|---|---|---|---|---|---|---|---|---|---|---|---|---|---|---|
| | | | 260 | | | | | 265 | | | | | 270 | | |

| Pro | Leu | Lys | Tyr | Asn | Glu | Thr | Phe | Glu | Leu | Lys | Pro | Phe | Gln | Tyr | Ser |
|---|---|---|---|---|---|---|---|---|---|---|---|---|---|---|---|
| | | 275 | | | | | 280 | | | | | 285 | | | |

| Leu | Pro | Asp | Glu | Phe | Leu | Gln | Tyr | Ile | Pro | Lys | Ser | Lys | Trp | Cys | Leu |
|---|---|---|---|---|---|---|---|---|---|---|---|---|---|---|---|
| | 290 | | | | | 295 | | | | | 300 | | | | |

| Pro | Asp | Val | Ser | Glu | Glu | Ala | Ala | Leu | Ser | Arg | Leu | Lys | Asp | Phe | Leu |
|---|---|---|---|---|---|---|---|---|---|---|---|---|---|---|---|
| 305 | | | | | 310 | | | | | 315 | | | | | 320 |

| Gly | Thr | Lys | Ser | Ser | Lys | Tyr | Asn | Asn | Glu | Lys | Asp | Met | Leu | Tyr | Leu |
|---|---|---|---|---|---|---|---|---|---|---|---|---|---|---|---|

```
                                   325                         330                         335
        Gly   Gly   Thr   Ser   Gly   Leu   Ser   Val   Tyr   Ile   Thr   Thr   Gly   Arg   Ile   Arg
                          340                         345                         350

Thr   Arg   Leu   Ile   Val   Asn   Gln   Ala   Phe   Gln   Ser   Cys   Asn   Glu   Gln   Ile
                    355                         360                         365

Met   Ser   Lys   Ala   Leu   Lys   Asp   Asn   Ser   Ser   Thr   Gln   Asn   Phe   Ile   Lys
                    370                         375                         380

Glu   Val   Ala   Trp   Arg   Asp   Phe   Tyr   Arg   His   Cys   Met   Cys   Asn   Trp   Pro
        385                         390                         395                               400

Tyr   Thr   Ser   Met   Gly   Met   Pro   Tyr   Arg   Leu   Asp   Thr   Leu   Asp   Ile   Lys
                                405                         410                         415

Trp   Glu   Asn   Asn   Pro   Val   Ala   Phe   Glu   Lys   Trp   Cys   Thr   Gly   Asn   Thr
                          420                         425                         430

Gly   Ile   Pro   Ile   Val   Asp   Ala   Ile   Met   Arg   Lys   Leu   Leu   Tyr   Thr   Gly
                          435                         440                         445

Tyr   Ile   Asn   Asn   Arg   Ser   Arg   Met   Ile   Thr   Ala   Ser   Phe   Leu   Ser   Lys
                    450                         455                         460

Asn   Leu   Leu   Ile   Asp   Trp   Arg   Trp   Gly   Lys   Arg   Trp   Phe   Met   Lys   His
        465                         470                         475                               480

Leu   Ile   Asp   Gly   Asp   Ser   Ser   Asn   Val   Gly   Gly   Trp   Gly   Phe   Cys
                                485                         490                         495

Ser   Ser   Thr   Gly   Ile   Asp   Ala   Gln   Pro   Tyr   Phe   Arg   Val   Phe   Asn   Met
                          500                         505                         510

Asp   Ile   Gln   Ala   Lys   Lys   Tyr   Asp   Pro   Gln   Met   Ile   Phe   Val   Lys   Gln
                    515                         520                         525

Trp   Val   Pro   Glu   Leu   Ile   Ser   Ser   Glu   Asn   Lys   Arg   Pro   Glu   Asn   Tyr
                    530                         535                         540

Pro   Lys   Pro   Leu   Val   Asp   Leu   Lys   His   Ser   Arg   Glu   Arg   Ala   Leu   Lys
        545                         550                         555                               560

Val   Tyr   Lys   Asp   Ala   Met
                          565
```

(2) INFORMATION FOR SEQ ID NO:9:

(i) SEQUENCE CHARACTERISTICS:
        (A) LENGTH: 681 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
        Met   Ser   Gly   Ser   Val   Ser   Gly   Cys   Gly   Ser   Gly   Gly   Cys   Ser   Ile   Val
        1                       5                         10                              15

Trp   Phe   Arg   Arg   Asp   Leu   Arg   Val   Glu   Asp   Asn   Pro   Ala   Leu   Ala   Ala
                          20                          25                          30

Ala   Val   Arg   Ala   Gly   Pro   Val   Ile   Ala   Leu   Phe   Val   Trp   Ala   Pro   Glu
                    35                          40                          45

Glu   Glu   Gly   His   Tyr   His   Pro   Gly   Arg   Val   Ser   Arg   Trp   Trp   Leu   Lys
                    50                          55                          60

Asn   Ser   Leu   Ala   Gln   Leu   Asp   Ser   Ser   Leu   Arg   Ser   Leu   Gly   Thr   Cys
        65                          70                          75                              80

Leu   Ile   Thr   Lys   Arg   Ser   Thr   Asp   Ser   Val   Ala   Ser   Leu   Leu   Asp   Val
                          85                          90                          95

Val   Lys   Ser   Thr   Gly   Ala   Ser   Gln   Ile   Phe   Phe   Asn   His   Leu   Tyr   Asp
                          100                         105                         110
```

```
Pro  Leu  Ser  Leu  Val  Arg  Asp  His  Arg  Ala  Lys  Asp  Val  Leu  Thr  Ala
          115                 120                      125

Gln  Gly  Ile  Ala  Val  Arg  Ser  Phe  Asn  Ala  Asp  Leu  Leu  Tyr  Glu  Pro
     130                 135                      140

Trp  Glu  Val  Thr  Asp  Glu  Leu  Gly  Arg  Pro  Phe  Ser  Met  Phe  Ala  Ala
145                      150                 155                           160

Phe  Trp  Glu  Arg  Cys  Leu  Ser  Met  Pro  Tyr  Asp  Pro  Glu  Ser  Pro  Leu
               165                      170                           175

Leu  Pro  Pro  Lys  Lys  Ile  Ile  Ser  Gly  Asp  Val  Ser  Lys  Cys  Val  Ala
               180                 185                      190

Asp  Pro  Leu  Val  Phe  Glu  Asp  Asp  Ser  Glu  Lys  Gly  Ser  Asn  Ala  Leu
          195                 200                      205

Leu  Ala  Arg  Ala  Trp  Ser  Pro  Gly  Trp  Ser  Asn  Gly  Asp  Lys  Ala  Leu
          210                 215                      220

Thr  Thr  Phe  Ile  Asn  Gly  Pro  Leu  Leu  Glu  Tyr  Ser  Lys  Asn  Arg  Arg
225                      230                 235                           240

Lys  Ala  Asp  Ser  Ala  Thr  Thr  Ser  Phe  Leu  Ser  Pro  His  Leu  His  Phe
               245                      250                           255

Gly  Glu  Val  Ser  Val  Arg  Lys  Val  Phe  His  Leu  Val  Arg  Ile  Lys  Gln
               260                 265                      270

Val  Ala  Trp  Ala  Asn  Glu  Gly  Asn  Glu  Ala  Gly  Glu  Glu  Ser  Val  Asn
          275                 280                      285

Leu  Phe  Leu  Lys  Ser  Ile  Gly  Leu  Arg  Glu  Tyr  Ser  Arg  Tyr  Ile  Ser
     290                 295                      300

Phe  Asn  His  Pro  Tyr  Ser  His  Glu  Arg  Pro  Leu  Leu  Gly  His  Leu  Lys
305                      310                 315                           320

Phe  Phe  Pro  Trp  Ala  Val  Asp  Glu  Asn  Tyr  Phe  Lys  Ala  Trp  Arg  Gln
               325                      330                           335

Gly  Arg  Thr  Gly  Tyr  Pro  Leu  Val  Asp  Ala  Gly  Met  Arg  Glu  Leu  Trp
               340                      345                           350

Ala  Thr  Gly  Trp  Leu  His  Asp  Arg  Ile  Arg  Val  Val  Val  Ser  Ser  Phe
               355                      360                      365

Phe  Val  Lys  Val  Leu  Gln  Leu  Pro  Trp  Arg  Trp  Gly  Met  Lys  Tyr  Phe
     370                 375                      380

Trp  Asp  Thr  Leu  Leu  Asp  Ala  Asp  Leu  Glu  Ser  Asp  Ala  Leu  Gly  Trp
385                      390                 395                           400

Gln  Tyr  Ile  Thr  Gly  Thr  Leu  Pro  Asp  Ser  Arg  Glu  Phe  Asp  Arg  Ile
               405                      410                           415

Asp  Asn  Pro  Gln  Phe  Glu  Gly  Tyr  Lys  Phe  Asp  Pro  Asn  Gly  Glu  Tyr
               420                      425                      430

Val  Arg  Arg  Trp  Leu  Pro  Glu  Leu  Ser  Arg  Leu  Pro  Thr  Asp  Trp  Ile
          435                      440                 445

His  His  Pro  Trp  Asn  Ala  Pro  Glu  Ser  Val  Leu  Gln  Ala  Ala  Gly  Ile
          450                      455                 460

Glu  Leu  Gly  Ser  Asn  Tyr  Pro  Leu  Pro  Ile  Val  Gly  Leu  Asp  Glu  Ala
465                      470                      475                      480

Lys  Ala  Arg  Leu  His  Glu  Ala  Leu  Ser  Gln  Met  Trp  Gln  Leu  Glu  Ala
               485                      490                           495

Ala  Ser  Arg  Ala  Ala  Ile  Glu  Asn  Gly  Ser  Glu  Gly  Gly  Leu  Gly  Asp
               500                      505                           510

Ser  Ala  Glu  Val  Glu  Glu  Ala  Pro  Ile  Glu  Phe  Pro  Arg  Asp  Ile  Thr
          515                      520                      525

Met  Glu  Glu  Thr  Glu  Pro  Thr  Arg  Leu  Asn  Pro  Asn  Arg  Arg  Tyr  Glu
```

-continued

|   |   |   | 530 |   |   |   | 535 |   |   |   | 540 |   |   |   |
|---|---|---|---|---|---|---|---|---|---|---|---|---|---|---|
| Asp<br>545 | Gln | Met | Val | Pro | Ser<br>550 | Ile | Thr | Ser | Ser<br>555 | Leu | Ile | Arg | Pro | Glu<br>560 | Glu |
| Asp | Glu | Glu | Ser | Ser<br>565 | Leu | Asn | Leu | Arg<br>570 | Asn | Ser | Val | Gly | Asp<br>575 | Ser | Arg |
| Ala | Glu | Val | Pro<br>580 | Arg | Asn | Met | Val | Asn<br>585 | Thr | Asn | Gln | Ala | Gln<br>590 | Gln | Arg |
| Arg | Ala | Glu<br>595 | Pro | Ala | Ser | Asn | Gln<br>600 | Val | Thr | Ala | Met | Ile<br>605 | Pro | Glu | Phe |
| Asn | Ile | Arg<br>610 | Ile | Val | Ala | Glu<br>615 | Ser | Thr | Glu | Asp | Ser<br>620 | Thr | Ala | Glu | Ser |
| Ser<br>625 | Ser | Ser | Gly | Arg | Arg<br>630 | Glu | Arg | Ser | Gly | Gly<br>635 | Ile | Val | Pro | Glu | Trp<br>640 |
| Ser | Pro | Gly | Tyr | Ser<br>645 | Glu | Gln | Phe | Pro | Ser<br>650 | Glu | Glu | Asn | Arg | Ile<br>655 | Gly |
| Gly | Gly | Ser | Thr<br>660 | Thr | Ser | Ser | Tyr | Leu<br>665 | Gln | Asn | His | His | Glu<br>670 | Ile | Leu |
| Asn | Trp | Arg<br>675 | Arg | Leu | Ser | Gln | Thr<br>680 | Gly |   |   |   |   |   |   |   |

( 2 ) INFORMATION FOR SEQ ID NO:10:

( i ) SEQUENCE CHARACTERISTICS:
  ( A ) LENGTH: 472 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:10:

|   |   |   |   |   |   |   |   |   |   |   |   |   |   |   |   |
|---|---|---|---|---|---|---|---|---|---|---|---|---|---|---|---|
| Met<br>1 | Thr | Thr | His | Leu<br>5 | Val | Trp | Phe | Arg | Gln<br>10 | Asp | Leu | Arg | Leu | His<br>15 | Asp |
| Asn | Leu | Ala | Leu<br>20 | Ala | Ala | Ala | Cys<br>25 | Arg | Asn | Ser | Ser | Ala | Arg<br>30 | Val | Leu |
| Ala | Leu | Tyr<br>35 | Ile | Ala | Thr | Pro<br>40 | Arg | Gln | Trp | Ala | Thr<br>45 | His | Asn | Met | Ser |
| Pro | Arg<br>50 | Gln | Ala | Glu | Leu | Ile<br>55 | Asn | Ala | Gln | Leu | Asn<br>60 | Gly | Leu | Gln | Ile |
| Ala<br>65 | Leu | Ala | Glu | Lys | Gly<br>70 | Ile | Pro | Leu | Leu | Phe<br>75 | Arg | Glu | Val | Asp | Asp<br>80 |
| Phe | Val | Ala | Ser | Val<br>85 | Glu | Ile | Val | Lys | Gln<br>90 | Val | Cys | Ala | Glu | Asn<br>95 | Ser |
| Val | Thr | His | Leu<br>100 | Phe | Tyr | Asn | Tyr | Gln<br>105 | Tyr | Glu | Val | Asn | Glu<br>110 | Arg | Ala |
| Arg | Asp | Val<br>115 | Glu | Val | Glu | Arg<br>120 | Ala | Leu | Arg | Asn | Val<br>125 | Val | Cys | Glu | Gly |
| Phe | Asp<br>130 | Asp | Ser | Val | Ile | Leu<br>135 | Pro | Pro | Gly | Ala | Val<br>140 | Met | Thr | Gly | Asn |
| His<br>145 | Glu | Met | Tyr | Lys | Val<br>150 | Phe | Thr | Pro | Phe | Lys<br>155 | Asn | Ala | Trp | Leu | Lys<br>160 |
| Arg | Leu | Arg | Glu | Gly<br>165 | Met | Pro | Glu | Cys | Val<br>170 | Ala | Ala | Pro | Lys | Val<br>175 | Arg |
| Ser | Ser | Gly | Ser<br>180 | Ile | Glu | Pro | Ser | Pro<br>185 | Ser | Ile | Thr | Leu | Asn<br>190 | Tyr | Pro |
| Arg | Gln | Ser<br>195 | Phe | Asp | Thr | Ala | His<br>200 | Phe | Pro | Val | Glu | Glu<br>205 | Lys | Ala | Ala |

```
Ile  Ala  Gln  Leu  Arg  Gln  Phe  Cys  Gln  Asn  Gly  Ala  Gly  Glu  Tyr  Glu
     210                      215                      220

Gln  Gln  Arg  Asp  Phe  Pro  Ala  Val  Glu  Gly  Thr  Ser  Arg  Leu  Ser  Ala
225                           230                      235                      240

Ser  Leu  Ala  Thr  Gly  Gly  Leu  Ser  Pro  Arg  Gln  Cys  Leu  His  Arg  Leu
                    245                      250                      255

Leu  Ala  Glu  Gln  Pro  Gln  Ala  Leu  Asp  Gly  Gly  Ala  Gly  Ser  Val  Trp
               260                      265                      270

Leu  Asn  Glu  Leu  Ile  Trp  Arg  Glu  Phe  Tyr  Arg  His  Leu  Ile  Thr  Tyr
          275                      280                      285

His  Pro  Ser  Leu  Cys  Lys  His  Arg  Pro  Phe  Ile  Ala  Trp  Thr  Asp  Arg
     290                      295                      300

Val  Gln  Trp  Gln  Ser  Asn  Pro  Ala  His  Leu  Gln  Ala  Trp  Gln  Glu  Gly
305                           310                      315                      320

Lys  Thr  Gly  Tyr  Pro  Ile  Val  Asp  Ala  Ala  Met  Arg  Gln  Leu  Asn  Ser
                    325                      330                      335

Thr  Gly  Trp  Met  His  Asn  Arg  Leu  Arg  Met  Ile  Thr  Ala  Ser  Phe  Leu
               340                      345                      350

Val  Lys  Asp  Leu  Leu  Ile  Asp  Trp  Arg  Glu  Gly  Glu  Arg  Tyr  Phe  Met
          355                      360                      365

Ser  Gln  Leu  Ile  Asp  Gly  Asp  Leu  Ala  Ala  Asn  Gly  Gly  Trp  Gln
     370                      375                      380

Trp  Ala  Ala  Ser  Thr  Gly  Thr  Asp  Ala  Ala  Pro  Tyr  Phe  Arg  Ile  Phe
385                      390                      395                      400

Asn  Pro  Thr  Thr  Gln  Gly  Glu  Lys  Phe  Asp  His  Glu  Gly  Glu  Phe  Ile
                    405                      410                      415

Arg  Gln  Trp  Leu  Pro  Glu  Leu  Arg  Asp  Val  Pro  Gly  Lys  Val  Val  His
               420                      425                      430

Glu  Pro  Trp  Lys  Trp  Ala  Gln  Lys  Ala  Gly  Val  Thr  Leu  Asp  Tyr  Pro
          435                      440                      445

Gln  Pro  Ile  Val  Glu  His  Lys  Glu  Ala  Arg  Val  Gln  Thr  Leu  Ala  Ala
     450                      455                      460

Tyr  Glu  Ala  Ala  Arg  Lys  Gly  Lys
465                      470
```

( 2 ) INFORMATION FOR SEQ ID NO:11:

( i ) SEQUENCE CHARACTERISTICS:
        ( A ) LENGTH: 473 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met  Pro  Thr  His  Leu  Val  Trp  Phe  Arg  Arg  Asp  Leu  Arg  Leu  Gln  Asp
1                        5                   10                       15

Asn  Leu  Ala  Leu  Ala  Ala  Ala  Cys  Arg  Asp  Ala  Ser  Ala  Arg  Val  Leu
               20                      25                      30

Ala  Leu  Tyr  Ile  Ser  Thr  Pro  Ala  Gln  Trp  Gln  Ala  His  Asp  Met  Ala
          35                      40                      45

Pro  Arg  Gln  Ala  Ala  Phe  Ile  Ser  Ala  Gln  Leu  Asn  Ala  Leu  Gln  Thr
     50                      55                      60

Ala  Leu  Ala  Glu  Lys  Gly  Ile  Pro  Leu  Leu  Phe  His  Glu  Val  Ala  Asp
65                       70                      75                      80
```

```
Phe  Asn  Ala  Ser  Ile  Glu  Thr  Val  Lys  Asn  Val  Cys  Arg  Gln  His  Asp
                    85                  90                       95

Val  Ser  His  Leu  Phe  Tyr  Asn  Tyr  Gln  Tyr  Glu  Phe  Asn  Glu  Arg  Gln
               100                 105                      110

Arg  Asp  Arg  Ala  Val  Glu  Lys  Thr  Leu  Pro  Ser  Val  Ile  Cys  Glu  Gly
          115                      120                      125

Phe  Asp  Asp  Ser  Val  Ile  Leu  Ala  Pro  Gly  Ala  Val  Met  Thr  Gly  Asn
     130                      135                      140

His  Glu  Met  Tyr  Lys  Val  Phe  Thr  Pro  Phe  Lys  Asn  Ala  Trp  Leu  Lys
145                      150                      155                      160

Arg  Leu  Lys  Glu  Asp  Ile  Pro  Pro  Cys  Val  Pro  Ala  Pro  Lys  Ile  Arg
                    165                      170                      175

Val  Ser  Gly  Ala  Leu  Ser  Thr  Pro  Leu  Thr  Pro  Val  Ser  Leu  Asn  Tyr
               180                      185                      190

Pro  Gln  Gln  Glu  Phe  Asp  Thr  Ala  Leu  Phe  Pro  Val  Glu  Glu  Asn  Ala
          195                      200                      205

Val  Ile  Ala  Gln  Leu  Arg  Gln  Phe  Cys  Ala  Gln  Gly  Ala  Asp  Leu  Tyr
     210                      215                      220

Ala  Leu  Arg  Arg  Asp  Phe  Pro  Ala  Val  Asp  Gly  Thr  Ser  Arg  Leu  Ser
225                      230                      235                      240

Ala  Ser  Leu  Ala  Thr  Gly  Gly  Leu  Ser  Pro  Arg  Gln  Cys  Leu  His  Arg
                    245                      250                      255

Leu  Leu  Ala  Glu  Gln  Pro  Gln  Ala  Leu  Asp  Gly  Gly  Pro  Gly  Ser  Val
               260                      265                      270

Trp  Leu  Asn  Glu  Leu  Ile  Trp  Arg  Glu  Phe  Tyr  Arg  His  Leu  Met  Thr
          275                      280                      285

Trp  Tyr  Pro  Ala  Leu  Cys  Lys  His  Gln  Pro  Phe  Ile  Arg  Trp  Thr  Lys
     290                      295                      300

Arg  Val  Ala  Trp  Gln  Glu  Asn  Pro  His  Tyr  Phe  Gln  Ala  Trp  Gln  Lys
305                      310                      315                      320

Gly  Glu  Thr  Gly  Tyr  Pro  Ile  Val  Asp  Ala  Ala  Met  Arg  Gln  Leu  Asn
                    325                      330                      335

Ala  Thr  Gly  Trp  Met  His  Asn  Arg  Leu  Arg  Met  Ile  Thr  Ala  Ser  Phe
               340                      345                      350

Leu  Val  Lys  Asp  Leu  Leu  Ile  Asp  Trp  Arg  Leu  Gly  Glu  Arg  Tyr  Phe
          355                      360                      365

Met  Ser  Gln  Leu  Ile  Asp  Gly  Asp  Leu  Ala  Ala  Asn  Asn  Gly  Gly  Trp
     370                      375                      380

Gln  Trp  Ala  Ala  Ser  Thr  Gly  Thr  Asp  Ala  Ala  Pro  Tyr  Phe  Arg  Ile
385                      390                      395                      400

Phe  Asn  Pro  Thr  Thr  Gln  Gly  Glu  Arg  Phe  Asp  Arg  Asp  Gly  Glu  Phe
                    405                      410                      415

Ile  Arg  Gln  Trp  Leu  Pro  Ala  Leu  Arg  Asp  Ile  Pro  Gly  Lys  Ala  Ile
               420                      425                      430

His  Glu  Pro  Trp  Arg  Trp  Ala  Glu  Lys  Ala  Gly  Val  Val  Leu  Asp  Tyr
          435                      440                      445

Pro  Arg  Pro  Ile  Val  Glu  His  Lys  Gln  Ala  Arg  Ile  Ala  Thr  Leu  Ser
     450                      455                      460

Ala  Tyr  Glu  Ala  Ala  Arg  Lys  Gly  Ala
465                      470
```

( 2 ) INFORMATION FOR SEQ ID NO:12:

( i ) SEQUENCE CHARACTERISTICS:

( A ) LENGTH: 480 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:12:

| Met | Gln | Leu | Phe | Trp | His | Arg | Arg | Asp | Leu | Arg | Thr | Thr | Asp | Asn | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Leu | Ala | Ala | Ala | Ala | Pro | Gly | Val | Thr | Ala | Val | Asp | Gly | Gly | His |
|     |     |     |     | 20  |     |     |     | 25  |     |     |     |     | 30  |     |     |

| Asp | Gln | Gly | Pro | Val | Ala | Ala | Val | Phe | Cys | Phe | Asp | Asp | Glu | Val | Leu |
|     |     | 35  |     |     |     |     | 40  |     |     |     |     | 45  |     |     |     |

| Ala | His | Ala | Ala | Pro | Pro | Arg | Val | Ala | Phe | Met | Leu | Asp | Ala | Leu | Ala |
|     | 50  |     |     |     |     | 55  |     |     |     |     | 60  |     |     |     |     |

| Ala | Leu | Arg | Glu | Arg | Tyr | Arg | Asp | Leu | Gly | Ser | Asp | Leu | Ile | Val | Arg |
| 65  |     |     |     |     | 70  |     |     |     |     | 75  |     |     |     |     | 80  |

| His | Gly | Asp | Pro | Ala | Ala | Val | Leu | Pro | Val | Ala | Asn | Asp | Leu | Asp |
|     |     |     |     | 85  |     |     |     |     | 90  |     |     |     |     | 95  |

| Ala | Thr | Arg | Val | Val | Trp | Asn | His | Asp | Tyr | Ser | Gly | Leu | Ala | Thr | Asp |
|     |     |     | 100 |     |     |     |     | 105 |     |     |     |     | 110 |     |     |

| Arg | Asp | Ala | Gly | Val | Arg | Asp | Ala | Leu | Asp | Ala | Ala | Gly | Val | Ala | His |
|     |     |     | 115 |     |     |     |     | 120 |     |     |     |     | 125 |     |     |

| Ala | Gln | Phe | His | Asp | Ala | Val | His | His | Arg | Pro | Gly | Glu | Ile | Arg | Thr |
|     |     | 130 |     |     |     |     | 135 |     |     |     |     | 140 |     |     |     |

| Asn | Ala | Gly | Asp | Pro | Tyr | Ser | Val | Tyr | Thr | Tyr | Phe | Trp | Arg | Lys | Trp |
| 145 |     |     |     |     | 150 |     |     |     |     | 155 |     |     |     |     | 160 |

| Gln | Asp | Arg | Glu | Lys | Asn | Pro | Pro | Ala | Pro | Glu | Pro | Glu | Pro | Ala | Asp |
|     |     |     |     | 165 |     |     |     |     | 170 |     |     |     |     | 175 |     |

| Leu | Ala | Ala | Asp | Thr | Ala | Leu | Ala | Asp | Thr | Ser | Pro | Leu | Pro | Ser | Val |
|     |     |     | 180 |     |     |     |     | 185 |     |     |     |     | 190 |     |     |

| Gln | Glu | Leu | Gly | Phe | Ala | Glu | Pro | Glu | Ala | Ala | Val | Pro | Asp | Ala | Gly |
|     |     | 195 |     |     |     |     | 200 |     |     |     |     | 205 |     |     |     |

| Thr | Ala | Ala | Ala | Arg | Ser | Leu | Leu | Asp | Ala | Phe | Arg | Glu | Ser | Gly | Asp |
|     | 210 |     |     |     |     | 215 |     |     |     |     | 220 |     |     |     |     |

| Ile | Tyr | Arg | Tyr | Glu | Asp | Arg | Arg | Asp | Tyr | Pro | His | Glu | Glu | Pro | Thr |
| 225 |     |     |     |     | 230 |     |     |     |     | 235 |     |     |     |     | 240 |

| Ser | Arg | Leu | Ser | Pro | His | Leu | Lys | Phe | Gly | Thr | Ile | Gly | Ile | Arg | Thr |
|     |     |     |     | 245 |     |     |     |     | 250 |     |     |     |     | 255 |     |

| Val | Tyr | Glu | Ala | Ala | Arg | Ala | Ala | Lys | Ser | Asp | Ala | Asp | Thr | Asp | Asp |
|     |     |     | 260 |     |     |     |     | 265 |     |     |     |     | 270 |     |     |

| Glu | Arg | Glu | Asn | Val | Ala | Ala | Phe | Ile | Gly | Gln | Leu | Ala | Trp | Arg | Glu |
|     |     | 275 |     |     |     |     | 280 |     |     |     |     | 285 |     |     |     |

| Phe | Tyr | Ala | Gln | Val | Leu | Tyr | Phe | Asn | Gln | Asn | Val | Val | Ser | Glu | Asn |
|     | 290 |     |     |     |     | 295 |     |     |     |     | 300 |     |     |     |     |

| Phe | Lys | Ala | Tyr | Glu | His | Pro | Ile | Glu | Trp | Arg | Asp | Pro | Ala | Ala |
| 305 |     |     |     |     | 310 |     |     |     |     | 315 |     |     |     | 320 |

| Leu | Gln | Ala | Trp | Lys | Asp | Gly | Glu | Thr | Gly | Tyr | Pro | Ile | Val | Asp | Ala |
|     |     |     |     | 325 |     |     |     |     | 330 |     |     |     |     | 335 |     |

| Gly | Met | Arg | Gln | Leu | Arg | Ala | Glu | Ala | Tyr | Met | His | Asn | Arg | Val | Arg |
|     |     |     | 340 |     |     |     |     | 345 |     |     |     |     | 350 |     |     |

| Met | Ile | Val | Ala | Ala | Phe | Leu | Thr | Lys | Asp | Leu | Ile | Val | Asp | Trp | Arg |
|     |     | 355 |     |     |     |     | 360 |     |     |     |     | 365 |     |     |     |

| Ala | Gly | Tyr | Asp | Trp | Phe | Arg | Glu | Lys | Leu | Ala | Asp | His | Asp | Thr | Ala |
|     | 370 |     |     |     |     | 375 |     |     |     |     | 380 |     |     |     |     |

-continued

| Asn<br>385 | Asp | Asn | Gly | Trp<br>390 | Gln | Trp | Ala | Ala | Ser<br>395 | Thr | Gly | Thr | Asp | Ala<br>400 | Gln |
| --- | --- | --- | --- | --- | --- | --- | --- | --- | --- | --- | --- | --- | --- | --- | --- |
| Pro | Tyr | Phe | Arg | Val<br>405 | Phe | Asn | Pro | Met | Thr<br>410 | Gln | Gly | Glu | Arg | Tyr<br>415 | Asp |
| Pro | Asp | Ala | Asp<br>420 | Tyr | Ile | Thr | Glu | Phe<br>425 | Val | Pro | Glu | Leu | Arg<br>430 | Asp | Val |
| Pro | Ala | Asp | Ala<br>435 | Ile | His | Ser | Trp | His<br>440 | Glu | Leu | Ser | Leu | Ser<br>445 | Glu | Arg |
| Arg | Arg | His<br>450 | Ala | Pro | Glu | Tyr | Pro<br>455 | Asp | Pro | Ile | Val | Asp<br>460 | His | Ser | Gln |
| Arg<br>465 | Arg | Glu | Asp | Ala | Ile<br>470 | Ala | Met | Phe | Glu | Arg<br>475 | Ala | Arg | Gly | Asp | Leu<br>480 |

( 2 ) INFORMATION FOR SEQ ID NO:13:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

| Met<br>1 | Ala | Ala | Pro | Ile<br>5 | Leu | Phe | Trp | His | Arg<br>10 | Arg | Asp | Leu | Arg | Leu<br>15 | Ser |
| --- | --- | --- | --- | --- | --- | --- | --- | --- | --- | --- | --- | --- | --- | --- | --- |
| Asp | Asn | Ile | Gly<br>20 | Leu | Ala | Ala | Ala | Arg<br>25 | Ala | Gln | Ser | Ala | Gln<br>30 | Leu | Ile |
| Gly | Leu | Phe<br>35 | Cys | Leu | Asp | Pro | Gln<br>40 | Ile | Leu | Gln | Ser | Ala<br>45 | Asp | Met | Ala |
| Pro | Ala<br>50 | Arg | Val | Ala | Tyr | Leu<br>55 | Gln | Gly | Cys | Leu | Gln<br>60 | Glu | Leu | Gln | Gln |
| Arg<br>65 | Tyr | Gln | Gln | Ala | Gly<br>70 | Ser | Arg | Leu | Leu | Leu<br>75 | Leu | Gln | Gly | Asp | Pro<br>80 |
| Gln | His | Leu | Ile | Pro<br>85 | Gln | Leu | Ala | Gln | Gln<br>90 | Leu | Gln | Ala | Glu | Ala<br>95 | Val |
| Tyr | Trp | Asn | Gln<br>100 | Asp | Ile | Glu | Pro | Tyr<br>105 | Gly | Arg | Asp | Arg | Asp<br>110 | Gly | Gln |
| Val | Ala | Ala | Ala<br>115 | Leu | Lys | Thr | Ala<br>120 | Gly | Ile | Arg | Ala | Val<br>125 | Gln | Leu | Trp |
| Asp | Gln | Leu<br>130 | Leu | His | Ser | Pro | Asp<br>135 | Gln | Ile | Leu | Ser | Gly<br>140 | Ser | Gly | Asn |
| Pro<br>145 | Tyr | Ser | Val | Tyr | Gly<br>150 | Pro | Phe | Trp | Lys | Asn<br>155 | Trp | Gln | Ala | Gln | Pro<br>160 |
| Lys | Pro | Thr | Pro | Val<br>165 | Ala | Thr | Pro | Thr | Glu<br>170 | Leu | Val | Asp | Leu | Ser<br>175 | Pro |
| Glu | Gln | Leu | Thr<br>180 | Ala | Ile | Ala | Pro | Leu<br>185 | Leu | Leu | Ser | Glu | Leu<br>190 | Pro | Thr |
| Leu | Lys | Gln<br>195 | Leu | Gly | Phe | Asp | Trp<br>200 | Asp | Gly | Gly | Phe | Pro<br>205 | Val | Glu | Pro |
| Gly | Glu<br>210 | Thr | Ala | Ala | Ile | Ala<br>215 | Arg | Leu | Gln | Glu | Phe<br>220 | Cys | Asp | Arg | Ala |
| Ile<br>225 | Ala | Asp | Tyr | Asp | Pro<br>230 | Gln | Arg | Asn | Phe | Pro<br>235 | Ala | Glu | Ala | Gly | Thr<br>240 |
| Ser | Gly | Leu | Ser | Pro<br>245 | Ala | Leu | Lys | Phe | Gly<br>250 | Ala | Ile | Gly | Ile | Arg<br>255 | Gln |
| Ala | Trp | Gln | Ala | Ala | Ser | Ala | Ala | His | Ala | Leu | Ser | Arg | Ser | Asp | Glu |

```
                                  260                       265                        270
        Ala  Arg  Asn  Ser  Ile  Arg  Val  Trp  Gln  Gln  Glu  Leu  Ala  Trp  Arg  Glu
                  275                       280                       285

Phe  Tyr  Gln  His  Ala  Leu  Tyr  His  Phe  Pro  Ser  Leu  Ala  Asp  Gly  Pro
        290                       295                       300

Tyr  Arg  Ser  Leu  Trp  Gln  Gln  Phe  Pro  Trp  Glu  Asn  Arg  Glu  Ala  Leu
        305                       310                       315                       320

Phe  Thr  Ala  Trp  Thr  Gln  Ala  Gln  Thr  Gly  Tyr  Pro  Ile  Val  Asp  Ala
                            325                       330                            335

Ala  Met  Arg  Gln  Leu  Thr  Glu  Thr  Gly  Trp  Met  His  Asn  Arg  Cys  Arg
                       340                       345                       350

Met  Ile  Val  Ala  Ser  Phe  Leu  Thr  Lys  Asp  Leu  Ile  Ile  Asp  Trp  Arg
                       355                       360                       365

Arg  Gly  Glu  Gln  Phe  Phe  Met  Gln  His  Leu  Val  Asp  Gly  Asp  Leu  Ala
        370                       375                       380

Ala  Asn  Asn  Gly  Gly  Trp  Gln  Trp  Ser  Ala  Ser  Ser  Gly  Met  Asp  Pro
        385                       390                       395                       400

Lys  Pro  Leu  Arg  Ile  Phe  Asn  Pro  Ala  Ser  Gln  Ala  Lys  Lys  Phe  Asp
                            405                       410                       415

Ala  Thr  Ala  Thr  Tyr  Ile  Lys  Arg  Trp  Leu  Pro  Glu  Leu  Arg  His  Val
                       420                       425                       430

His  Pro  Lys  Asp  Leu  Ile  Ser  Gly  Glu  Ile  Thr  Pro  Ile  Glu  Arg  Arg
                       435                       440                       445

Gly  Tyr  Pro  Ala  Pro  Ile  Val  Asn  His  Asn  Leu  Arg  Gln  Lys  Gln  Phe
                  450                       455                       460

Lys  Ala  Met  Phe  Ala  Arg  Ala  Arg  Gly  Asp  Leu
        465                       470                       475
```

( 2 ) INFORMATION FOR SEQ ID NO:14:

( i ) SEQUENCE CHARACTERISTICS:
        ( A ) LENGTH: 455 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
        Met  Ser  Val  Ala  Val  Val  Leu  Phe  Thr  Ser  Asp  Leu  Arg  Leu  His  Asp
        1              5                        10                       15

Asn  Pro  Val  Leu  Arg  Ala  Ala  Leu  Arg  Asp  Ala  Asp  Glu  Val  Val  Pro
                       20                       25                       30

Leu  Phe  Val  Arg  Asp  Asp  Ala  Val  His  Arg  Ala  Gly  Phe  Asp  Ala  Pro
                       35                       40                       45

Asn  Pro  Leu  Ala  Phe  Leu  Ala  Asp  Cys  Leu  Ala  Ala  Leu  Asp  Ala  Gly
                  50                       55                       60

Leu  Arg  His  Arg  Gly  Gly  Arg  Leu  Ile  Val  Arg  Arg  Gly  Glu  Ala  Ala
        65                       70                       75                       80

Thr  Glu  Val  Arg  Arg  Val  Ala  Glu  Glu  Thr  Gly  Ala  Ala  Arg  Val  His
                            85                       90                       95

Ile  Ala  Ala  Gly  Val  Ser  Arg  Tyr  Ala  Ala  Arg  Arg  Glu  Gln  Arg  Ile
                       100                      105                      110

Arg  Glu  Ala  Leu  Ala  Asp  Ser  Gly  Arg  Glu  Leu  His  Val  His  Asp  Ala
                       115                      120                      125

Val  Val  Thr  Ala  Leu  Ala  Pro  Gly  Arg  Val  Val  Pro  Thr  Gly  Gly  Lys
                  130                      135                      140
```

| | | | | | | | | | | | | | | |
|---|---|---|---|---|---|---|---|---|---|---|---|---|---|---|
| Asp<br>145 | His | Phe | Ala | Val | Phe<br>150 | Thr | Pro | Tyr | Phe | Arg<br>155 | Arg | Trp | Glu | Ala | Glu<br>160 |
| Gly | Val | Arg | Gly | Thr<br>165 | Gln | Thr | Ala | Pro | Arg<br>170 | Thr | Val | Arg | Val<br>175 | Pro | Asp |
| Gly | Val | Ala | Ser<br>180 | Asp | Pro | Leu | Pro | Asp<br>185 | Arg | Asp | Cys | Val | Glu<br>190 | Asn | Leu |
| Ser | Pro | Gly<br>195 | Leu | Ala | Arg | Gly | Gly<br>200 | Glu | Glu | Ala | Gly | Arg<br>205 | Lys | Leu | Val |
| Thr | Ser<br>210 | Trp | Leu | Asn | Gly | Pro<br>215 | Met | Ala | Asp | Tyr | Glu<br>220 | Asp | Gly | His | Asp |
| Asp<br>225 | Leu | Ala | Gly | Asp | Ala<br>230 | Thr | Ser | Arg | Leu | Ser<br>235 | Pro | His | Leu | His | Phe<br>240 |
| Gly | Thr | Val | Ser | Ala<br>245 | Ala | Glu | Leu | Val | His<br>250 | Arg | Ala | Arg | Glu | Lys<br>255 | Gly |
| Gly | Leu | Gly | Gly<br>260 | Glu | Ala | Phe | Val | Arg<br>265 | Gln | Leu | Ala | Trp | Arg<br>270 | Asp | Phe |
| His | His | Gln<br>275 | Val | Leu | Ala | Asp | Arg<br>280 | Pro | Asp | Ala | Ser | Trp<br>285 | Ser | Asp | Tyr |
| Arg | Pro<br>290 | Arg | His | Asp | Arg | Trp<br>295 | Arg | Ser | Asp | Ala | Asp<br>300 | Glu | Met | His | Ala |
| Trp<br>305 | Lys | Ser | Gly | Leu | Thr<br>310 | Gly | Tyr | Pro | Leu | Val<br>315 | Asp | Ala | Ala | Met | Arg<br>320 |
| Gln | Leu | Ala | His | Glu<br>325 | Gly | Trp | Met | His | Asn<br>330 | Arg | Ala | Arg | Met | Leu<br>335 | Ala |
| Ala | Ser | Phe | Leu<br>340 | Thr | Lys | Thr | Leu | Tyr<br>345 | Val | Asp | Trp | Arg | Glu<br>350 | Gly | Ala |
| Arg | His | Phe<br>355 | Leu | Asp | Leu | Leu | Val<br>360 | Asp | Gly | Asp | Val | Ala<br>365 | Asn | Asn | Gln |
| Leu | Asn<br>370 | Trp | Gln | Trp | Val | Ala<br>375 | Gly | Thr | Gly | Thr | Asp<br>380 | Thr | Arg | Pro | Asn |
| Arg<br>385 | Val | Leu | Asn | Pro | Val<br>390 | Ile | Gln | Gly | Lys | Arg<br>395 | Phe | Asp | Ala | Arg | Gly<br>400 |
| Asp | Tyr | Val | Arg | Gly<br>405 | Trp | Val | Pro | Glu | Leu<br>410 | Ala | Glu | Val | Glu<br>415 | Gly | Ser |
| Ala | Ile | His | Glu<br>420 | Pro | Trp | Lys | Leu | Gln<br>425 | Gly | Leu | Asp | Arg<br>430 | Ala | Gly | Leu |
| Asp | Tyr | Pro<br>435 | Asp | Pro | Val | Val | Asp<br>440 | Leu | Ala | Glu | Ala | Arg<br>445 | Ala | Arg | Phe |
| Glu | Arg<br>450 | Ala | Arg | Gly | Leu | Asp<br>455 | | | | | | | | | |

( 2 ) INFORMATION FOR SEQ ID NO:15:

( i ) SEQUENCE CHARACTERISTICS:
    ( A ) LENGTH: 245 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:15:

| | | | | | | | | | | | | | | |
|---|---|---|---|---|---|---|---|---|---|---|---|---|---|---|
| Leu<br>1 | Pro | Glu | Leu | Ser<br>5 | Arg | Leu | Pro | Thr | Asp<br>10 | Trp | Ile | His | His | Pro<br>15 | Trp |
| Asn | Ala | Pro | Glu<br>20 | Ser | Val | Leu | Gln | Ala<br>25 | Ala | Gly | Ile | Glu | Leu<br>30 | Gly | Ser |

```
Asn Tyr Pro Leu Pro Ile Val Gly Leu Asp Glu Ala Lys Ala Arg Leu
        35              40                  45
His Glu Ala Leu Ser Gln Met Trp Gln Leu Glu Ala Ala Ser Arg Ala
    50              55                  60
Ala Ile Glu Asn Gly Ser Glu Gly Leu Gly Asp Ser Ala Glu Val
65              70                  75                      80
Glu Glu Ala Pro Ile Glu Phe Pro Arg Asp Ile Thr Met Glu Thr
            85              Pro     90                  95
Glu Pro Thr Arg Leu Asn Pro Asn Arg Arg Tyr Glu Asp Gln Met Val
            100             105                 110
Pro Ser Ile Thr Ser Ser Leu Ile Arg Pro Glu Glu Asp Glu Glu Ser
            115             120                 125
Ser Leu Asn Leu Arg Asn Ser Val Gly Asp Ser Arg Ala Glu Val Pro
    130             135                 140
Arg Asn Met Val Asn Thr Asn Gln Ala Gln Gln Arg Arg Ala Glu Pro
145             150                 155                     160
Ala Ser Asn Gln Val Thr Ala Met Ile Pro Glu Phe Asn Ile Arg Ile
                165             170                 175
Val Ala Glu Ser Thr Glu Asp Ser Thr Ala Glu Ser Ser Ser Ser Gly
            180             185                 190
Arg Arg Glu Arg Ser Gly Gly Ile Val Pro Glu Trp Ser Pro Gly Tyr
        195             200                 205
Ser Glu Gln Phe Pro Ser Glu Glu Asn Arg Ile Gly Gly Gly Ser Ile
    210             215                 220
Thr Ser Ser Tyr Leu Gln Asn His His Glu Ile Leu Asn Trp Arg Arg
225             230                 235                     240
Leu Ser Gln Thr Gly
                245
```

( 2 ) INFORMATION FOR SEQ ID NO:16:

( i ) SEQUENCE CHARACTERISTICS:
        ( A ) LENGTH: 224 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Leu Glu Glu Leu His Lys Ala Glu Asp Ser Leu Leu Ala Ala Asp Glu
1               5                   10                  15
Thr Ala Ala Lys Ala Glu Ala Asp Val Ala Ser Ile Asn Arg Arg Ile
            20              25                  30
Gln Leu Val Glu Glu Glu Leu Asp Arg Ala Gln Glu Arg Leu Ala Thr
            35              40                  45
Ala Leu Gln Lys Leu Glu Glu Ala Glu Lys Ala Ala Asp Glu Ser Glu
        50              55                  60
Arg Gly Met Lys Val Ile Glu Ser Arg Ala Gln Lys Asp Glu Glu Lys
65              70                  75                      80
Met Glu Ile Gln Glu Ile Gln Leu Lys Glu Ala Lys His Ile Ala Glu
                85              90                  95
Asp Ala Asp Arg Lys Tyr Glu Glu Val Ala Arg Lys Leu Val Ile Ile
            100             105                 110
Glu Ser Asp Leu Glu Arg Ala Glu Glu Arg Ala Glu Leu Ser Glu Gly
            115             120                 125
Lys Cys Ala Glu Leu Glu Glu Glu Leu Lys Thr Val Thr Asn Asn Leu
```

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |
| Lys 145 | Ser | Leu | Glu | Ala | Gln 150 | Ala | Glu | Lys | Tyr | Ser 155 | Gln | Lys | Glu | Asp | Lys 160 |
| Tyr | Glu | Glu | Glu | Ile 165 | Lys | Val | Leu | Ser | Asp 170 | Lys | Leu | Lys | Glu | Ala 175 | Glu |
| Thr | Arg | Ala | Glu 180 | Phe | Ala | Glu | Arg | Ser 185 | Val | Thr | Lys | Leu | Glu 190 | Lys | Ser |
| Ile | Asp | Asp 195 | Leu | Glu | Glu | Lys | Val 200 | Ala | His | Ala | Lys | Glu 205 | Glu | Asn | Leu |
| Ser | Met | His 210 | Gln | Met | Leu | His 215 | Gln | Thr | Leu | Leu | Glu 220 | Leu | Asn | Asn | Met |

(2) INFORMATION FOR SEQ ID NO:17:

(i) SEQUENCE CHARACTERISTICS:
        (A) LENGTH: 1977 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

| | | | | | | |
|---|---|---|---|---|---|---|
| GGATCCCCCG | GGCTGCAGGA | ATTCGGCACG | AGGAGATGAT | GGCAGCGGAG | GGCATCATCG | 60 |
| TGCAGTCTTT | CAATGCAGAC | CTGCTGTACG | AGCCGTGGGA | AGTTGTCGAC | GACGAAGGCC | 120 |
| AATCTTTCAC | CATGTTTGCG | CCTTTCTGGA | ATAGGTGCCT | CAGCATGCCG | TATGATCCTG | 180 |
| CCGCACCGCT | GTTGCCTCCT | AAGAGAATCA | ATTCAGGTGA | CTTATCAATG | TGCCCATCAG | 240 |
| ATGATCTGAT | CTTTGAGGAT | GACTCGGAGA | GGGGAAGCAA | TGCACTTCTT | GCCCGAGCAT | 300 |
| GGTCACCAGG | CTGGCAGAAT | GCAGACAAGG | CACTGACAGC | TTTCCTGAAT | GGTCCTTTGA | 360 |
| TCCACTACTC | AGTGAATCGC | AAGAAAGCAG | ACAGTGCAAG | TACCTCCCTC | TTATCACCGT | 420 |
| ACCTGCATTT | CGGTGAGCTG | AGTGTGCGCA | AGGTCTTCCA | CCTTGTTCGG | ATGAAGCAGC | 480 |
| TTGTGTGGAG | CAATGAGGGC | AATCGTGCAG | CTGAAGAGAG | CTGCACCCTG | TTCTTCGGTC | 540 |
| CATTGGTCTC | CGGGTCGTAC | TCACGGTATC | TGAGTTTCAA | CCACCCATGC | AGCCATGAGA | 600 |
| AGCCCCTTTT | GGCACACCTC | AGGTTCTTCC | CCTGGGTGAT | CAATGAGTGC | TACTTCAAGA | 660 |
| TATGGCGGCA | GGGAAGGACT | GGTTACCCCC | TTGTTGATGC | CGGCATGAGG | GAGCTATGGG | 720 |
| CTACAGGGTG | GTTGCATGAT | CGTATTCGTG | TGGTAGTGTC | AAGTTTCTTC | GTCAAAGTCC | 780 |
| TTCAACTACC | ATGGCGATGG | GGGATGAAGT | ACTTTTGGGA | CACATTATTA | GACGCAGATC | 840 |
| TTGAGAGCGA | TGCACTAGGC | TGGCAGTATA | TCTCTGGCTC | TCTTCCTGAT | GGCCGAGAAC | 900 |
| TTGACCGCAT | TGACAATCCT | CAGCTCGAAG | GCTACAAGTT | TGATCCGCAT | GGTGAGTATG | 960 |
| TCCGAAGGTG | GCTTCCGGAG | CTTGCAAGGT | TGCCAACAGA | ATGGATACAC | CATCCATGGG | 1020 |
| ATGCACCCGC | ATCTGTGCTG | CAAGCTGCAG | GAGTCGAGTT | AGGCTCCAAC | TACCCTCTCC | 1080 |
| CTATAGTTGG | GCTAGATGCA | GCCAACGCCA | GGCTGCAAGA | AGCCCTGTCA | GAAATGTGGC | 1140 |
| AGCTTGAGGC | AGCATCCAGG | GCCGCAATGG | ACAATGGAAT | GGAAGAAGGC | CTTGGCGACT | 1200 |
| CCTCGGAGGT | TCCACCAATT | GAATTTCCTC | GAGAACTACA | GATGGAAGTT | GACCGAGAAC | 1260 |
| CAGCTCGAGT | AACAGCCAAT | GTGCTGACAA | CAGCTCGAAG | ACGCGAGGAT | CAGATGGTGC | 1320 |
| CAACAATGAC | ATCTTCACTA | AACAGGGCTG | AAACTGAGAT | TTCTGCCGAT | TTTATGAACA | 1380 |
| GTGTGGACAG | TAGGGCAGAG | GTACCAACCC | GTGTGAATTT | TGAGCCTGCA | ACTGAGCGGG | 1440 |
| AAGAAAATTT | CCGTACCACT | GCGGGAAATG | TTGCTAGAAC | AAATGGTATT | CATGAGCACA | 1500 |

```
ATAATTTCCA  GCAACCTCAG  CACCGTATGC  GAAATGTTCT  AGCACCATCT  GTATCAGAGG    1560

CATCAAGTGG  CTGGACTGGG  AGAGAGGGAG  GCGTAGTCCC  AGTTTGGTCG  CCTCCTGCAG    1620

CATCAGACCA  TTCAGAAACT  TTTGCCTCTG  ATGAAGCTGA  CATTTCTAGT  AGGAGTTATT    1680

TGGATAGGCA  TCCACAGTCG  CACCGGTTGA  TGAACTGGAG  TCAATTATCC  CAGTCATTGT    1740

TGAGTTCAGA  TGCACGGACA  ACAAGGTCGG  GGAAGTGGAA  AATTCCATGC  AACCAAATTG    1800

GATCGGTTAG  GGTTTTCTCC  GCCCCAGATT  CATATGTAAA  TTGTCCACCT  ATGTGCTTAT    1860

CTATAGTCTG  ATGAGCATGC  AAGCCAGGCA  ATTCTGAGTG  TGACAATAGT  TGTGTAATCT    1920

ATCTGTAGAC  TATCTGTTGG  TCAACAGATT  GTAGAGTGCT  GAACTGGATA  TGTATAC      1977
```

( 2 ) INFORMATION FOR SEQ ID NO:18:

( i ) SEQUENCE CHARACTERISTICS:
        ( A ) LENGTH: 655 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
Ile Pro Arg Ala Ala Gly Ile Arg His Glu Glu Met Met Ala Ala Glu
 1           5                  10                  15

Gly Ile Ile Val Gln Ser Phe Asn Ala Asp Leu Leu Tyr Glu Pro Trp
             20                  25                  30

Glu Val Val Asp Asp Glu Gly Gln Ser Phe Thr Met Phe Ala Pro Phe
             35                  40                  45

Trp Asn Arg Cys Leu Ser Met Pro Tyr Asp Pro Ala Ala Pro Leu Leu
 50                  55                  60

Pro Pro Lys Arg Ile Asn Ser Gly Asp Leu Ser Met Cys Pro Ser Asp
 65                  70                  75                  80

Asp Leu Ile Phe Glu Asp Asp Ser Glu Arg Gly Ser Asn Ala Leu Leu
                 85                  90                  95

Ala Arg Ala Trp Ser Pro Gly Trp Gln Asn Ala Asp Lys Ala Leu Thr
                100                 105                 110

Ala Phe Leu Asn Gly Pro Leu Ile His Tyr Ser Val Asn Arg Lys Lys
            115                 120                 125

Ala Asp Ser Ala Ser Thr Ser Leu Leu Ser Pro Tyr Leu His Phe Gly
        130                 135                 140

Glu Leu Ser Val Arg Lys Val Phe His Leu Val Arg Met Lys Gln Leu
145                 150                 155                 160

Val Trp Ser Asn Glu Gly Asn Arg Ala Ala Glu Glu Ser Cys Thr Leu
                165                 170                 175

Phe Phe Gly Pro Leu Val Ser Gly Ser Tyr Ser Arg Tyr Leu Ser Phe
            180                 185                 190

Asn His Pro Cys Ser His Glu Lys Pro Leu Leu Ala His Leu Arg Phe
        195                 200                 205

Phe Pro Trp Val Ile Asn Glu Cys Tyr Phe Lys Ile Trp Arg Gln Gly
    210                 215                 220

Arg Thr Gly Tyr Pro Leu Val Asp Ala Gly Met Arg Glu Leu Trp Ala
225                 230                 235                 240

Thr Gly Trp Leu His Asp Arg Ile Arg Val Val Ser Ser Phe Phe
                245                 250                 255

Val Lys Val Leu Gln Leu Pro Trp Arg Trp Gly Met Lys Tyr Phe Trp
            260                 265                 270
```

| | | | | | | | | | | | | | |
|---|---|---|---|---|---|---|---|---|---|---|---|---|---|
| Asp | Thr | Leu | Leu | Asp | Ala | Asp | Leu | Glu | Ser | Asp | Ala | Leu | Gly | Trp | Gln |
| | | 275 | | | | | 280 | | | | | 285 | | | |
| Tyr | Ile | Ser | Gly | Ser | Leu | Pro | Asp | Gly | Arg | Glu | Leu | Asp | Arg | Ile | Asp |
| | | 290 | | | | | 295 | | | | | 300 | | | |
| Asn | Pro | Gln | Leu | Glu | Gly | Tyr | Lys | Phe | Asp | Pro | His | Gly | Glu | Tyr | Val |
| 305 | | | | | | 310 | | | | | 315 | | | | 320 |
| Arg | Arg | Trp | Leu | Pro | Glu | Leu | Ala | Arg | Leu | Pro | Thr | Glu | Trp | Ile | His |
| | | | | 325 | | | | | 330 | | | | | 335 | |
| His | Pro | Trp | Asp | Ala | Pro | Ala | Ser | Val | Leu | Gln | Ala | Ala | Gly | Val | Glu |
| | | | 340 | | | | | 345 | | | | | 350 | | |
| Leu | Gly | Ser | Asn | Tyr | Pro | Leu | Pro | Ile | Val | Gly | Leu | Asp | Ala | Ala | Asn |
| | | 355 | | | | | 360 | | | | | 365 | | | |
| Ala | Arg | Leu | Gln | Glu | Ala | Leu | Ser | Glu | Met | Trp | Gln | Leu | Glu | Ala | Ala |
| | 370 | | | | | 375 | | | | | 380 | | | | |
| Ser | Arg | Ala | Ala | Met | Asp | Asn | Gly | Met | Glu | Glu | Gly | Leu | Gly | Asp | Ser |
| 385 | | | | | 390 | | | | | 395 | | | | | 400 |
| Ser | Glu | Val | Pro | Pro | Ile | Glu | Phe | Pro | Arg | Glu | Leu | Gln | Met | Glu | Val |
| | | | | 405 | | | | | 410 | | | | | 415 | |
| Asp | Arg | Glu | Pro | Ala | Arg | Val | Thr | Ala | Asn | Val | Leu | Thr | Thr | Ala | Arg |
| | | | 420 | | | | | 425 | | | | | 430 | | |
| Arg | Arg | Glu | Asp | Gln | Met | Val | Pro | Thr | Met | Thr | Ser | Ser | Leu | Asn | Arg |
| | | 435 | | | | | 440 | | | | | 445 | | | |
| Ala | Glu | Thr | Glu | Ile | Ser | Ala | Asp | Phe | Met | Asn | Ser | Val | Asp | Ser | Arg |
| | 450 | | | | | 455 | | | | | 460 | | | | |
| Ala | Glu | Val | Pro | Thr | Arg | Val | Asn | Phe | Glu | Pro | Ala | Thr | Glu | Arg | Glu |
| 465 | | | | | 470 | | | | | 475 | | | | | 480 |
| Glu | Asn | Phe | Arg | Thr | Thr | Ala | Gly | Asn | Val | Ala | Arg | Thr | Asn | Gly | Ile |
| | | | | 485 | | | | | 490 | | | | | 495 | |
| His | Glu | His | Asn | Asn | Phe | Gln | Gln | Pro | Gln | His | Arg | Met | Arg | Asn | Val |
| | | | 500 | | | | | 505 | | | | | 510 | | |
| Leu | Ala | Pro | Ser | Val | Ser | Glu | Ala | Ser | Ser | Gly | Trp | Thr | Gly | Arg | Glu |
| | | 515 | | | | | 520 | | | | | 525 | | | |
| Gly | Gly | Val | Val | Pro | Val | Trp | Ser | Pro | Pro | Ala | Ala | Ser | Asp | His | Ser |
| | 530 | | | | | 535 | | | | | 540 | | | | |
| Glu | Thr | Phe | Ala | Ser | Asp | Glu | Ala | Asp | Ile | Ser | Ser | Arg | Ser | Tyr | Leu |
| 545 | | | | | 550 | | | | | 555 | | | | | 560 |
| Asp | Arg | His | Pro | Gln | Ser | His | Arg | Leu | Met | Asn | Trp | Ser | Gln | Leu | Ser |
| | | | | 565 | | | | | 570 | | | | | 575 | |
| Gln | Ser | Leu | Leu | Ser | Ser | Asp | Ala | Arg | Thr | Thr | Arg | Ser | Gly | Lys | Trp |
| | | | 580 | | | | | 585 | | | | | 590 | | |
| Lys | Ile | Pro | Cys | Asn | Gln | Ile | Gly | Ser | Val | Arg | Val | Phe | Ser | Ala | Pro |
| | | 595 | | | | | 600 | | | | | 605 | | | |
| Asp | Ser | Tyr | Val | Asn | Cys | Pro | Pro | Met | Cys | Leu | Ser | Ile | Val | Ala | Cys |
| | 610 | | | | | 615 | | | | | 620 | | | | |
| Lys | Pro | Gly | Asn | Ser | Glu | Cys | Asp | Asn | Ser | Cys | Val | Ile | Tyr | Xaa | Val |
| 625 | | | | | 630 | | | | | 635 | | | | | 640 |
| Asp | Tyr | Leu | Leu | Val | Asn | Arg | Leu | Ser | Ala | Glu | Leu | Asp | Met | Tyr | |
| | | | | 645 | | | | | 650 | | | | | 655 | |

(2) INFORMATION FOR SEQ ID NO:19:

(i) SEQUENCE CHARACTERISTICS:
(A) LENGTH: 580 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:19:

| | | | | | |
|---|---|---|---|---|---|
| GGTGATAATC | CACAGTTTGA | GGGATACAAA | TGTGATCCAA | ACGGAGAATA | TGTGCGACGC | 60 |
| TGGCTACCGG | AACTTGCAAG | ACTACCGACT | GAATGGATAC | ATCATCCTTG | GAATGCACCA | 120 |
| GAATCAGTTC | TCCAAGCTGC | AGGTATTGAA | CTAGGCTCAA | ACTACCCTCT | TCCGATTGTG | 180 |
| GAAATAGATG | CAGCAACAGT | GAGACTAGAA | GAAGCACTTA | TTCAAATGTG | GCAACTAGAA | 240 |
| GCAGCTTCAA | GAACTGCAGC | CGAAAACGGA | ACCGAAGAAG | GTCTCGGAGA | CTCGACTGAA | 300 |
| TCCGCCCCTA | TTGCGTTTCC | TCAAGACATA | CAAATGGAGG | AAAGACACGA | ACCGGTTAGG | 360 |
| AACAATCCAC | CTCATGGTAC | TCGGCGCTAC | CAGGAAGAAA | TGGTACCTAG | TAGTACTTAC | 420 |
| TCTAGAGTGA | GAGTGGAAGA | TGAAGAAACT | TCTTTCGAAA | CTCGGCGGAG | ACAGCCGAGC | 480 |
| TGAAGTACCA | ACAAATGCAA | ATACACAGCA | AAATGGACGG | GAACCAATGG | ACCAAGGAAT | 540 |
| GTTGCAGAAT | GTAAATAGAA | ACACTAGACA | ACGACGTAAT | | | 580 |

( 2 ) INFORMATION FOR SEQ ID NO:20:

( i ) SEQUENCE CHARACTERISTICS:
( A ) LENGTH: 194 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:20:

```
Gly Asp Asn Pro Gln Phe Glu Gly Tyr Lys Cys Asp Pro Asn Gly Glu
  1               5                  10                 15
Tyr Val Arg Arg Trp Leu Pro Glu Leu Ala Arg Leu Pro Thr Glu Trp
             20                 25                 30
Ile His His Pro Trp Asn Ala Pro Glu Ser Val Leu Gln Ala Ala Gly
             35                 40                 45
Ile Glu Leu Gly Ser Asn Tyr Pro Leu Pro Ile Val Glu Ile Asp Ala
             50                 55                 60
Ala Thr Val Arg Leu Glu Glu Ala Leu Ile Gln Met Trp Gln Leu Glu
 65                 70                 75                 80
Ala Ala Ser Arg Thr Ala Ala Glu Asn Gly Thr Glu Glu Gly Leu Gly
                 85                 90                 95
Asp Ser Thr Glu Ser Ala Pro Ile Ala Phe Pro Gln Asp Ile Gln Met
             100                105                110
Glu Glu Arg His Glu Pro Val Arg Asn Asn Pro Pro His Gly Thr Arg
             115                120                125
Arg Tyr Gln Glu Glu Met Val Pro Ser Ser Thr Tyr Ser Arg Val Arg
             130                135                140
Val Glu Asp Glu Glu Thr Ser Xaa Xaa Arg Asn Ser Ala Glu Thr Ala
145                150                155                160
Glu Leu Lys Tyr Gln Gln Met Gln Ile His Ser Lys Met Asp Gly Asn
             165                170                175
Gln Trp Thr Lys Glu Cys Cys Arg Met Xaa Ile Glu Thr Leu Asp Asn
             180                185                190
Asp Val
```

( 2 ) INFORMATION FOR SEQ ID NO:21:

( i ) SEQUENCE CHARACTERISTICS:

(A) LENGTH: 2200 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:21:

| | | | | | |
|---|---|---|---|---|---|
| CGCCGCTCTA | GAACTAGTGG | ATCCCCCGGG | CTGCAGGAAT | TCGCGGCCGC | CACAGTCTTT | 60 |
| GATTCGAAGA | TCTTTGTCGC | CGAGAGATAG | CCACTCTGAT | TTGAGTTCTG | AACTATTCTC | 120 |
| TGGAGGAGGT | TGAGGTCTGA | AATCATGGAA | CAACTTGGTT | AGAGTGTGGA | ATTTTAGCTG | 180 |
| ATTTGATCTT | TGATTCATCT | GTGATCATAA | TAACTATGAA | GATGGACAAA | AAGACTATAG | 240 |
| TTTGGTTTAG | AAGAGACCTA | AGGATTGAGG | ATAATCCTGC | ATTAGCAGCA | GCTGCTCACG | 300 |
| AAGGATCTGT | TTTCCTGTCT | TCATTTGGTG | TCCTGAAGAA | GAAGGACAGT | TTATCCTGGA | 360 |
| AGAGCTTCAA | GAGGTGGATG | AAACAATCAC | TTGCTCACTT | ATCTCAATCC | TTGAAGGCTC | 420 |
| TTGGATCTGA | CCTCACTTTA | ATCAAAACCC | ACAACACGAT | TTCAGCGATC | TTGGATTGTA | 480 |
| TCCGCGTTAC | CGGTGCTACA | AAAGTCGTCT | TTAACCACCT | CTATGATCCT | GTTTCGTTAG | 540 |
| TTCGGGACCA | TACCGTAAAG | GAGAAGCTGG | TGGAACGTGG | GATCTCTGTG | CAAAGCTACA | 600 |
| ATGGAGATCT | ATTGTATGAA | CCGTGGGAGA | TATACTGCGA | AAAGGGCAAA | CCTTTTACGA | 660 |
| GTTTCAATTC | TTACTGGAAG | AAATGCTTAG | ATATGTCGAT | TGAATCCGTT | ATGCTTCCTC | 720 |
| CTCCTTGGCG | GTTGATGCCA | ATAACTGCAG | CGGCTGAAGC | GATTGGGCG | TGTTCGATTG | 780 |
| AAGAACTAGG | GCTGGAGAAT | GAGGCCGAGA | AACCGAGCAA | TGCGTTGTTA | ACTAGAGCTT | 840 |
| GGTCTCCAGG | ATGGAGCAAT | GCTGATAGGT | TACTAAATGA | GTTCATCGAG | AAGCAGTTGA | 900 |
| TAGATTATGC | AAAGAACAGC | AAGAAAGTTG | TTGGGAATTC | TACTTCACTA | CTTTCTCCGT | 960 |
| ATCTCCATTT | CGGGGAAATA | AGCGTCAGAC | ACGTTTTCCA | GTGTGCCCGG | ATGAAACAAA | 1020 |
| TTATATGGGC | AAGAGATAAG | AACAGTGAAG | GAGAAGAAAG | TGCAGATCTT | TTTCTTAGGG | 1080 |
| GAATCGGTTT | AAGAGAGTAT | TCTCGGTATA | TATGTTTCAA | CTTCCCGTTT | ACTCACGAGC | 1140 |
| AATCGTTGTT | GAGTCATCTT | CGGTTTTTCC | CTTGGGATGC | TGATGTTGAT | AAGTTCAAGG | 1200 |
| CCTGGAGACA | AGGCAGGACC | GGTTATCCGT | TGGTGGATGC | CGGAATGAGA | GAGCTTTGGG | 1260 |
| CTACCGGATG | GATGCATAAC | AGAATAAGAG | TGATTGTTTC | AAGCTTGCT | GTGAAGTTTC | 1320 |
| TTCTCCTTCC | ATGGAAATGG | GGAATGAAGT | ATTTCTGGGA | TACACTTTTG | GATGCTGATT | 1380 |
| TGGAATGTGA | CATCCTTGGC | TGGCAGTATA | TCTCTGGGAG | TATCCCCGAT | GGCCACGAGC | 1440 |
| TTGATCGCTT | GGACAATCCC | GCGTTACAAG | GCGCCAAATA | TGACCCAGAA | GGTGAGTACA | 1500 |
| TAAGGCAATG | GCTTCCCGAG | CTTGCAGGAT | TGCCAACTGA | ATGGATCCAT | CATCCATGGG | 1560 |
| ACGCTCCTTT | AACCGTACTC | AAAGCTTCTG | GTGTGGAACT | CGGAACAAAC | TATGCGAAAC | 1620 |
| CCATTGTAGA | CATCGACACA | GCTCGTGAGC | TACTAGCTAA | AGCTATTTCA | AGAACCCGTG | 1680 |
| AAGCACAGAT | CATGATCGGA | GCAGCACCTG | ATGAGATTGT | AGCAGATAGC | TTCGAGGCCT | 1740 |
| TAGGGCTAA | TACCATTAAA | GAACCTGGTC | TTTGCCCATC | TGTGTCTTCT | AATGACCAAC | 1800 |
| AAGTACCTTC | GGCTGTTCGT | TACAACGGGT | CAAAGAGAGT | GAAACCTGAG | GAAGAAGAAG | 1860 |
| AGAGAGACAT | GGAGAAATCT | AGGGGATTCG | ATGAAGGGA | GTTGTTTTCG | ACTGCTGAAT | 1920 |
| CTTCTTCTTC | TTCGGAGTGT | GTTTTTCGTT | TCGCAGTCTT | GCTCGTTGGC | ATCAGAAGGG | 1980 |
| AAGAATCTGG | AAGGTATTCA | AGATTCATCT | GATCAGATTA | CTACAAGTTT | GGGAAAAAAT | 2040 |
| GGTTGCAAAT | GATCAAAATA | ATGTGCTGTT | ATAAAGCCTA | ACATGTAGAT | GTGTGAATGT | 2100 |
| GTCTTTTAAC | TCTTTGTTTC | CTTTTGGTTA | TACTCAAAAG | GATATGATTG | GCGCGCGAAT | 2160 |

TCGATATCAA GCTTATCGAT ACCGTCGACC TCGAGGGGGG 2200

(2) INFORMATION FOR SEQ ID NO:22:

(i) SEQUENCE CHARACTERISTICS:
        (A) LENGTH: 598 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Met Lys Met Asp Lys Lys Thr Ile Val Trp Phe Arg Arg Asp Leu Arg
 1               5                  10                  15

Ile Glu Asp Asn Pro Ala Leu Ala Ala Ala His Glu Gly Ser Val
            20                  25                  30

Phe Leu Ser Ser Phe Gly Val Leu Lys Lys Lys Asp Ser Leu Ser Trp
             35                  40                  45

Lys Ser Phe Lys Arg Trp Met Lys Gln Ser Leu Ala His Leu Ser Gln
     50                  55                  60

Ser Leu Lys Ala Leu Gly Ser Asp Leu Thr Leu Ile Lys Thr His Asn
65                  70                  75                  80

Thr Ile Ser Ala Ile Leu Asp Cys Ile Arg Val Thr Gly Ala Thr Lys
                 85                  90                  95

Val Val Phe Asn His Leu Tyr Asp Pro Val Ser Leu Val Arg Asp His
            100                 105                 110

Thr Val Lys Glu Lys Leu Val Glu Arg Gly Ile Ser Val Gln Ser Tyr
         115                 120                 125

Asn Gly Asp Leu Leu Tyr Glu Pro Trp Glu Ile Tyr Cys Glu Lys Gly
     130                 135                 140

Lys Pro Phe Thr Ser Phe Asn Ser Tyr Trp Lys Lys Cys Leu Asp Met
145                 150                 155                 160

Ser Ile Glu Ser Val Met Leu Pro Pro Pro Trp Arg Leu Met Pro Ile
                 165                 170                 175

Thr Ala Ala Ala Glu Ala Ile Trp Ala Cys Ser Ile Glu Glu Leu Gly
             180                 185                 190

Leu Glu Asn Glu Ala Glu Lys Pro Ser Asn Ala Leu Leu Thr Arg Ala
         195                 200                 205

Trp Ser Pro Gly Trp Ser Asn Ala Asp Arg Leu Leu Asn Glu Phe Ile
     210                 215                 220

Glu Lys Gln Leu Ile Asp Tyr Ala Lys Asn Ser Lys Lys Val Val Gly
225                 230                 235                 240

Asn Ser Thr Ser Leu Leu Ser Pro Tyr Leu His Phe Gly Glu Ile Ser
                 245                 250                 255

Val Arg His Val Phe Gln Cys Ala Arg Met Lys Gln Ile Ile Trp Ala
             260                 265                 270

Arg Asp Lys Asn Ser Glu Gly Glu Glu Ser Ala Asp Leu Phe Leu Arg
         275                 280                 285

Gly Ile Gly Leu Arg Glu Tyr Ser Arg Tyr Ile Cys Phe Asn Phe Pro
     290                 295                 300

Phe Thr His Glu Gln Ser Leu Leu Ser His Leu Arg Phe Phe Pro Trp
305                 310                 315                 320

Asp Ala Asp Val Asp Lys Phe Lys Ala Trp Arg Gln Gly Arg Thr Gly
                 325                 330                 335

Tyr Pro Leu Val Asp Ala Gly Met Arg Glu Leu Trp Ala Thr Gly Trp
```

-continued

| | | | | | | | | | | | | | | |
|---|---|---|---|---|---|---|---|---|---|---|---|---|---|---|
| | | 340 | | | | | 345 | | | | | 350 | | |
| Met | His | Asn | Arg | Ile | Arg | Val | Ile | Val | Ser | Ser | Phe | Ala | Val | Lys | Phe |
| | | 355 | | | | | 360 | | | | | 365 | | |
| Leu | Leu | Leu | Pro | Trp | Lys | Trp | Gly | Met | Lys | Tyr | Phe | Trp | Asp | Thr | Leu |
| | 370 | | | | | 375 | | | | | 380 | | | |
| Leu | Asp | Ala | Asp | Leu | Glu | Cys | Asp | Ile | Leu | Gly | Trp | Gln | Tyr | Ile | Ser |
| 385 | | | | | 390 | | | | | 395 | | | | | 400 |
| Gly | Ser | Ile | Pro | Asp | Gly | His | Glu | Leu | Asp | Arg | Leu | Asp | Asn | Pro | Ala |
| | | | | 405 | | | | | 410 | | | | | 415 | |
| Leu | Gln | Gly | Ala | Lys | Tyr | Asp | Pro | Glu | Gly | Glu | Tyr | Ile | Arg | Gln | Trp |
| | | | 420 | | | | | 425 | | | | | 430 | | |
| Leu | Pro | Glu | Leu | Ala | Gly | Leu | Pro | Thr | Glu | Trp | Ile | His | His | Pro | Trp |
| | | 435 | | | | | 440 | | | | | 445 | | | |
| Asp | Ala | Pro | Leu | Thr | Val | Leu | Lys | Ala | Ser | Gly | Val | Glu | Leu | Gly | Thr |
| | 450 | | | | | 455 | | | | | 460 | | | | |
| Asn | Tyr | Ala | Lys | Pro | Ile | Val | Asp | Ile | Asp | Thr | Ala | Arg | Glu | Leu | Leu |
| 465 | | | | | 470 | | | | | 475 | | | | | 480 |
| Ala | Lys | Ala | Ile | Ser | Arg | Thr | Arg | Glu | Ala | Gln | Ile | Met | Ile | Gly | Ala |
| | | | | 485 | | | | | 490 | | | | | 495 | |
| Ala | Pro | Asp | Glu | Ile | Val | Ala | Asp | Ser | Phe | Glu | Ala | Leu | Gly | Ala | Asn |
| | | | 500 | | | | | 505 | | | | | 510 | | |
| Thr | Ile | Lys | Glu | Pro | Gly | Leu | Cys | Pro | Ser | Val | Ser | Ser | Asn | Asp | Gln |
| | | 515 | | | | | 520 | | | | | 525 | | | |
| Gln | Val | Pro | Ser | Ala | Val | Arg | Tyr | Asn | Gly | Ser | Lys | Arg | Val | Lys | Pro |
| | 530 | | | | | 535 | | | | | 540 | | | | |
| Glu | Glu | Glu | Glu | Glu | Arg | Asp | Met | Glu | Lys | Ser | Arg | Gly | Phe | Asp | Glu |
| 545 | | | | | 550 | | | | | 555 | | | | | 560 |
| Arg | Glu | Leu | Phe | Ser | Thr | Ala | Glu | Ser | Ser | Ser | Ser | Ser | Glu | Cys | Val |
| | | | | 565 | | | | | 570 | | | | | 575 | |
| Phe | Arg | Phe | Ala | Val | Leu | Leu | Val | Gly | Ile | Arg | Arg | Glu | Glu | Ser | Gly |
| | | | 580 | | | | | 585 | | | | | 590 | | |
| Arg | Tyr | Ser | Arg | Phe | Ile | | | | | | | | | | |
| | | 595 | | | | | | | | | | | | | |